(12) United States Patent
Hansen et al.

(10) Patent No.: US 6,340,411 B1
(45) Date of Patent: *Jan. 22, 2002

(54) FIBROUS PRODUCT CONTAINING DENSIFYING AGENT

(75) Inventors: Michael R. Hansen, Seattle; Richard H. Young, Sr., Renton, both of WA (US)

(73) Assignee: Weyerhaeuser Company, Federal Way, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,995

(22) Filed: Oct. 7, 1998

Related U.S. Application Data

(62) Division of application No. 08/693,517, filed on Aug. 2, 1996, now abandoned, which is a division of application No. 08/197,483, filed on Feb. 16, 1994, now Pat. No. 5,547,541, which is a continuation-in-part of application No. 08/192,692, filed on Feb. 7, 1994, now abandoned, application No. 09/167,995, which is a continuation-in-part of application No. 08/108,219, filed on Aug. 17, 1993, now Pat. No. 5,607,759, and application No. 08/108,218, filed on Aug. 17, 1993, now Pat. No. 5,641,561, and application No. 08/108,217, filed on Aug. 17, 1993, now Pat. No. 5,547,745, and application No. 08/107,469, filed on Aug. 17, 1993, now Pat. No. 5,672,418, and application No. 08/107,467, filed on Aug. 17, 1993, now Pat. No. 5,693,411, and application No. 07/931,284, filed on Aug. 17, 1992, now Pat. No. 5,308,896, and application No. 07/931,279, filed on Aug. 17, 1992, now Pat. No. 5,589,256, and application No. 07/931,278, filed on Aug. 17, 1992, now Pat. No. 5,352,480, and application No. 07/931,277, filed on Aug. 17, 1992, now Pat. No. 5,538,783, and application No. 07/931,213, filed on Aug. 17, 1992, now Pat. No. 5,300,182, and application No. 07/931,059, filed on Aug. 17, 1992, now Pat. No. 5,543,215.

(51) Int. Cl.[7] .............................................. D21H 17/04
(52) U.S. Cl. ...................... 162/173; 162/179; 428/497; 428/532
(58) Field of Search ........................ 162/12, 158, 166, 162/168.1, 181.1, 184, 173, 179, 182; 428/283, 378, 393

(56) References Cited

U.S. PATENT DOCUMENTS 2,601,597 A    6/1952  Daniel, Jr. et al. .............. 92/21

(List continued on next page.)

FOREIGN PATENT DOCUMENTS

| CA | 729513 | 3/1966 |
| CA | 806352 | 2/1969 |

OTHER PUBLICATIONS

Amosov et al., "Aluminum hydroxy compounds—binders for dry–process paper," Izv. VUZ, Lesnoi Zh., 6:72–76 (1986).

(List continued on next page.)

Primary Examiner—Dean T. Nguyen

(57) ABSTRACT

A densifying agent is applied to fibers in order to improve the densification properties of the fibers. The fibers have hydrogen bonding functional groups. The densifying agent are denser than the fibers to which the densifying agent is applied. The densifying agent can be organic or inorganic. The improved densification properties are observed without the presence of particles bound to the fibers or in the presence of particles that are not bound to the fibers. Softening agents can also be applied to the fibers in order to soften the fibers and articles including such fibers. Softening agents may be selected from the group of densifying agents.

19 Claims, 10 Drawing Sheets

U.S. PATENT DOCUMENTS

| | | | |
|---|---|---|---|
| RE24,011 E | 5/1955 | Ericks | |
| 2,849,000 A | * 8/1958 | Lewing | 128/285 |
| 2,953,187 A | 9/1960 | Francis, Jr. | 154/29 |
| 3,010,161 A | 11/1961 | Duvall | 19/156 |
| 3,059,313 A | 10/1962 | Harmon | 28/80 |
| 3,021,242 A | 12/1962 | Touey | 156/180 |
| 3,070,095 A | 12/1962 | Torr | 128/284 |
| 3,087,833 A | 4/1963 | Drelich | 128/284 |
| 3,327,708 A | 6/1967 | Sokolowski | 117/38 |
| 3,344,789 A | 10/1967 | Arnold et al. | 128/287 |
| 3,350,486 A | 10/1967 | Knoepfler et al. | 428/290 |
| 3,371,666 A | 3/1968 | Lewing | |
| 3,377,302 A | 4/1968 | Gugliemelli et al. | 260/17.4 |
| 3,395,201 A | 7/1968 | Kalwaites | 264/45 |
| 3,409,497 A | 11/1968 | Roseland | 128/284 |
| 3,425,971 A | 2/1969 | Gugliemelli et al. | 260/17.4 |
| 3,494,992 A | 2/1970 | Wiegand | 264/121 |
| 3,521,638 A | 7/1970 | Parrish | 128/284 |
| 3,554,788 A | 1/1971 | Fechillas | 117/140 |
| 3,645,836 A | 2/1972 | Torr | |
| 3,661,154 A | 5/1972 | Torr | 128/284 |
| 3,661,632 A | 5/1972 | Gagliardi et al. | 117/143 A |
| 3,669,103 A | 6/1972 | Harper et al. | 128/156 |
| 3,670,731 A | 6/1972 | Harmon | 128/284 |
| 3,672,945 A | 6/1972 | Taylor | 117/100 B |
| 3,686,024 A | 8/1972 | Nankee et al. | |
| 3,692,622 A | 9/1972 | Dunning | 161/124 |
| 3,745,060 A | 7/1973 | Jumentier et al. | 161/170 |
| 3,758,641 A | 9/1973 | Zweigle | 117/100 B |
| 3,766,922 A | 10/1973 | Krusko | 128/284 |
| 3,777,758 A | 12/1973 | Mesek et al. | 128/284 |
| 3,788,936 A | 1/1974 | Brock et al. | 161/148 |
| 3,804,092 A | 4/1974 | Tunc | 128/284 |
| 3,808,088 A | 4/1974 | Knechtges et al. | 161/187 |
| 3,886,941 A | 6/1975 | Duane et al. | |
| 3,888,256 A | 6/1975 | Studinger | |
| 3,888,257 A | 6/1975 | Cook et al. | |
| 3,901,236 A | 8/1975 | Assarsson et al. | |
| 3,903,889 A | 9/1975 | Torr | |
| 3,908,659 A | 9/1975 | Wehrmeyer et al. | |
| 3,923,592 A | 12/1975 | George et al. | |
| 3,949,035 A | 4/1976 | Dunning et al. | |
| 3,959,569 A | 5/1976 | Burkholder, Jr. | |
| 3,978,257 A | 8/1976 | Ring | |
| 3,991,237 A | 11/1976 | Topfl et al. | |
| 4,007,083 A | 2/1977 | Ring et al. | |
| 4,009,313 A | 2/1977 | Crawford et al. | |
| 4,035,217 A | 7/1977 | Kennette et al. | |
| 4,051,086 A | 9/1977 | Reid | |
| 4,055,180 A | 10/1977 | Karami | |
| 4,061,268 A | 12/1977 | DeMaster | |
| 4,062,451 A | 12/1977 | Gander | |
| 4,071,636 A | 1/1978 | Nishino et al. | |
| 4,096,312 A | 6/1978 | Holst | |
| 4,102,340 A | 7/1978 | Mesek et al. | |
| 4,103,062 A | 7/1978 | Aberson et al. | |
| 4,128,692 A | 12/1978 | Reid | |
| 4,160,059 A | 7/1979 | Samejima | |
| 4,232,674 A | 11/1980 | Melican | |
| 4,235,237 A | 11/1980 | Mesek et al. | |
| 4,250,660 A | 2/1981 | Kitamura et al. | |
| 4,282,121 A | 8/1981 | Goodrich | |
| 4,289,513 A | 9/1981 | Brownhill et al. | |
| 4,289,536 A | 9/1981 | Dereser | |
| 4,324,706 A | 4/1982 | Tabe et al. | |
| 4,332,917 A | 6/1982 | Heslinga et al. | |
| 4,337,111 A | 6/1982 | Kauffmann et al. | |
| 4,338,417 A | 7/1982 | Heslinga et al. | |
| 4,354,487 A | 10/1982 | Oczkowski et al. | |
| 4,364,992 A | 12/1982 | Ito et al. | |
| 4,379,194 A | 4/1983 | Clark et al. | |
| 4,392,908 A | 7/1983 | Dehnel | |
| 4,394,172 A | 7/1983 | Scheuble et al. | |
| 4,404,250 A | 9/1983 | Clarke | |
| 4,410,571 A | 10/1983 | Korpman | |
| 4,412,036 A | 10/1983 | Pedersen et al. | |
| 4,415,388 A | 11/1983 | Korpman | |
| 4,424,247 A | 1/1984 | Erickson | |
| 4,444,830 A | 4/1984 | Erickson | |
| 4,457,978 A | 7/1984 | Wawzonek | |
| 4,467,012 A | 8/1984 | Pedersen et al. | |
| 4,481,076 A | 11/1984 | Herrick | |
| 4,486,501 A | 12/1984 | Holbek | |
| 4,492,729 A | 1/1985 | Bannerman et al. | |
| 4,500,315 A | 2/1985 | Pieniak et al. | |
| 4,507,438 A | 3/1985 | Obayashi et al. | |
| 4,532,176 A | 7/1985 | Briggs et al. | |
| 4,537,767 A | 8/1985 | Rothman et al. | |
| 4,541,871 A | 9/1985 | Obayashi et al. | |
| 4,552,816 A | 11/1985 | Spahic et al. | |
| 4,558,091 A | 12/1985 | Hubbard | |
| 4,597,930 A | 7/1986 | Szal | |
| 4,605,401 A | 8/1986 | Chmelir et al. | |
| 4,610,678 A | 9/1986 | Weisman et al. | |
| 4,666,975 A | 5/1987 | Yamasaki et al. | |
| 4,666,983 A | 5/1987 | Tsubakimoto et al. | |
| 4,673,402 A | 6/1987 | Weisman et al. | |
| 4,676,784 A | 6/1987 | Erdman et al. | |
| 4,685,909 A | 8/1987 | Berg et al. | |
| 4,699,808 A | 10/1987 | Menard et al. | |
| 4,721,647 A | 1/1988 | Nakanishi et al. | |
| 4,734,478 A | 3/1988 | Tsubakimoto | |
| 4,755,178 A | 7/1988 | Insley et al. | |
| 4,758,466 A | 7/1988 | Dabi et al. | |
| 4,764,418 A | 8/1988 | Kuenn et al. | |
| 4,772,492 A | 9/1988 | Bouchette | |
| 4,788,080 A | 11/1988 | Hojo et al. | |
| 4,798,744 A | 1/1989 | Goldstein et al. | |
| 4,818,599 A | 4/1989 | Marcus | |
| 4,822,453 A | 4/1989 | Dean et al. | |
| 4,824,689 A | 4/1989 | Kuenn et al. | |
| 4,826,880 A | 5/1989 | Lesniak et al. | |
| 4,833,011 A | 5/1989 | Horimoto | |
| 4,842,593 A | 6/1989 | Jordan et al. | |
| 4,851,069 A | 7/1989 | Packard et al. | |
| 4,874,811 A | 10/1989 | Borchers et al. | |
| 4,886,697 A | 12/1989 | Perdelwitz, Jr. et al. | |
| 4,888,238 A | 12/1989 | Katz et al. | |
| 4,892,769 A | 1/1990 | Perdelwitz, Jr. et al. | |
| 4,902,559 A | 2/1990 | Eschwey et al. | |
| 4,902,565 A | 2/1990 | Brook | |
| 4,944,734 A | 7/1990 | Wallach | |
| 4,990,551 A | 2/1991 | Haubl | |
| 5,002,814 A | 3/1991 | Knack et al. | |
| 5,002,986 A | 3/1991 | Fujiura et al. | |
| 5,041,104 A | 8/1991 | Seal | |
| 5,057,166 A | 10/1991 | Young, Sr. et al. | |
| 5,064,689 A | 11/1991 | Young, Sr. et al. | |
| 5,128,082 A | 7/1992 | Makoui | |
| 5,149,334 A | 9/1992 | Lahrman et al. | |
| 5,161,686 A | 11/1992 | Weber et al. | |
| 5,217,445 A | 6/1993 | Young et al. | |
| 5,217,576 A | * 6/1993 | Van Phan | 162/158 |
| 5,225,047 A | 7/1993 | Graef et al. | |
| 5,230,959 A | 7/1993 | Young, Sr. et al. | |
| 5,240,562 A | * 8/1993 | Phan et al. | 162/158 |
| 5,252,275 A | 10/1993 | Sultze et al. | |
| 5,252,340 A | 10/1993 | Honeycutt | |
| 5,264,082 A | * 11/1993 | Phan et al. | 162/158 |
| 5,278,206 A | 1/1994 | Gobel et al. | |
| 5,278,222 A | 1/1994 | Stack | |

| | | | | | |
|---|---|---|---|---|---|
| 5,283,123 A | 2/1994 | Carter et al. | GB | 260935 | 11/1926 |
| 5,300,054 A | 4/1994 | Feist et al. | GB | 1 217 452 | 12/1969 |
| 5,300,192 A | 4/1994 | Hansen et al. | GB | 2 004 201 A | 3/1979 |
| 5,308,896 A | 5/1994 | Hansen et al. | GB | 2 007 998 A | 5/1979 |
| 5,312,522 A | 5/1994 | Van Phan et al. | GB | 2 092 895 A | 8/1982 |
| 5,352,480 A | 10/1994 | Hansen et al. | GB | 2119384 A | 11/1983 |
| 5,362,776 A | 11/1994 | Barenberg et al. | GB | 2189127 | 10/1987 |
| 5,378,528 A | 1/1995 | Makoui | JP | 58-25499 | 5/1983 |
| 5,382,610 A | 1/1995 | Harada et al. | JP | 59-189103 | 10/1984 |
| 5,432,000 A | 7/1995 | Young, Sr. et al. | JP | 60-7490 | 2/1985 |
| 5,447,977 A | 9/1995 | Hansen et al. | JP | Sho 61-28422 | 2/1986 |
| 5,449,551 A | 9/1995 | Taniguchi | JP | 61272050 | 12/1986 |
| 5,492,759 A | 2/1996 | Ericksson et al. | JP | 61-282465 | 12/1986 |
| 5,498,478 A | 3/1996 | Hansen et al. | JP | 42994/88 | 2/1988 |
| 5,516,569 A | 5/1996 | Veith et al. | JP | 63035803 | 2/1988 |
| 5,525,345 A * | 6/1996 | Warner et al. ............... 424/402 | JP | 1-156578 | 6/1989 |
| 5,538,783 A | 7/1996 | Hansen et al. | JP | 1-162874 | 6/1989 |
| 5,543,215 A | 8/1996 | Hansen et al. | JP | 1-282389 | 11/1989 |
| 5,547,541 A | 8/1996 | Hansen et al. | JP | 56139991 | 9/1993 |
| 5,547,745 A | 8/1996 | Hansen et al. | JP | 62112553 | 9/1993 |
| 5,571,618 A | 11/1996 | Hansen et al. ............... 428/389 | JP | 01005551 | 11/1993 |
| 5,589,256 A | 12/1996 | Hansen et al. ............... 428/283 | JP | 05227118 | 9/1994 |
| 5,597,873 A | 1/1997 | Chambers et al. | JP | 2530668 | 6/1996 |
| 5,607,759 A | 3/1997 | Hansen et al. ............... 442/147 | JP | 3016879 | 12/1999 |
| 5,609,727 A | 3/1997 | Hansen et al. ............... 162/184 | RU | 1002445 | 3/1983 |
| 5,611,885 A | 3/1997 | Hansen et al. ............... 156/326 | RU | 1390284 | 4/1988 |
| 5,614,570 A | 3/1997 | Hansen et al. ................ 524/13 | WO | WO 88/01316 | 2/1988 |
| 5,633,316 A | 5/1997 | Gartner et al. | WO | WO 88/04704 * | 6/1988 |
| 5,641,561 A | 6/1997 | Hansen et al. ............... 442/417 | WO | WO 90/09236 | 8/1990 |
| 5,672,418 A | 9/1997 | Hansen et al. ............... 428/283 | WO | WO 90/11181 | 10/1990 |
| 5,693,411 A | 12/1997 | Hansen et al. ............... 428/283 | WO | WO 91/05108 | 4/1991 |
| 5,789,326 A | 8/1998 | Hansen et al. ................ 442/59 | WO | WO 91/09916 | 7/1991 |
| 5,807,364 A | 9/1998 | Hansen ....................... 604/367 | WO | WO 91/10010 | 7/1991 |
| 5,851,672 A | 12/1998 | Wang et al. | WO | WP 93/24153 | 12/1993 |
| 5,994,440 A | 11/1999 | Staples et al. | WO | WO 94/04351 | 3/1994 |
| | | | WO | WO 94/04352 | 3/1994 |

FOREIGN PATENT DOCUMENTS

| | | |
|---|---|---|
| CA | 813616 | 5/1969 |
| CA | 841940 | 5/1970 |
| CA | 953 890 | 7/1974 |
| CA | 1052156 | 12/1976 |
| DE | 489 308 | 1/1930 |
| DE | 1 079 796 | 6/1962 |
| DE | 2 048 721 | 6/1971 |
| DE | 29 49 531 A1 | 7/1980 |
| DE | 3313344 | 10/1984 |
| EP | 720390 | 12/1954 |
| EP | 0 071 063 A1 | 2/1983 |
| EP | 0 096 976 A2 | 12/1983 |
| EP | 0 099 586 A3 | 2/1984 |
| EP | 0 122042 A2 | 10/1984 |
| EP | 0156649 | 10/1985 |
| EP | 0 157 960 A1 | 10/1985 |
| EP | 0 210 754 A1 | 2/1987 |
| EP | 0233067 A2 | 9/1987 |
| EP | 0317106 A2 | 5/1989 |
| EP | 0366968 A1 | 5/1990 |
| EP | 0402650 | 12/1990 |
| EP | 0 427 316 A2 | 5/1991 |
| EP | 0 427 317 A2 | 5/1991 |
| EP | 0 429 112 A2 | 5/1991 |
| EP | 0 440 472 A1 | 8/1991 |
| EP | 0 442 185 A1 | 8/1991 |
| EP | 0450922 A2 | 10/1991 |
| EP | 0450923 A2 | 10/1991 |
| EP | 0450924 A2 | 10/1991 |
| EP | P 471 114 A 2 | 2/1992 |
| EP | 0 509 708 A1 | 10/1992 |
| FR | 1 382 716 | 2/1964 |
| GB | 133964 | 9/1923 |
| GB | 254357 | 7/1926 |

| | | |
|---|---|---|
| WO | WO 95/00703 | 1/1995 |

OTHER PUBLICATIONS

Blanchard and Reinhart, "Dyeing of Crosslinked Cotton Containing Glycol Additives," U.S. Dept. of Agriculture, New Orleans, 24:13–17 (Jan. 1992).

Burkholder, "Absorbent Polymers—A New Concept in Fluid Absorption," The Dow Chemical Company Designed Products Laboratory, Midland, Michigan, pp. 73–79 (1973).

Byrd, "How bonds develop during web consolidation," *PTI*, pp. 240–243 (Oct. 1986).

Gorbushin et al., "Investigation of the effect of the nature and concentration of binders on the properties of dry–process paper," Sb. Tr. Tsentr. Nauch.–Issled. Inst. Bumagi, 9:117–123 (1974).

Gugliemelli et al., "Base–Hydrolyzed Starch–Polyacrylonitrile (S–PAN) Graft Copolymer. S–PAN–1:1, PAN M.W. 794,000*", *J. of Applied Copolymer Science*, 13:2007–2017 (1969).

Hawley, Gessner G., *The Condensed Chemical Dictionary*, pp. 853, 950 (1981).

Hoque et al., "Granulation and Tabletting of Iron Oxide–Chromic Oxide Catalyst Mass with the Aid of Binding Ingredients Part II–Cellulosic Derivatives and Polyethylene Glycol as Binding Ingredients," *Fertilizer Technology*, 20:30–35 (1983).

Lindsay, "Absorbent Starch Based Co–polymers—Their Characteristics and Applications," *Formed Fabrics Industry*, to pp. 20, 24 and 26 (May 1977).

Lysogorskaya et al., "Effect of Moisture Content on the Development of Interfiber Bonds in Air–Laid Paper," Leningrad Technological Institute of the Pulp and Paper Industry, Zh. Prikl, Khim., 63:(8) 1869–1872 (1990).

Lysogorskaya et al., "Effect of Moisture Content on Development of Interfiber Bonding in the Structure of Air–Dried Paper," Plenum Publ. Corp., pp. 1730–1733 (1991).

Ogurtsov et al., "Effect of the modulus of elasticity of the binder on the properties of dry–process paper," Sb, Tr, Tsentr. Nauch.–Issled. Inst. Bumagi, 9:123–127 (1974).

S. Lammie, "Use of Glycerine as a Softener for Paper Products," *The World's Paper Trade Review,* p. 2050, Dec. 13, 1962.

Sliwiok and Kowalska, "Investigation of Self–Association of the Selected Glycols and Cellulose Sorbents," Microchemical Journal, 26:68–74 (Jan. 1992).

"Super slurpers: Time for change?, " *Chemical Week,* pp. 21–22 Jul. 24, 1974.

Weaver et al., "Hydrolyzed Starch–Polyacrylonitrile Graft Copolymers: Effect of Structure on Properties*", *J. of Applied Polymer Science,* 15:3015–3024 (1971).

Weaver et al., "Highly Absorbent Starch–Based Polymer," Northern Regional Research Laboratory, Agricultural Research Service, U.S. Dept. of Agriculture, Peoria, Illinois, pp. 169–177.

Neogi et al., "Wet strength improvement via fiber surface modification," *Tappi,* 63:8 86–88 (Aug. 1980).

Watt, W.R., "Incorporation . . . Absorbancy", Paperchem No. AB5609269, Apr. 1985.*

* cited by examiner

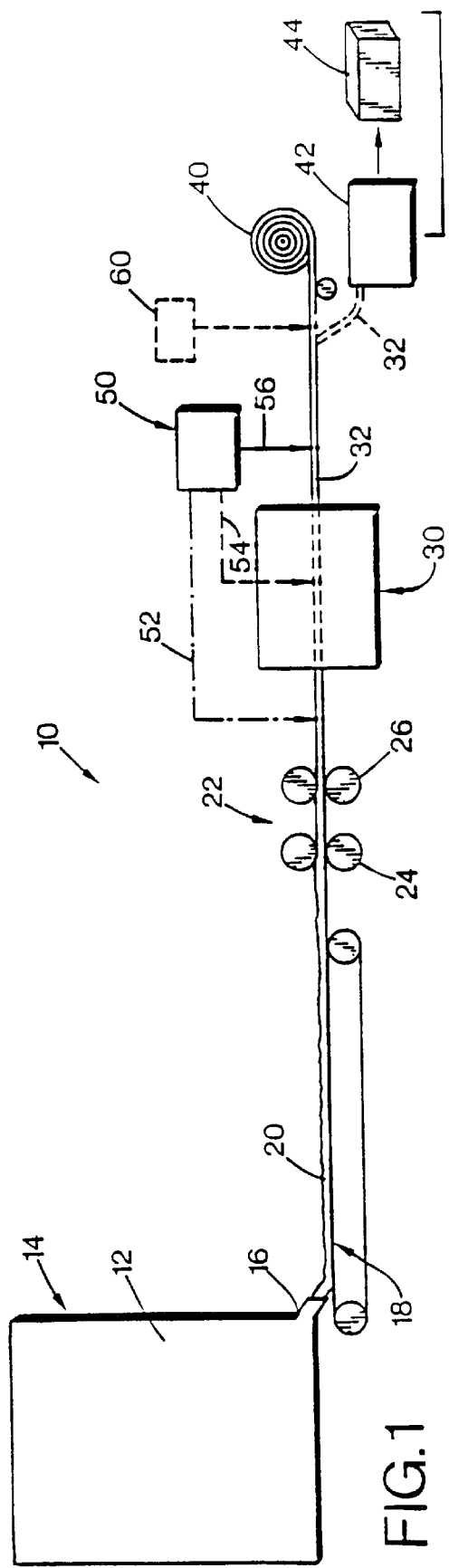
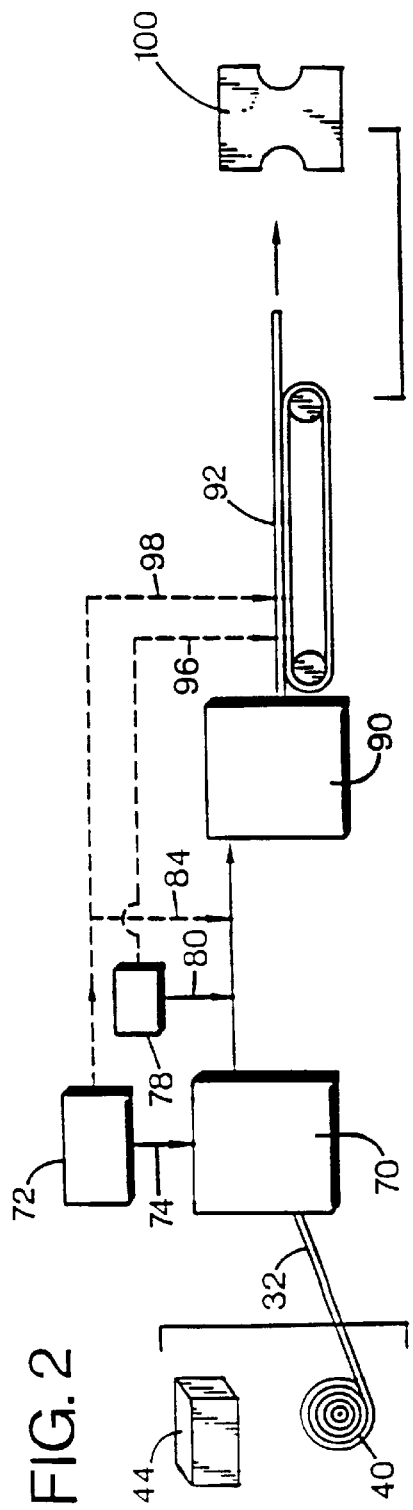
FIG.1
FIG.2

FIG. 6
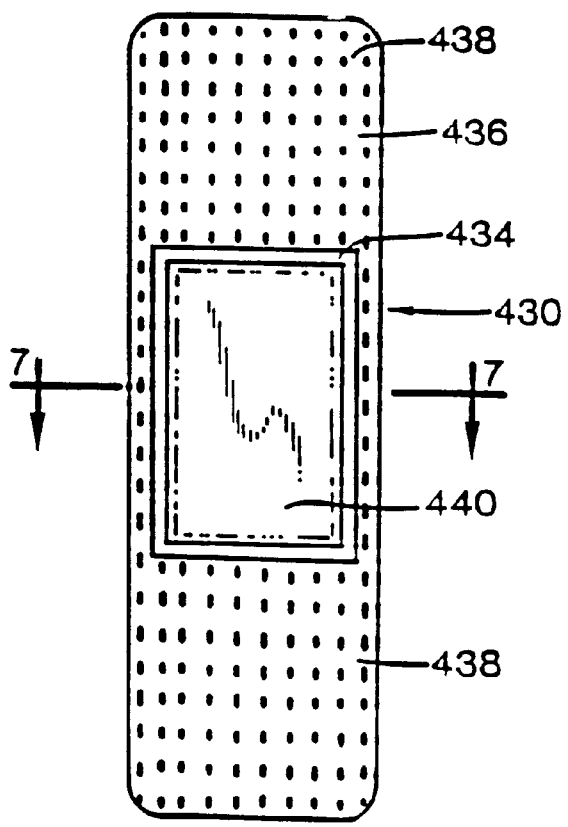
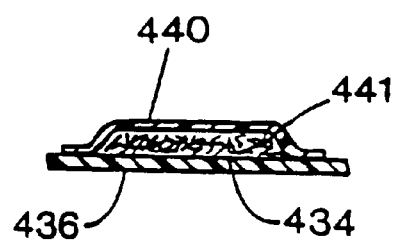
FIG. 7

FIBROUS PRODUCT CONTAINING DENSIFYING AGENT

CROSS REFERENCE TO RELATED APPLICATIONS

This is a divisional application of Ser. No. 08/693,517, filed Aug. 2, 1996, entitled DENSIFYING AGENTS FOR ENHANCING FIBER DENSIFICATION, now abandoned which is a divisional application of Ser. No. 08/197,483, filed Feb. 16, 1994, entitled DENSIFYING AGENTS FOR ENHANCING FIBER DENSIFICATION, now U.S. Pat. No. 5,547,541 which is a continuation-in-part application of the following U.S. patent application, each of which was filed on Aug. 17, 1992, in the names of Michael R. Hansen and Richard H. Young, Sr. Each of these applications is hereby incorporated herein by reference: (1) Ser. No. 07/931,059, entitled "POLYMERIC BINDERS FOR BINDING PARTICLES TO FIBERS" now U.S. Pat. No. 5,543,215; (2) Ser. No. 07/931,277, entitled "NON-POLYMERIC ORGANIC BINDERS FOR BINDING PARTICLES TO FIBERS" now U.S. Pat. No. 5,538,783; (3) Ser. No. 07/931,213, entitled "WET LAID FIBER SHEET MANUFACTURING WITH REACTIVATABLE BINDERS FOR BINDING PARTICLES TO BINDERS" now U.S. Pat. No. 5,300,192; (4) Ser. No. 07/931,278, entitled "REACTIVATABLE BINDERS FOR BINDING PARTICLES TO FIBERS" now U.S. Pat. No. 5,352,480; (5) Ser. No.07/931,284, entitled "PARTICLE BINDERS FOR HIGH BULK FIBERS" now U.S. Pat. No. 5,308,896; and (6) Ser. No. 07/931,279, entitled "PARTICLE BINDERS THAT ENHANCE FIBER DENSIFICATION." now U.S. Pat. No. 5,589,256.

This is also a continuation-in-part of the following U.S. patent applications, each of which was filed on Aug. 17, 1993 in the names of Micharl R. Hansen and Richard H. Young, Sr., and each of which is hereby incorporated by reference: (7) Ser. No. 08/107,469, entitled "PARTICLE BINDERS" now U.S. Pat. No. 5,672,418; (8) Ser. No. 08/108,219, entitled "PARTICLE BINDING TO FIBERS" now U.S. Pat. No. 5,607,701; (9) Ser. No. 08/107,467, entitled "BINDERS FOR BINDING WATER SOLUBLE PARTICLES TO FIBERS" now U.S. Pat. No. 5,693,411; (10) Ser. No. 08/108,217, entitled "PARTICLE BINDERS" now U.S. Pat. No. 5,547,795; and (11) Ser. No. 08/108,218, entitled "PARTICLE BINDERS TO FIBERS" now U.S. Pat. No. 5,641,561.

Application Ser. No. 08/197,483 is also a continuation-in-part of U.S. patent application Ser. No. 08/192,692, filed on Feb. 7, 1994 now abandoned in the names of Richard A. Jewell, Hugh (NMI) West, Robert H. Young, Elisabeth A. Wallbank, Amar N. Neogi, Donald D. Halabisky, and Michael R. Hansen, entitled "METHODS AND COMPOSITIONS FOR INCREASING THE ABSORBENCY OF SUPERABSORBENT POLYMERS". The benefit of the filing dates of these earlier applications is hereby claimed under 35 U.S.C. § 120.

FIELD OF THE INVENTION

This invention concerns organic and inorganic polymeric and non-polymeric densifying agents for fibers and the use of such agents in enhancing the densification of fibers. The fibers treated with such agents may be easily densified by external application of pressure. The binders may be applied to fibers on a wet-laid fiber sheet manufacturing line, and subsequently fiberized for processing using air lay equipment. In particular embodiments, the invention concerns cellulosic fibers which may then be used, for example, to make absorbent fibers that are densified and incorporated into absorbent products.

BACKGROUND OF THE INVENTION

Superabsorbent polymers have been developed in recent years that are capable of absorbing many times their own weight of liquid. These polymers, which are also known as water insoluble hydrogels, have been used to increase the absorbency of sanitary products such as diapers and sanitary napkins. Superabsorbent polymers are often provided in the form of particulate powders, granules, or fibers that are distributed throughout absorbent cellulosic products to increase the absorbency of the product. Superabsorbent particles are described, for example, in U.S. Patent No. 4,160,059; U.S. Pat. No. 4,676,784; U.S. Pat. No. 4,673,402; U.S. Pat. No. 5,002,814; and U.S. Pat. No. 5,057,166. Products such as diapers that incorporate absorbent hydrogels are shown in U.S. Pat. No. 3,669,103 and U.S. Pat. No. 3,670,731.

One problem with the use of superabsorbents is that the superabsorbent material can be physically dislodged from the cellulosic fibers of an absorbent product. Separation of the superabsorbent from its substrate reduces the absorbency of the product and diminishes the effectiveness of the superabsorbent material. This problem was addressed in European Patent Application 442 185 A1, which discloses use of a polyaluminum chloride binder to bind an absorbent polymer to a fibrous substrate. The polyaluminum binder, however, suffers from the drawback of being an inorganic product that is not readily biodegradable. Moreover, that European patent does not offer any guidance for selecting binders other than polyaluminum chloride that would be useful in binding absorbent particles.

A method of immobilizing superabsorbents is disclosed in U.S. Pat. No. 4,410,571 in which a water swellable absorbent polymer is converted to a non-particulate immobilized confluent layer. Polymer particles are converted to a coated film by plasticizing them in a polyhydroxy organic compound such as glycerol, ethylene glycol, or propylene glycol. The superabsorbent assumes a non-particulate immobilized form that can be foamed onto a substrate. The individual particulate identity of the superabsorbent polymer is lost in this process. The confluent nature of the superabsorbent material can also result in gel blocking, in which absorption is diminished as the water swollen polymers block liquid passage through the film layer.

U.S. Pat. No. 4,412,036 and U.S. Pat. No. 4,467,012 disclose absorbent laminates in which a hydrolyzed starch polyacrylonitrile graft copolymer and glycerol mixture is laminated between two tissue layers. The tissue layers are laminated to each other by applying external heat and pressure. The reaction conditions form covalent bonds between the tissue layers that firmly adhere the tissue layers to one another.

Numerous other patents have described methods of applying binders to fibrous webs. Examples include U.S. Pat. No. 2,757,150; U.S. Pat. No. 4,584,357; and U.S. Pat. No. 4,600,462. Such binders are not described as being useful in binding particulates, such as superabsorbent particles, to fibers. Yet other patents disclose crosslinking agents such as polycarboxylic acids that form covalent intrafiber bonds with individualized cellulose fibers, as in European Patent Application 440 472 A1; European Patent Application 427 317 A2; European Patent Application 427 316 A2; and European Patent Application 429 112 A2. The covalent intrafiber bonds are formed at elevated temperatures and increase the bulk of cellulose fibers treated with the crosslinker by forming intrafiber ester crosslinks. Crosslinking must occur under acidic conditions to prevent reversion of the ester bonds. The covalent bonds within the fibers produce a pulp sheet that is more difficult to compress to conventional pulp sheet densities than in an untreated sheet. Covalent crosslink bonds may also form between the fibers and particles, and occupy functional groups that would otherwise be available for absorption, hence absorption efficiency is decreased.

A particular disadvantage of forming covalent ester intrafiber crosslinks is that the resulting fiber product resists densification. Energy requirements for making densified absorbent products are increased because very high compression pressures must be used to densify the absorbent product. It would be advantageous to provide a method of enhancing densification of crosslinked fibers by reducing energy requirements for densification.

Many different types of particles other than superabsorbents may be added to fibers for different end uses. Antimicrobials, zeolites and fire retardants are but a few examples of particles that are added to fibers. It would be advantageous to provide a method of attaching particles that could be accommodated to the many different particle needs of end users. Moreover, it would be advantageous to reduce particulate waste in the attachment process, and simplify shipment of fiber products that require particulate addition. It would be further advantageous to bind particulates to fibers without requiring the shipment of bulk fibers with adhered particulates because shipping and excessive handling of these fibers subject them to mechanical impact which can dislodge some particles from the fibers. It would also be advantageous to incorporate binders onto fibers during the initial pulp sheet manufacturing process so that the fibers are ready for activation and use at a remote product manufacturing location.

It has previously been important that particles added to cellulose products be insoluble in liquids such as water or liquid binders. It has been thought that liquid insolubility (particularly water insolubility) was an essential characteristic for particles bound to cellulose fibers because soluble particles would be dissolved by a water containing binder. Although the particle could eventually resolidify as the binder evaporated, dissolution of the particle in the binder would cause the particle to diffuse to areas of the product where it was not needed or desired. Water soluble particles have therefore not been used for particles that were to be bound to fibers using a binder.

SUMMARY OF THE INVENTION

The foregoing and other problems have been overcome by providing fibers with hydrogen bonding functional sites, and binders that have a volatility less than water. The binder has a functional group that is capable of forming a hydrogen bond with the fibers, and a functional group that is also capable of forming a hydrogen bond or a coordinate covalent bond with particles that have a hydrogen bonding or coordinate covalent bonding functionality.

The fibers of the present invention may have particles bound to the fibers with a polymeric or non-polymeric binder. The binders comprise binder molecules. The polymeric binder may be selected from the group consisting of polyglycols [especially poly(propyleneglycol)], a polycarboxylic acid, a polycarboxylate, a poly(lactone) polyol, such as diols, a polyamide, a polyamine, a polysulfonic acid, a polysulfonate and combinations thereof. Specific examples of some of these binders, without limitation, are as follows: polyglycols may include polypropylene glycol (PPG) and polyethylene glycol (PEG); poly(lactone) diols include poly (caprolactone) diol;, polycarboxylic acid include polyacrylic acid (PAA); polyamides include polyacrylamide or polypeptides; polyamines include polyethylenimine and polyvinylpyridine; polysulfonic acids or polysulfonates include poly(sodium-4-styrenesulfonate) or poly(2-acrylamido-methyl-1-propanesulfonic acid); and copolymers thereof (for example a polypropylene glycol/polyethylene glycol copolymer). The polymeric binder typically has repeating units. The repeating unit may be the backbone of a compound, such as with a polypeptide, wherein the repeating polyamides occur in the peptide chain. The repeating unit also may refer to units other than backbones, for instance a repeating acrylic acid unit. In such a case, the repeating units may be the same or different. The binder molecules have at least one functional group capable of forming a hydrogen bond or a coordinate covalent bond with particles, and at least one functional group capable of forming a hydrogen bond with the fibers. At this time, the most preferred polymeric binder is polyethylene glycol although another especially preferred polymeric binder is an amide binder such as a polypeptide binder with polyglycine being a specifically preferred example.

The non-polymeric binder has a volatility less than water. The non-polymeric binder molecules have at least one functional group that is capable of forming a hydrogen bond or coordinate covalent bond with the particles, and at least one functional group that is capable of forming hydrogen bonds with the cellulose fibers. The non-polymeric binder is an organic binder, and preferably includes a functional group selected from the group consisting of a carboxyl (for example, carboxylic acids), a carboxylate, a carbonyl (for example, aldehydes), a sulfonic acid, a sulfonate, a phosphoric acid, a phosphate, a hydroxyl (for example, an alcohol or polyol), an amide, amine, and combinations thereof (for example, amino acid or hydroxy acid), wherein there are at least two functionalities on the molecule selected from this group, and the two functionalities are the same or different. Examples of such binders include polyols, polyamines (a non-polymeric organic binder with more than one amine group), polyamides (a non-polymeric organic binder with more than one amide group), polycarboxylic acids (a non-polymeric organic binder with more than one carboxylic acid functionality), polyaldehydes (a non-polymeric organic binder with more than one aldehyde), amino alcohols, hydroxy acids. These binders have functional groups that are capable of forming the specified bonds with the particles and fibers.

More preferably, the organic non-polymeric binder is selected from the group consisting of glycerin, a glycerin monoester, a glycerin diester, glyoxal, ascorbic acid, urea, glycine, pentaerythritol, a monosaccharide or a disaccharide, citric acid, tartaric acid, taurine (2-aminoethanesulfonic acid), p-aminosalicylic acid, dipropylene glycol, and urea derivatives, such as DMDHEU, and combinations thereof. Suitable saccharides include glucose, sucrose, lactose, ribose, fructose, mannose, arabinose, and erythrose. The preferred binders are non-polymeric molecules with a plurality of hydrogen bonding functionalities that permit the binder to form hydrogen bonds to both the fibers and particles. Particularly preferred binders include those that can form five or six membered rings, most preferably six membered rings, with a functional group on the particle surface. At present, glycerin, glycerin monoesters, including monoglycerides, a glycerin diester, including diglycerides, polyglycerin oligomers, a propylene glycol oligomer, urea and combinations thereof (such as glycerin and urea). As used herein, an oligomer refers to a condensation product of polyols, wherein the condensation product contains less than ten monomer units. A polyglycerin oligomer as referred to herein means a condensation product of two or more glycerin molecules. A propylene glycol oligomer as referred to herein means a condensation product of two or more propylene glycol molecules. At this time, a specifically preferred non-polymeric binder is glycerin.

The fibrous material may be cellulosic or synthetic fibers that are capable of forming hydrogen bonds with the binder, while the particles are selected to be of the type that are capable of forming hydrogen bonds or coordinate covalent bonds with the binder. It has unexpectedly been found that this binder system secures particles to fibers exceptionally well. A superior fibrous product is therefore produced that has improved absorbent properties as compared to unbound or covalently bound particles. Formation of the noncovalent bond allows production of a fiber product that is easily manufactured and a web that is easily densified, and that is readily biodegradable and disposable.

In one preferred embodiment, an absorbent product comprises a fibrous cellulosic mat that contains superabsorbent hydrogel particles in particulate form. The superabsorbent particles are capable of forming hydrogen bonds or coordinate covalent bonds with the binder, depending upon the binder, while the binder in turn forms hydrogen bonds with the hydroxyl groups of the cellulose fibers. These noncovalent, relatively flexible bonds between the binder and particles maintain the particles in contact with the fibers, and resist dislodgement of the particles by mechanical forces applied to the mat during manufacture, storage or use. The amount of binder present typically depends on a number of factors, including the nature of the binder and particles, and whether the particles are immediately added to the fibers or after a period of time. Hence, one skilled in the art will realize that the amount of binder suitable and particularly useful for a particular application will vary. However, the binder may suitably be present in an amount of from about 1 to 80 percent of the total weight of the fibrous material. An especially suitable range of binder is 1 to 40 percent by weight, or 1 to 25 percent by weight of the fibrous material. The particles bound by the binder of the present invention (via hydrogen/coordinate covalent bonds) may suitably be present in an amount of 0.05 to 80 percent, preferably 1 to 80 percent or 3 to 80 percent, or more than 3 percent by weight of the total weight of the fibrous material and the particles. A particularly suitable range of particles is 3 to 40 percent by weight of the fibrous material and particles. A preferred weight ratio of particle to binder is 8:1 to 50:1. An example of a suitable particle is a superabsorbent polymer such as a starch graft polyacrylate hydrogel fine or larger size particle such as a granule, which forms hydrogen bonds with the binder. The binder also forms hydrogen bonds with the hydroxyl groups of the cellulose, thereby securely attaching the superabsorbent particles to the fibers.

The present invention also includes a method of binding particles to fibers wherein the particles are substantially insoluble in the binder (and soluble in water) and therefore retain their solid particulate form following binding. The particles, whether or not water soluble, preferably have functional groups that can form hydrogen bonds or coordinate covalent bonds with the binder, and the binder in turn is capable of forming hydrogen bonds to the fibers. Other particles without the desired functionality also may be included in the fiber product, but such particles will not be bound as strongly in the same manner.

In especially preferred embodiments, the fibers are cellulosic and the particles are superabsorbent particles that are bound to the binder by hydrogen bonds. The fibers may also be continuous or discontinuous synthetic or natural fibers having a hydrogen bonding functional group that hydrogen bonds with the binder. The binder is suitably applied to the fibers in an amount of at least 1 percent, and preferably no more than 80 percent, by total weight of the fibrous material. The particles may be bound to the fibers at less than 150° C. or without any external application of heat at ambient temperature (e.g., about 25° C.). Particles may also be bound in the absence of any external application of pressure, or in the absence of external heat and pressure.

In some embodiments the binder is associated with the fibers as a solid (for example, a dry powder or a dried liquid), and the fibers contain at least 7 percent water by weight when the binding step is performed. This level of moisture in the fibers provides sufficient mobility of reactants to allow the particles and fibers to bind well to each other. When a liquid binder is used (for example, glycerin or a solution of glycine powder), the fibers suitably contain at least about 0.5 percent water by weight. A solid binder is suitably used with fibers having less than 0.5 percent water by weight if the binder is heated above its melting point to liquefy it. The solid can be applied to the fibers as a supersaturated solution or the solid binder may be heated above its melting point to liquefy the binder, which is later applied to the fibers. Upon solidifying the binder is deactivated. A solid binder may be thermoplastic or meltable, such that it can be heated above its melting point/or softening point and then cooled to fuse fibers to each other. The thermoplastic properties of the binder can also provide additional mechanical adherence between the particles and fibers. In some embodiments, a thermoplastic binder such as urea may be employed which can adhere particles both thermoplastically and with hydrogen bonding.

In other embodiments, the particles are soluble in water but have reduced solubility in the binder such that the particles can be bound in solid particulate form to the fibers. Addition of the binder does not dissolve the particle and cause it to diffuse away from its desired site of attachment to the fibers.

The binder attaches the particles to the fibers, and forms a bond that has been found to be resistant to mechanical disruption. A significant advantage of these binders is that the binder and particle together on the fiber have been found to reduce the pressure required to densify the fibers. The binders can also be present on fibers in an inactive state for more than a week, a month, or a even a year, then later activated or reactivated to bind particles to the fibers.

Liquid binders (which includes neat liquids or aqueous solutions of solid binders) can be placed on the fibers, dried, and later activated by moistening the fibers. Alternatively, a dry solid binder may be added to the fibers and later activated by addition of a liquid. An inactive binder can also be activated by applying kinetic energy to the fibers after the binder and fibers reach an equilibrium moisture content with the atmosphere (hereinafter referred to as "air dry"). Kinetic energy can be applied to the binder and fibers, for example and without limitation, by applying mechanical agitation, pressure from an external source, or using ultrasonics. In yet other embodiments, the binder may be activated or reactivated by heating the fibers after applying the binder to the fibers.

The capacity for activation or reactivation allows the binder to be applied to the fibers, which are then shipped to distribution points with the binder in an inactive form. The binder is then activated at the distribution point (for example, a customer's facility) where particles are added to the fibers and bound thereto. As used herein, binder "activation" includes both activation of previously inactive binders (such as solid binders in the absence of liquid) or activation of previously active binders (such as a liquid binder that has been dried).

Another advantage of the present invention is that the binder can be activated or reactivated in a pattern that corresponds to a desired distribution of particles in fibrous material. An activation fluid, such as an activation liquid, for example, can be applied to the areas of a diaper that will be initially moistened by urine during use. Examples, without limitation, of a suitable activation liquid include water, lower-alkyl alcohols, polyols such as the glycols, acetone, and combinations thereof, such as water and glycerin. When the activating fluid is a liquid such as water, the water may be sprayed or otherwise applied and may be provided in the form of steam or moisture-laden gas, such as humid air. Other liquid activation fluids may be applied in the same manner. Superabsorbent particles can be added to activated areas of the diaper and adhered almost exclusively in those areas where initial urine absorption is required. Targeted activation of binder allows particles to be efficiently and economically attached to the fibers, with reduced particle wastage. Moreover, targeted binder activation and particle adherence increases the absorptive efficiency of the product by diminishing excessive wicking of liquid within the plane of an absorptive product.

The invention also is directed to fibrous products produced by any of the methods described herein, and to absorbent articles comprised of such fibrous products. These fibrous products include fibers with inactive or activatable binders. A fibrous product may be individual fibers or webs made thereof.

The present invention relates to the above objects, features and advantages individually as well as collectively. The foregoing and other features and advantages of the invention will become more apparent from the following detailed descriptions and accompanying drawings.

BRIEF DESCRIPTION OF THE DRAWINGS

FIG. 1 is a schematic illustration of a wet laid sheet manufacturing line illustrating the application of binders in accordance with the present invention during the manufacture of a fiber sheet.

FIG. 2 is a schematic illustration of a binder activation and particulate attachment process in accordance with the present invention.

FIG. 6 illustrates a plan view of a bandage incorporating fibers of the present invention.

FIG. 7 is a sectional view of the bandage of FIG. 6, taken along line 7—7 of FIG. 6.

DETAILED DESCRIPTION OF SEVERAL PREFERRED EMBODIMENTS OF THE INVENTION

I. Processing of Fibers

Figure 3:
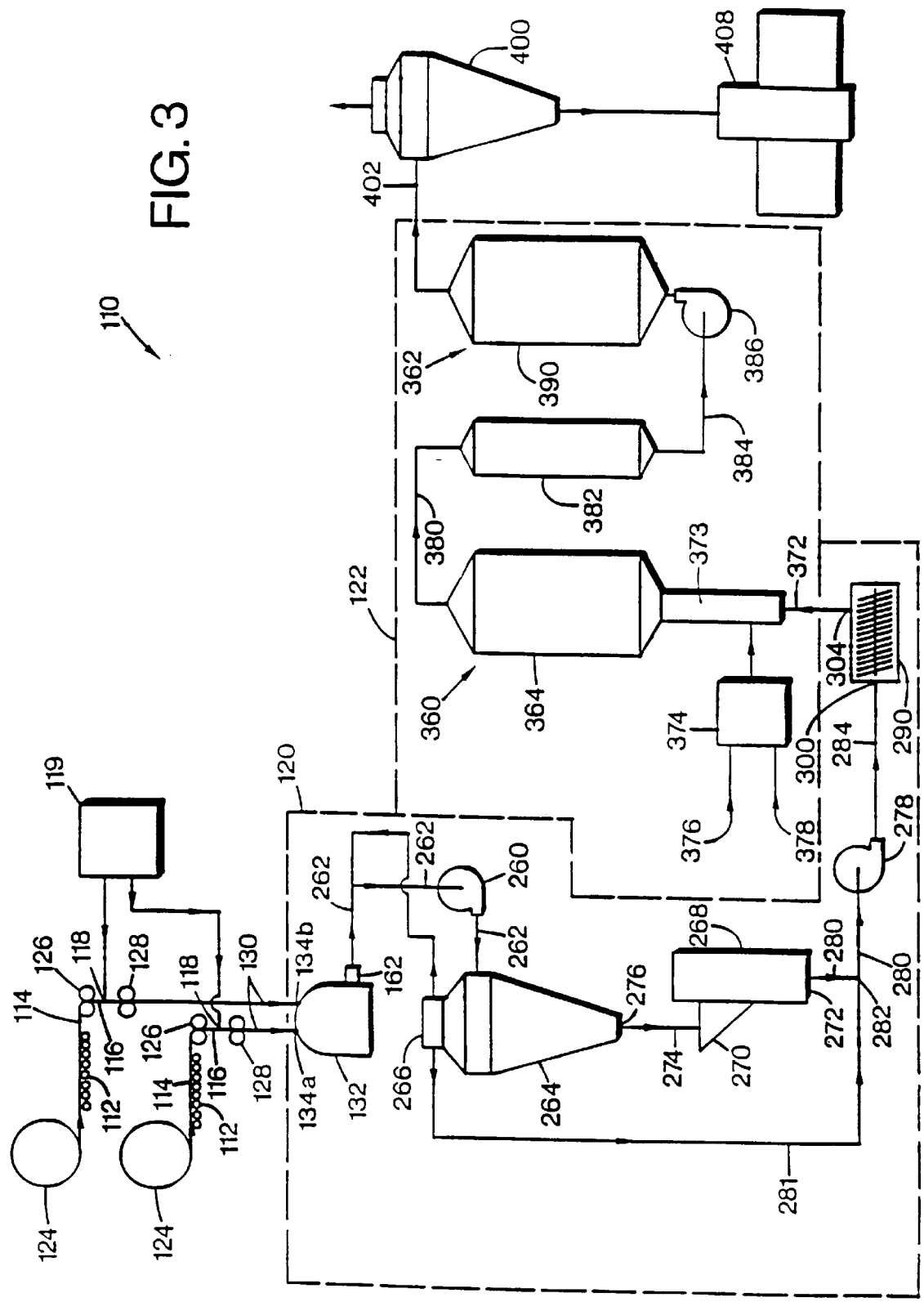
FIG. 3 is a schematic depiction of the components of an apparatus of the present invention that produce high bulk fibers.

FIG. 1A illustrates a wet laid sheet manufacturing line such as a pulp sheet manufacturing line 10. In this manufacturing line, a pulp slurry 12 is delivered from a headbox 14 through a slice 16 and onto a Fourdrinier wire 18. The pulp slurry 12 typically includes cellulose fibers) such as wood pulp fibers and may also include synthetic or other non-cellulose fibers as part of the slurry. Water is drawn from the pulp deposited on wire 18 by a conventional vacuum system, not shown, leaving a deposited pulp sheet 20 which is carried through a dewatering station 22, illustrated in this case as two sets of calendar rolls 24, 26 each defining a respective nip through which the pulp sheet or mat 20 passes. From the dewatering station, the pulp sheet 20 enters a drying section 30 of the pulp manufacturing line. In a conventional pulp sheet manufacturing line, drying section 30 may include multiple canister dryers with the pulp mat 20 following a serpentine path around the respective canister dryers and emerging as a dried sheet or mat 32 from the outlet of the drying section 30. Other alternate drying mechanisms, alone or in addition to canister dryers, may be included in the drying stage 30. The dried pulp sheet 32 has a maximum moisture content pursuant to the manufacturer's specifications. Typically, the maximum moisture content is no more than 10% by weight of the fibers and most preferably no more than about 6% to 8% by weight. Otherwise, the fibers tend to be too damp. Unless overly damp fibers are immediately used, these fibers are subject to degradation by, for example, mold or the like. The dried sheet 32 is taken up on a roll 40 for transportation to a remote location, that is, one separate from the pulp sheet manufacturing line, such as at a user's plant for use in manufacturing products. Alternatively, the dried sheet 32 is collected in a baling apparatus 42 from which bales of the pulp 44 are obtained for transport to a remote location.

A binder of the type explained in detail below is applied to the pulp sheet from one or more binder applying devices, one of which is indicated at 50 in FIG. 1. Any binder applying device may be used, such as sprayers, roll coaters, immersion applicators or the like. Sprayers are typically easier to utilize and incorporate into a pulp sheet manufacturing line. As indicated by the arrows 52, 54 and 56, the binder may be applied at various locations or at multiple locations on the pulp sheet manufacturing line, such as ahead of the drying stage 30 (indicated by line 52), intermediate the drying stage 30 (as indicated by line 54), or downstream from the drying stage 30 (as indicated by the line 56). Water-based binders, such as non-polymeric urea, are typically applied at a location where sufficient drying can still take place in the drying stage to produce a dried binder containing fiber sheet with no more than the maximum desired moisture content. Consequently, to take advantage of the drying stage 30, water-based binders are typically applied at locations 52 or 54. At location 52, the water remaining in the sheet or mat 20 at this stage tends to interfere with the penetration of the binder into the sheet. Consequently, application of the binder after some drying has taken place, for example at location 54, is preferable. If water-based binders are applied at location 56 in an amount which would cause the moisture content of the sheet to exceed the desired maximum level, an additional drying stage (not shown) may be included in the pulp manufacturing line to bring the moisture content down to the desired level.

A non-aqueous based binder, such as glycerin, is most preferably added downstream from the drying stage at location 56 or during the drying stage as indicated by location 54. However, liquid non-aqueous binders may also be added at a location, such as location 52, upstream of the drying stage. At this latter location, the water in the wet web at this point may tend to attract these binders into the mat or sheet as the binders tend to be hydroscopic. Since non-aqueous binders typically do not enhance the degradation of the product due to the addition of moisture to the sheet, they can be applied downstream from the drying stage without bringing the moisture content of the sheet above the desired maximum level.

The particulate materials, selected as explained below, may be added to the sheet and adhered thereto by the binders on the pulp manufacturing line, such as indicated by the particulate applicator 60, which may comprise a bulk or volumetric metering device. These particles may be sprinkled, poured or otherwise added to the sheet. To facilitate the adherence of these particulates to the sheet at this location, enough moisture must remain in the sheet, in the case of aqueous binders, to enable the bonding between the particles and fibers as explained below. For non-aqueous binders, the particles in this case are preferably added while the binder is still wet or heated to facilitate the reaction. Particles can be added on the pulp sheet manufacturing line in this manner, with a subsequent drying stage being utilized to reduce the moisture content following particulate addition. However, if a water-based binder makes the fibers too wet following the addition of the particles, this is not the preferred approach.

Although the above approach is advantageous because the particles are strongly bound to the fibers, during transportation of rolls or bales of these fibers it is possible for particles to become dislodged by mechanical impact during transport. In addition, this approach interferes with the customization of the fiber application at a user's location. For example, a user may want the capability of selecting particular types or brands of particles for adherence to the fibers in the user's products, without having this selection made by a pulp sheet manufacturer who incorporates the particles into the pulp sheet during its manufacture. Also, certain particles may degrade over time, making it advantageous to add such particles immediately prior to incorporation into products. For example, superabsorbent particles are susceptible to absorbing moisture from the atmosphere during shipment. Particles with a relatively short shelf life, such as certain zeolites (e.g. Abscents with odor absorbing materials which can become saturated with odors over time) being one example, may also degrade over time. Another example is zeolites with silver salts as antimicrobial agents which can photodegrade. Therefore, it is also advantageous to provide a fibrous product in which the end user of the product may incorporate the desired particles at the time the fibers are converted into products.

Therefore, in keeping with this latter preferred approach, as illustrated in FIG. 2, the respective rolls 40 or bales 44 of binder-containing fibers, without particles, are transported to a remote location for use by a user. These rolls or bales (or otherwise transported fibers, e.g., bagged, containerized or otherwise in bulk form) are then refiberized by a fiberizing apparatus 70. Although any fiberizer may be used, a typical fiberizing apparatus 70 is a hammermill which may be used alone or in conjunction with other devices such as picker rolls or the like for breaking up the sheet 32 or bales 42 into individual fibers.

A particulate material adding mechanism 72 (e.g., like mechanism 60) delivers the desired particulate materials to the fibers at the desired location in the user's process. Again, the device 72 typically comprises a metering mechanism, although any suitable device for adding particulates to fibrous materials may be used. For example, the particulates may be delivered as indicated by line 74 to the fiberizing apparatus 70. In the case of some binders, agitation of fibers within the fiberizer 70, as explained in greater detail below, activates the binders and causes the particulates to be adhered to the fibers by the binder. Alternatively, an activating fluid, which may be a liquid such as water, glycerin, lower-alkyl alcohols, polyols such as the glycols, acetone, and combinations thereof such as water and glycerin, may be sprayed or otherwise applied to the fibers, such as from an activation fluid tank or source 78 by way of a sprayer (not shown) at location 80. The particles may then be applied, as indicated by line 84 to the fibers downstream from the application of the activation liquid 80. Alternatively, the particles which may be added prior to or at location 80, are adhered to the fibers by the binder upon activation of the binder at location 80. As yet another alternative, the fiberized fibers are delivered to an air-laying device 90 and reformed into a desired product such as a web indicated at 92. In the case of air-laid fibers, the activation fluid or liquid may be applied to the web at location 96 with the particles then being added at location 98 as shown with the activated binder then adhering the particles to the fibers. The particles may be applied at a location in the process upstream from the application of the activating liquid at location 96. Alternatively, the activating fluid may be added simultaneously with the addition of particles, so that the activation occurs simultaneously with the addition of particles. The activating fluid also may be added after the particles are added to the fibers. In addition, the binder may be activated at specifically defined locations on the web 92, such as in target zones of an absorbent core of a product with the particles then only being applied to these target zones, thereby minimizing the wasting of the particulate material. A specific example of a target zone is the crotch region of a diaper where most diaper wetting would occur. The application of superabsorbent particles to such a zone places these particles at a location where they are most useful in absorbing liquid. The web 92, with or without other components of the end user's product, is then processed into the user's product, such as being included within a disposable diaper 100.

Again, with this approach, the end user of the fibers may readily select particles to be applied to its product and may activate the binder as required to enhance the efficient production of the user's product. In addition, the user has flexibility in air laying or otherwise combining the binder containing fibers into a finished product with the desired particulates. The binder containing fibers, because the binders are all water soluble, are preferably not wet laid because wet laying would remove at least some of the binder. Not only is handling and shipping of the particulate containing products avoided by the manufacturer of the pulp sheet, enhanced adhesion of particulates to the fibers results because the particles are not subjected to mechanical forces between the location of manufacture of the fibers and the location at which the particulate materials are added.

II. Fiber Characteristics

The present invention includes a method of binding particles to fibers, and the product, including absorbent end-products, that are produced by such method. In particularly preferred embodiments, the product is a cellulosic or synthetic fiber to which superabsorbent hydrogel polymer particles are adhered by a binder, and absorbent products made therefrom. Suitable fibers include wood pulp fibers, which can be obtained from well known chemical processes such as the kraft and sulfite processes. The invention also includes a combination of wood pulp and certain binders, which for the purpose of this combination are bulk fibers in roll form having a basis weight of at least 350 grams per square meter (g/m$^2$) or bale form. The bulk fibers can have a density of at least about 400 kg/m$^3$. Preferred bulk fibers are wood pulp fibers or softwood pulp fibers. The pulp fibers may be chemical or thermomechanical or chemithermomechanical or combinations thereof. The preferred pulp fiber is chemical. In these processes, the best starting material is prepared from long fiber coniferous wood species, such as pine, douglas fir, spruce and hemlock. Wood pulp fibers can also be obtained from mechanical processes, such as ground wood, mechanical, thermomechanical, chemimechanical, and chemithermomechanical pulp processes. The fibers are preferably elongated, for example having a length to width ratio of about 10:1 to 5:1.

The fibers of the present invention also include fibers that are pretreated prior to the application of a binder to the fibers. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire-retardant chemicals include, by way of example, sodium borate/boric acid, urea, urea/phosphates, etc. In addition, the fibers may be pretreated with surfactants or other liquids, such as water or solvents, which modify the surface of the fibers. Other pretreatments include exposure to antimicrobials or pigments.

The fibers also may be pretreated in a way which increases their wettability. The fibers also may be pretreated with conventional cross-linking materials and may be twisted or crimped, as desired. Pretreating cellulose fibers with chemicals which result in lignin or cellulose rich fiber surfaces also may be performed in a conventional manner.

Bleaching processes, such as chlorine or ozone/oxygen bleaching may also be used in pretreating the fibers. In addition, the fibers may be pretreated, as by slurrying the fibers in baths containing various solutions. For example, antimicrobial solutions (such as solutions of antimicrobial particles as set forth below), as well as solutions of fertilizers and pesticides, and/or fragrances and flavors, for release over time during the life of the fibers. Fibers pretreated with other chemicals, such as thermoplastic and thermoset resins also may be used. Combinations of pretreatments also may be employed with the resulting pretreated fibers then being subjected to the application of the binder coating as explained below.

Ground wood fibers, recycled or secondary wood-pulp fibers, and bleached and unbleached wood-pulp fibers can be used. Details of the production of wood pulp fibers are well known to those skilled in the art. These fibers are commercially available from a number of companies, including Weyerhaeuser Company, the assignee of the present invention.

The fibers also can be any of a variety of other natural or synthetic fibers; however, all of the fibers to which particles are attached in accordance with the present invention include a hydrogen-bonding functionality. This does not preclude the blending of such fibers with fibers lacking this characteristic. However, the f ibers lacking a hydrogen bonding functionality will not have particles bonded thereto with the strength and manner of the bonds that would be present if the fibers had a hydrogen-bonding functionality.

A hydrogen bond is an intermolecular force that occurs between hydrogen atoms that are covalently bonded to small, strongly electronegative elements (such as nitrogen and oxygen) and nonbonding electron pairs on other such electronegative elements, A hydrogen bonding functionality is a functional group that contains an oxygen or nitrogen atom, for example hydroxyls, carboxyls, sulfonic acids, sulfonamides, ethers, esters, epoxides, carbonyls, amines, urethanes and others, that is capable of forming a hydrogen bond. The orbitals of the nonbonding electron pairs on the oxygen or nitrogen overlap with the relatively empty is orbital of the hydrogen covalently bonded to another nitrogen or oxygen atom. The is orbital of the hydrogen is relatively empty due to the unequal sharing of the electrons in the covalent bond between it and the small electronegative atom (oxygen or nitrogen) to which it is bound.

Specific examples of natural fibers that contain a hydrogen bonding functionality include chopped silk fibers, wood pulp fibers, bagasse, hemp, jute, rice, wheat, bamboo, corn, sisal, cotton, flax, kenaf, peat moss, and mixtures thereof. Suitable synthetic fibers with hydrogen bonding functionalities include acrylic, polyester, carboxylated polyolefins, rayon and nylon. The hydrogen-bonding functionality is an ester in acrylic fibers and a carboxylic acid in carboxylated polyolefin fibers, an ester in polyester, an amide in nylon, and a hydroxyl in rayon. Polyethylene and polypropylene would be unsuitable fibers for use in particle to fiber bonding in the manner of the present invention because they include only carbons and hydrogens without any other atoms, such as oxygens or nitrogens, that can participate in hydrogen bonds.

For purposes of convenience, and not to be construed as a limitation, the following description proceeds with reference to the treatment of individual chemical wood-pulp fibers. The fibers are individualized, for example by defiberization in a hammermill. Such individualized fibers are conventionally formed into a mat, and are commercially available, for example as NB 416 fibers from the Weyerhaeuser Company. Another suitable cellulosic mat would include Rayfloc JLD from ITT Rayonier. The cellulose fibers may be in the form of a cellulosic web or loose cellulose fibers.

III. Particle Characteristics

In accordance with the present invention, particles are added to the fibers to give the fibers desired properties, such as, by way of example only, increased absorbency, abrasiveness, or antimicrobial activity. The particle can be any particulate material that has the desired property and which is capable of forming hydrogen bonds or coordinate covalent bonds with the binder. Hydrogen bonds can be formed, as discussed above, by particles that contain certain functional groups, particularly those having an oxygen or nitrogen. Coordinate covalent bonds, in contrast, are formed by donation of a lone pair of electrons on one atom to an empty orbital of another atom. Coordinate covalent bonds differ from covalent bonds in that covalent bonds are formed by a pair of electrons wherein one of the electrons is donated from each of the atoms that participate in the bond. Particles can form coordinate covalent bonds if they have an empty p or d or f orbital that is capable of accepting a pair of electrons from the binder.

A coordinate covalent bond occurs between a donor atom that has a lone pair of electrons to donate to the bond, and an acceptor atom that has an empty orbital to accept the lone pair of electrons from the donor. According to the Aufbau and Pauli principles, electrons occupy the lobes of atomic orbitals one at a time with a maximum of two electrons (with opposite spins) per lobe. The most basic orbital is the s orbital, which is available for bonding the elements in the first row of the periodic table. In the second row of the periodic table, electrons fill first the 2s orbital of Li and Be. However, metals in periods less than three do not have sufficient affinity for electrons to participate in coordinate covalent bonding. Beginning with Group IIIB (boron), the three p orbitals participate in coordinate covalent bonding and the lobes of the p orbitals begin to fill. Boron has one electron in one of the 2p orbitals, thus leaving the other 2p orbitals empty and available for coordinate covalent bonding. An example of a coordinate covalently bonded boron containing particle is boric acid, which is used as an astringent, antiseptic and fire retardant. As shown below, the boron atom of boric acid acts as an acceptor for a lone pair of electrons donated by an oxygen atom of polypropylene glycol (PPG), thereby forming a coordinate covalent bond between a boric acid particle and a PPG binder. The depiction of boric acid shown below is not typical of the aqueous chemistry of boron, but rather is provided to illustrate the type of bonding that is believed to occur in a coordinate covalent bond.

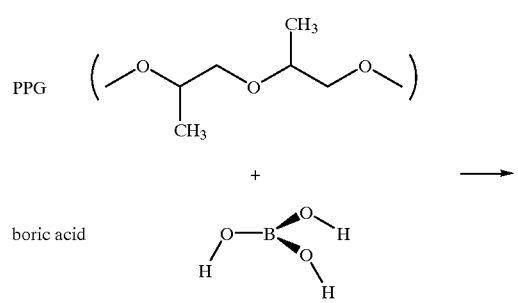

-continued

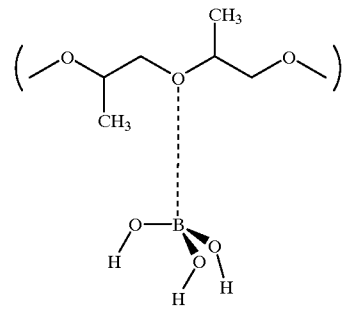

The next element, carbon, usually hybridizes to have one electron in the 2s orbital and the three remaining electrons are singly placed in the three p orbitals. This leaves no lobes empty for coordinate covalent bonding and electron additions proceeding further across that row of the periodic table also leave no lobes empty. Hence, boron is the only element in the second row of the periodic table that is capable of forming coordinate covalent bonds.

Next the third row begins to fill, and the two 3s electrons fill first in sodium and magnesium. Sodium and magnesium have empty d orbitals available for coordination. Examples of magnesium coordination compounds are common. Then aluminum, like boron, places one electron in one of the 3p lobes, and the two other 3p lobes are empty and available for coordinate covalent bonding. The same trends continue across the third row, but the third row elements also have available five 3d lobes so the potential for coordination bonding exists even though 3p orbitals are occupied in the third row. Hence, Al, P, S, and Cl are capable of accepting a pair of electrons from an electron-pair donor to form a coordinate covalent bond. An example of this is found in the bonding in $PCl_5$, aluminum trihydrate, or phosphorous pentasulfide. A phosphorous pentasulfide particle can be used to increase flammability of a product, while aluminum trihydrate is a fire retardant. An example of a coordinate covalently bonded aluminum compound is

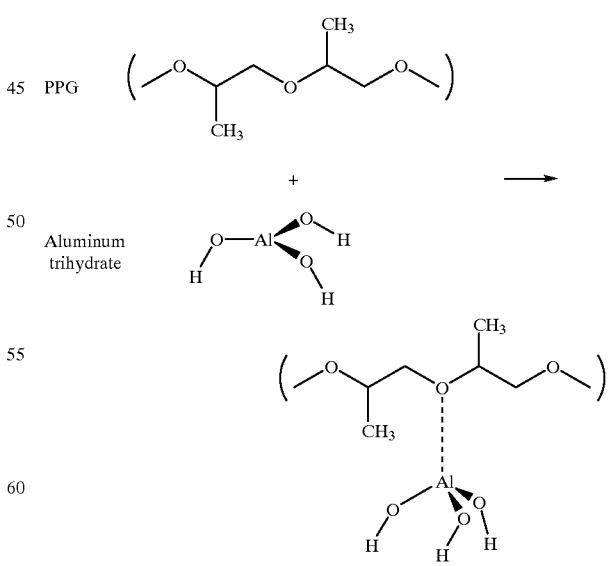

aluminum trihydrate, which may participate in a coordinate covalent bond with a polypropylene glycol (PPG) polymer. In this example, the aluminum atom of aluminum trihydrate acts as an electron acceptor for an electron pair donated by an oxygen atom of the polypropylene glycol (PPG) binder. The depiction of aluminum trihydrate shown above is not typical of the aqueous chemistry of aluminum, but rather is provided to illustrate the type of bonding that may occur in a coordinate covalent bond.

In the next row, the 4s orbital is filled first, then the 3d lobes begin to fill one electron per lobe until all have added a single then a second electron to each lobe until all lobes are filled. However, 4p and 4f orbitals also are available, hence many of the transition elements are capable of forming coordinate covalent bonds.

The elements that have empty orbitals that participate in coordinate covalent bonding include all those except the metals (which excludes hydrogen) in periods one and two, and C, N, O, F,.Ne and He. These metals do not have sufficient affinity for electrons to participate in coordinate covalent bonding. Especially preferred particles contain boron, aluminum, iron, rhodium, osmium, platinum, and palladium, and most particularly boron. Examples of particles that are capable of coordinate covalent bonding are aluminum trihydrate, antimony oxide, arsenic disulfide, bismuth aluminate, bismuth iodide oxide, bismuth phosphate, bismuth subcarbonate, bismuth subgallate, cadmium salycilate, chromic carbonate, chromic hydroxide, chromic oxide, and chromic phosphate. All of the polymeric binders of the present invention [polyglycols (such as PPG), polycarboxylic acids (such as PAA), poly(lactone) diols (such as poly(caprolactone) diol), polyamides, polyamines, etc.] are capable of donating a lone pair of electrons from an electronegative atom, such as oxygen or nitrogen, to form a coordinate covalent bond with a suitable particle that includes an atom having an empty orbital for accepting electrons to form a coordinate covalent bond.

IV. Superabsorbent Particles

In one disclosed embodiment the added particles are superabsorbent particles, which comprise polymers that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof. These superabsorbent materials generally fall into three classes, namely starch graft copolymers, crosslinked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a crosslinked polyacrylate salt, carboxylated cellulose, and a neutralized crosslinked isobutylene-maleic anhydride copolymer.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C.), and NORSOCRYL (supplied by Atochem). The superabsorbent particles come in a variety of sizes and morphologies, for example IM 1000 and IM 1000F. The 1000F is finer and will pass through a 200 mesh screen whereas IM 1000 has some particles that will not pass through a 60 mesh screen. Another type of superabsorbent particle is IM 5600 (agglomerated fines). Superabsorbent particulate hydrophilic polymers also are described in detail in U.S. Pat. No. 4,102,340. That patent discloses hydrocolloid absorbent materials such as cross-linked polyacrylamides.

V. Other Particles

Many particles that form hydrogen bonds or coordinate covalent bonds are suitable for use with the present invention. Some such particles are listed in Table I with an indication of the function of the listed particles. The particles listed in Table I are water-insoluble particles.

TABLE I

| Water-Insoluble Particulates For Binding | |
|---|---|
| Name | Function |
| Aluminum Trihydrate | Fire retardant, astringent |
| Acediasulfone | Antibacterial |
| Agaricic acid | Antiperspirant |
| Alclometastone | Topical anti-inflammatory |
| Calcium alginate | Topical hemostatic |
| Amidomycin | Fungicide |
| Antimony oxide | Fire retardant |
| Apigenin | Yellow dye, mordant |
| Arsenic disulfide | Red Pigment |
| Aspirin | Anti-inflammatory; antipyretic |
| Azanidazole | Antiprotozoal (Trichomonas) |
| Azelaic acid | Antiacne |
| Baicalein | Astringent |
| Bendazac | Anti-inflammatory |
| Benomyl | Fungicide; ascaricide |
| Benzestrol | Estrogen |
| Benzylpenicillinic acid | Antibacterial |
| Benzylsulfamide | Antibacterial |
| Bergaptene | Antipsoriatic |
| Betasine | Iodine source |
| Bezitramide | Narcotic analgesic |
| Bibrocathol | Topical antiseptic |
| Bietanautine | Antihistaminic |
| Bifenox | Herbicide |
| Bifonazole | Antifungal |
| Binapacryl | Fungicide, miticide |
| Bis(p-chlorophenoxy) methane | Miticide |
| Bismuth aluminate | Antacid |
| Bismuth iodide oxide | Anti-infective |
| Bismuth phosphate | Antacid; protectant |
| Bismuth subcarbonate | Topical protectant |
| Bismuth subgallate | Astringent, antacid; protectant |
| Bisphenol A | Fungicide |
| Bitertanol | Agricultural fungicide |
| Bithionol | Topical anti-infective |
| Bromacil | Herbicide |
| Bromadiolone | Rodenticide |
| Bromcresol green | Indicator |
| Bromcresol purple | Indicator |
| Bromethalinlin | Rodenticide |
| p-Bromoacetanilide | Analgesic; antipyretic |
| 3-Bromo-d-camphor | Topical counterirritant |
| Bromophos | Insecticide |
| Bromopropylate | Acaricide |
| 5-Bromosalicyl-hydroxamic acid | antibacterial (tuberculostatic) |
| 5-Bromosalycilic acid acetate | Analgesic |
| Bromosaligenin | Anti-inflammatory |
| Bromthymol blue | Indicator |
| Broxyquinoline | Antiseptic; disinfectant |
| Bucetin | Analgesic |

TABLE I-continued

Water-Insoluble Particulates For Binding

| Name | Function |
| --- | --- |
| Bumadizon | Analgesic; anti-inflammatory; antipyretic |
| Bupirimate | Fungicide |
| Busulfan | Carcinogen, insect sterilant, antineoplastic |
| Butamben | Topical anesthetic |
| Butrylin | Insecticide |
| Butylated hydroxyanisole | Antioxidant (BHA) |
| Butyl paraben | Pharmaceutic aid; food preservative |
| 4-tert-Butylphenyl salicylate | Light absorber |
| Cacotheline | Indicator |
| Cactinomycin | Antineoplastic |
| Cadmium salycilate | Antiseptic |
| Calamine | Skin protectant |
| Calcium carbonate | Antacid |
| Calcium saccharate | Pharmaceutic aid |
| Calcium tartrate | Preservative; deodorant; antacid |
| Cambendazole | Anthelminthic |
| Candicidin | Topical antifungal |
| Candidin | Topical antifungal |
| Capsaicin | Topical analgesic |
| Captan | Fungicide; bacteriostat |
| Carbadox | Antimicrobial |
| Carbamazepine | Anticonvulsant; analgesic |
| Carbarsone | Antiamebic |
| Carbaryl | Contact insecticide |
| Carbazochrome salycilate | Antihemorrhagic |
| Carbendazim | Fungicide |
| Carbochloral | Hypnotic |
| Carbophenothion | Miticide; insecticide |
| Carboquone | Antineoplastic |
| Carisoprodol | Skeletal muscle relaxant |
| Carthamin | Dye |
| Carvacrol | Disinfectant |
| Cephalin | Local hemostatic |
| Chalcomycin | Antibiotic |
| Chartreusin | Antibiotic |
| Chitin | Vulnerary |
| Chloramben | Herbicide |
| Chloramphenacol palmitate | Antimicrobial |
| Chloranil | Fungicide |
| Chlorbetamide | Antiamebic |
| Chlordimeform | Insecticide |
| Chlorfenac | Herbicide |
| Chlorfenethol | Acaricide |
| Chlorhexidine | Topical antibacterial |
| Chloroazodin | Antibacterial; topical anesthetic |
| Chlorophacinone | Anticoagulant rodenticide |
| p-Chlorophenol | Antiseptic |
| Chlorothricin | Antibiotic |
| Chlorotrianisene | Estrogen |
| Chloroxylenol | Antiseptic; germicide |
| Chlorphenesin | Topical antifungal |
| Chlorphenesin carbamate | Relaxant (skeletal muscle) |
| Chlorphenoxamide | Antiamebic |
| Chlorpropamide | Antidiabetic |
| Chlorpyrifos | Insecticide |
| Chlorquinaldol | Topical antibacterial |
| Chlorsulfuron | Herbicide |
| Chlorothion | Insecticide |
| Chlozoxazone | Relaxant |
| Cholesterol | Pharmaceutic aid |
| Chromic carbonate | Pigment |
| Chromic hydroxide | Pigment |
| Chromic oxide | Abrasive |
| Chromic phosphate | Green pigment |
| Chrysamminic acid | Explosive |
| Chrysarobin | Antipsoriatic |

TABLE I-continued

Water-Insoluble Particulates For Binding

| Name | Function |
| --- | --- |
| Cilastazol | Antithrombotic |
| Cinoxate | Sunscreen agent |

Other suitable water-insoluble particles include proteins, vitamins, zeolites and silica, each of which contains electronegative atoms, such as oxygen or nitrogen groups, or both. An example of a suitable zeolite is Abscents odor absorber available from UOP of Tarrytown, N.Y. An example of a suitable antimicrobial particle is chlorhexidine (N,N"-Bis(4-chlorophenyl)-3,12-diimino-2,4,11,13-tetraazatetradecanediimidamide). The list in Table I is by no means exhaustive as it can be readily determined for each type of particle whether it is capable of forming a hydrogen bond or a coordinate covalent bond. Many of the particles are non-absorbent, or not superabsorbent polymers.

The particles listed in Table I have chemical properties that make them suitable for binding to fibers with the binders of the present invention. The listed particles are organic or inorganic compounds that have little or no water solubility, yet have the capacity to hydrogen bond. Water solubility is preferably low, for example, less than 10 g dissolves completely in 300 ml of water at 25° C., more preferably less than about 1 g in 300 ml at 25° C. This low solubility allows the particles to remain solid, and the hydrogen-bonding capacity allows them to adhere to the fibers even in cases when an aqueous binder is used. Once bound, the particles substantially retain a discrete particulate form instead of dissolving or fusing. Hence, once bound more of the particles are discrete than fused.

Many water-soluble particles that are capable of forming hydrogen bonds or coordinate covalent bonds are suitable for use with the binders of the present invention. Some such water-soluble particles are listed in Table II with an indication of the function of the listed particles.

TABLE II

Particulates For Binding

| Name | Function |
| --- | --- |
| Ethylenediaminetetraacetic acid (EDTA) | Odor absorbent |
| disodium salt of EDTA | Chelator |
| Sodium bicarbonate | Odor absorbent/pH modifier |
| Acarbose | Antidiabetic |
| Acefylline Piperazine | Bronchodilator |
| Acenocoumarol, sodium salt | Anticoagulant |
| Acephate | Insecticide |
| Acetaminophen | Analgesic |
| Acetylleucine Monoethanolamine | Antivertigo aqent |
| Acid Violet 7B | Dye/Stain |
| Acitretin | Antipsoriatic |
| Acranil | Antiprotozoal (Giardia) |
| Acriflavine | Anti-infective |
| Actaplanins | Growth stimulant |
| Algestone Acetophenide | Antiacne |
| Algin | Hemostatic |
| Almagate | Antacid |
| (−)-Ambroxide | Fragrance |
| Ambucaine hydrochloride | Local anesthetic |
| Amodiaquin | Antimalarial |
| Anabasine hydrochloride | Insecticide |

TABLE II-continued

Particulates For Binding

| Name | Function |
| --- | --- |
| o-Anisaldehyde | Fragrance |
| Anisomycin hydrochloride | Topical antitrichomonal |
| Aralkonium chloride | Antiseptic, germicide |
| Asiaticoside | Dermatide, wounds, burns |
| Aspartame | Non-nutritive sweetener |
| Azidoamphenicol | Antimicrobial in eye infections |
| Bebeerine | Antimalarial |
| Potassium benzoate | Preservative, antifungal |
| Benzoyl peroxide | Dermatide, antiacne |
| Benzylidene acetone | Fragrance |
| Bidrin | Insecticide |
| Biphenamine hydrochloride | Antiseborrheic |
| Bishydroxycoumarin | Anticoagulant |
| Bismuth tribromophenate | Topical antiseptic |
| Blasticidin S hydrochloride | Antimicrobial |
| Bromocresyl green | Indicator |
| Bromophenol blue | Indicator |
| Butathamine hydrochloride | Anesthetic |
| Caffeine hydrochloride | CNS Stimulant |
| Calcium ascorbate | Vitamin C/Calcium source |
| Calcium bisulfite | Germicide |
| Calcium thioglycollate | Depilatory |
| Carbachol | Ophthalmic parasympathomimetic |
| Carbowax | Ointment base |
| Cetalkonium chloride | Antibacterial |
| Cethoxonium bromide | Antiseptic |
| Chartreusin | Antimycobacterial |
| Chloramine-T | Topical antiseptic |
| Cinnamic acid | Fragrance |
| Cotarnine chloride | Hemostatic |
| Demercarium bromide | Topical antiglaucoma |
| D-2-deoxyribose | DNA synthesis |
| Dequalinium chloride | Antiseptic |
| Dermostatin | Anti fungal |
| Dexamethasone | Glucocorticoid |
| Diacetone acrylamide | Mfr coatings, adhesives |
| 2,4-Diamino-6-hydroxypyrimidine | Indicator of nitrates/nitrites |
| 2,4-Diaminophenol dihydrochloride | Photographic developer |
| Diamthazole dihydrochloride | Antifungal |
| Diatrizoate sodium | Diagnostic aid |
| Dibekacin sulfate | Antibacterial |
| Disodium 4',5'-dibromofluorescein | FDA approved dye |
| 3,5-Dibromo-4-hydroxybenzenesulfonic acid, sodium salt | Topical disinfectant |
| Dibromopropamidine | Cosmetic preservative |
| Diflorasone | Topical anti-inflammatory |
| Dihydroxyacetone | Artificial tanning agent |
| Diisobutyl sodium sulfosuccinate | Wetting agent/detergent |
| Dikegulac | Plant growth regulator |
| Dimethisoquin | Topical anesthetic |
| Diphenicillin sodium | Antibacterial |
| Diphetarsone | Antiamebic |
| Dipyrone | Analgesic, antipyretic |
| Diquat dibromide | Herbicide, defoliant |
| Dodine | Fungicide |
| Domiphen bromide | Topical anti-infective |
| Dulcin | Non-nutritive sweetener |
| Dymixal ® | Topical burn treatment |
| Ecognidine | Topical anesthetic |
| Edetic acid | Antioxidant |
| Edoxudine | Antiviral |
| Ellagic acid | Hemostatic |
| Endothal | Herbicide, defoliant |
| Eosine I bluish | Dye |
| Eosine yellowish | Cosmetic dye |
| Erythrosine | Food dye |
| Esculin | Skin protectant |
| Ethacridine | Antiseptic |
| Ethambutol hydrochloride | Antibacterial (tuberculostatic) |
| Ethamsylate | Hemostatic |
| Ethylidene dicoumarol | Anticoagulant |
| Ethylstibamine | Antiprotozoal |
| Euprocin dihydrochloride | Topical anesthetic |
| Fast green FCF | Food coloring |
| Fenticonazole nitrate | Topical antifungal |
| Ferric albuminate | Hematinic |
| Ferric chloride hexahydrate | Astringent, styptic |
| Ferric formate | Silage preservative |
| Ferrulic acid, sodium salt | Food preservative |
| Fluorescein, disodium salt | Diagnostic aid |
| Fluoridamid | Plant growth retardant |
| Forminitrazol | Antiprotozoal (Trichomonas) |
| Fortimicin(s) | Antibacterial |
| Foscarnet sodium | Antiviral (HIV-1) |
| Fosetyl Al | Systemic fungicide |
| Fungichromin | Topical antifungal |
| Gallic acid | Astringent, styptic |
| Gentian violet | Topical anti-infective |
| Gluconolactone | Cleaner |
| Gossypol | Rubber antioxidant |
| Heparin | Anticoagulant |
| Hexamethylolmelamine | Fireproofing agent |
| Mexamidine | Antiseptic, anti-acne |
| Homatropine | Anticholinergic (opthtalmic) |
| Hydrastinine hydrochloride | Uterine hemostatic |
| Hydrocortisone phosphate, disodium salt | Glucocorticoid |
| Hydroquinine hydrochloride hemihydrate | Depigmentor |
| Hydroxyamphetamine hydrobromide | Andregenic (opthtalmic) |
| Hydroxybutyranilide | Antioxidant |
| 3-Hydroxycamphor | Topical antipruritic |
| 1-(Hydroxymethyl)-5, 5-dimethylhydantion | Cosmetic preservative |
| 8-Hydroxyquinoline sulfate | Antiperspirant, deodorant |
| Iodic acid | Astringent |
| Itraconazole | Antifungal |
| Kanamycin(s) | Antibacterial |
| Kermesic acid | Dye |
| Kojic acid | Flavor enhancer |
| Laccaic acid | Crimson dye |
| Lactic acid | Acidulant |
| Litmus | Indicator |
| L-Lysine L-glutamate | Flavor additive |
| Lyxoflavine | Feedstuff, growth-promoter |
| Maclurin | Dye |
| Malachite green | Dye |
| Maltol | Flavor enhancer |
| Maneb | Agricultural fungicide |
| Manganese acetate | Mordant |
| Meralein sodium | Topical anti-infective |

Plus a host of others, including a wide range of inorganic salts.

The list in Table II is by no means exhaustive as it can be readily determined for each type of particle whether it is capable of forming a hydrogen bond or a coordinate covalent bond. All or most of the particles are non-absorbent, or not superabsorbent polymers. Solubility of the particle in water and the binder can be easily ascertained, for example in standard chemical reference materials.

The particles listed in Table II have chemical properties that make them suitable for binding to fibers with the binders of the present invention. The listed particles are organic or inorganic compounds that are water soluble, yet have the capacity to hydrogen bond. Water solubility is preferably high. By water soluble it is meant that more than about 10 g of the particles will dissolve in 300 ml of water at 25° C.

The range of solubilities can extend, for example, from a lower limit of 10 g in 300 ml of water at 25° C., to an upper limit in which the particle is miscible in all proportions with water at 25° C. This high solubility allows the particles to dissolve when exposed to aqueous liquids such as urine, but the hydrogen bonding capacity allows them to adhere to the fibers in the presence of binder but in the absence of aqueous liquid during use by an end user after the manufacturing process is completed. While bound, the particles substantially retain a discrete particulate form instead of dissolving or fusing, at least until they are exposed to an aqueous liquid. More of the particles are discrete rather than agglomerated while bound in the absence of an aqueous liquid-. If the particles are exposed to fibers with binder in liquid form, for the particles to retain their particulate form, a binder is preferably selected so that the particles are sparingly soluble in the binder. By sparingly soluble it is meant that no more than about 5 g of particles dissolve in 300 ml of the binder at 25° C. Particles may be soluble in the binder as long as a sufficiently small amount of binder is used so that an effective portion of the particles remain in particulate form.

The amount of particles added to the fibers can vary widely, for example from 0.05 to 80 percent of the total weight of the fibrous material and particles. Antimicrobials, such as chlorhexidine or other nonabsorbent particles, are effective in very low amounts, such as 0.05 to 10 percent. Superabsorbent particles are preferably added in an amount of 3–70 percent, especially 20–40 percent by weight of the fibrous materials and particles. The particles may be combined to include more than one type of particle, for example superabsorbent and nonsuperabsorbent particles, or two types of superabsorbent particles. When two types of particles are used, the total weight of the particles will not exceed 80 percent of the total weight of the fibrous material and particles.

VI. Polymeric Binder Characteristics

The particles may be bound to the fibers by a polymeric binder, which may be water soluble, selected from a predetermined group of polymeric binders. The polymeric binders comprise binder molecules, wherein the binder molecules have at least one hydrogen bonding functionality or coordinate covalent bond forming functionality. The polymeric binder may comprise repeating units, wherein each repeating unit of the polymer preferably, but not necessarily, includes at least one hydrogen bonding functionality or coordinate covalent bond forming functionality. In accordance with the present invention, the predetermined groups of polymeric binders include the group of binders consisting of polyglycols [especially poly(propyleneglycol)], a polycarboxyic acid, a polycarboxylate, a poly(lactone) polyol, such as diols, a polyamide, a polyamine, a polysulfonic acid, a polysulfonate, and combinations thereof. Specific examples of some of these binders, without limitation, are as follows: polyglycols may include polypropylene glycol (PPG); poly(lactone) diols include poly(caprolactone) diol; polycarboxylic acid include polyacrylic acid (PAA); polyamides include polyacrylamide or polypeptides; polyamines include polyethylenimine and polyvinylpyridine; polysulfonic acids or polysulfonates include poly(sodium-4-styrenesulfonate) or poly(2-acrylamido-methyl-1-propanesulfonic acid; and copolymers thereof (for example a polypropylene glycol/polyethylene glycol copolymer). The polymeric binder typically has repeating units. The repeating unit may be the backbone of a compound, such as with a polypeptide, wherein the repeating polyamides occur in the peptide chain. The repeating unit also may refer to units other than backbones, for instance repeating acrylic-acid units. In such a case, the repeating units may be the same or different. The binder molecule has a functional group capable of forming a hydrogen bond or a coordinate covalent bond with particles, and a functional group capable of forming a hydrogen bond with the fibers.

As used herein, a polymer is a macromolecule formed by chemical union of 5 or more identical or different combining units (monomers). A polyamine is a polymer that contains amine functional groups and a polyamide is a polymer that contains amide functional groups. Each of the binders has a hydrogen bonding or a coordinate covalent bonding functionality. The functionality may be a hydroxyl, a carboxyl, a carboxylate, a sulfonic acid, a sulfonate, an amide, an ether, an amine or combinations thereof. These binders are capable of forming hydrogen bonds because they have a functional group that contains an electronegative element, such as oxygen or a nitrogen.

The polyglycol has repeating ether units with hydroxyl groups at the terminal ends of the molecule. The polycarboxylic acid, such as polyacrylic acid, has a repeating carboxyl group in which a hydrogen is bound to an electronegative oxygen, creating a dipole that leaves the hydrogen partially positively charged. The polyamide (such as a polypeptide) or polyamine has a repeating NR group in which a hydrogen may be bound to an electronegative nitrogen that also leaves the hydrogen partially positively charged. The hydrogen in both cases can then interact with an electronegative atom, particularly oxygen or nitrogen, on the particle or fiber to form a hydrogen bond that adheres the binder to the particle and fiber. The electronegative oxygen or nitrogen of the binder also can form a hydrogen bond with hydrogen atoms in the particle or fiber that have positive dipoles induced by electronegative atoms, such as oxygens or nitrogens, to which the hydrogen is attached. The polyamide also has a carbonyl group with an electronegative oxygen that can interact with hydrogen atoms in the particles or fibers. Thus, the polymeric binders can enhance the hydrogen bonding (a) between the fibers and binder; and (b) in the case of particles with hydrogen bonding functionalities, between the binder and the particles.

Alternatively, the polymeric binder may form a coordinate covalent bond with the particles and a hydrogen bond to the fibers. For example, the oxygen or nitrogen on the binder has an unbound pair of electrons that can be donated to an empty orbital in the particle to form a coordinate covalent bond. For example, one free pair of electrons on the oxygen or nitrogen can be donated to the empty p orbital of a boron-containing particle to form a coordinate covalent bond that adheres the particle to the binder. The fibers themselves contain functional groups that can form hydrogen bonds with the binder, and allow the binder to adhere to the fiber. Cellulosic and synthetic fibers, for example, may contain hydroxyl, carboxyl, carbonyl, amine, amide, ether and ester groups that will hydrogen bond with the hydroxyl, carboxylic acid, amide or amine groups of the binder. Hence, the polymeric binder will adhere the particle with a coordinate covalent bond and the fiber will adhere with a hydrogen bond.

In some preferred embodiments, the polymeric binder is bound to both the fibers and the particle by hydrogen bonds. A polypropylene glycol binder, for example, can be used to bind water-insoluble polyacrylate hydrogel particles to cellulosic fibers. The hydroxyl and ether groups on the glycol binder participate in hydrogen-bonding interactions with the hydroxyl groups on the cellulose fibers and the carboxyl groups on the polyacrylate hydrogel, as shown below:

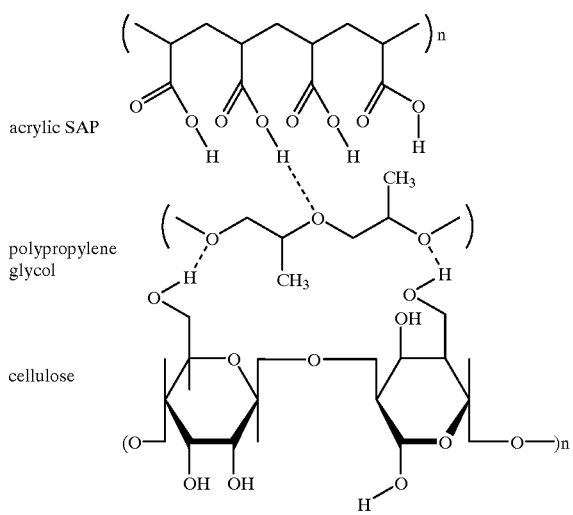

Alternatively, a polypropylene glycol (PPG) binder, for example, can be used to bind a water-soluble particle to cellulosic fibers. The hydroxyl and ether groups on the glycol binder participate in hydrogen bonding interactions with the hydroxyl groups on the cellulose fibers and appropriate functionalities on the water-soluble particle, as shown below:

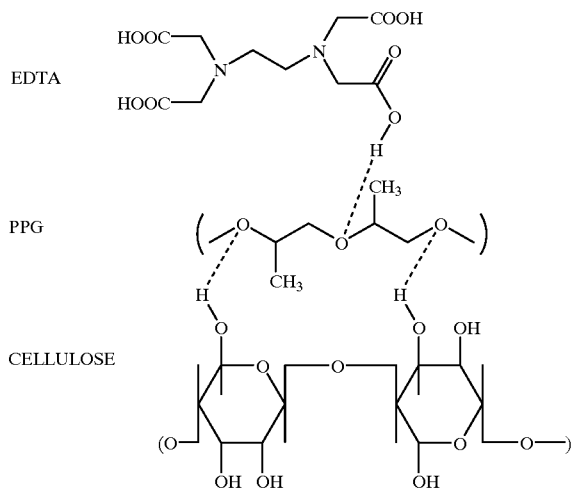

Hence, the binder will adhere both the particle and fiber with hydrogen bonds. The presence of a hydrogen-bonding functionality on each repeating unit of the polymeric binder has been found to increase the number of hydrogen bonding interactions per-unit-mass of polymer, which provides superior binding efficiency and diminishes separation of particles from the fibers. The repeating ether functionality on the glycol binder provides this efficiency in the examples diagrammed above. A repeating carboxyl group is the repeating functionality on polyacrylic acid, while repeating carbonyls and NR groups (wherein R is either an H or alkyl, preferably lower alkyl i.e., less than five carbon atoms, in a normal or iso configuration) of the amide linkages are the repeating functionalities on polyamides such as polypeptides. A repeating amine group is present on polyamines.

The polymeric organic binders of the present invention have been found to increase in binding efficiency as the length of the polymer increases, at least within the ranges of molecular weights that are reported in the examples below. This increase in binding efficiency is attributable to the increased number of hydrogen bonding or coordinate covalent bonding groups on the polymer with increasing molecular length. Each of the polymeric binders has a hydrogen bonding or coordinate covalent bonding functionality. If each repeating unit of the polymer has repeating functionalities, longer polymers provide more hydrogen bonding groups or coordinate covalent bonding groups that can participate in hydrogen bonding interactions or in coordinate covalent bonds.

Although the invention is not limited to polymeric binders of particular molecular weights, polymeric binders having a molecular weight greater than 500 grams/mole are preferred because they provide attractive physical properties, and the solid is less volatile as compared to low-molecular-weight polymeric binders. Polymeric binders with molecular weights greater than 4000 grams/mole are especially preferred because they have minimal volatility and are less likely to evaporate from the fibers. Low-molecular weight materials typically are more mobile than are the higher-molecular weight materials. Low-molecular weight materials can more easily move to the fiber-particle interface, and are more easily absorbed by the fiber where they are less available to bond the particles to the fibers. The higher molecular weight materials are less apt to be absorbed by the fibers, and are less volatile than the low-molecular weight materials. As a result, higher molecular weight polymeric binders, to a greater extent, remain on the surface of the particles where they are more available to bond particles to fibers. In some particular embodiments, polymers with molecular weights between 4000 and 8000 grams/mole have been used. Polymers with molecular weights above 8000 may be used, but such exceedingly high molecular weight polymers may decrease binding efficiency because of processing difficulties.

Certain polymeric binders have greater binding efficiency because their repeating functionality is a more efficient hydrogen bonding group. It has been found that repeating amide groups are more efficient than repeating carboxyl functionalities, which are more efficient than repeating hydroxyl functionalities, which in turn are more efficient than amine or ether functionalities. Hence, polymeric binders may be preferred that have repeating amine or ether functionalities, more preferably repeating hydroxyl functionalities, and even more preferably repeating carbonyl or carboxyl functionalities, and most preferably repeating amide functionalities. Binding may occur at any pH, but is suitably performed at a neutral pH of 5–8, preferably 6–8, to diminish acid hydrolysis of the resulting fibrous product. Suitable binders may be selected from the group consisting of polyglycols such as polyethylene glycol or polypropylene glycol, polycarboxylic acids such as polyacrylic acid, polyamides, polyamines, poly(lactone) diols, such as poly (caprolactone) diol and combinations or copolymers thereof.

The group consisting of polycarboxylic acids (such as acrylic acid), polyamides and polyamines has been found to have a especially good binding efficiency. Among polyamides, polypeptides are especially preferred.

VII. Non-Polymeric Binder Characteristics

The particles may be bound to the fibers by a non-polymeric organic binder selected from a predetermined group of binders that each have a volatility less than water. The vapor pressure of the binder may, for example, be less than 10 mm Hg at 25° C., and more preferably less than 1 mm Hg at 25° C. The non-polymeric binders comprise non-polymeric binder molecules wherein the molecules have at least one functional group that forms hydrogen bonds or coordinate covalent bonds with the particles. In accordance with the present invention, the predetermined group of non-polymeric binders may include a functional group selected from the group consisting of a carboxyl, a carboxylate, a carbonyl, a sulfonic acid, a sulfonate, a phosphate, a phosphoric acid, a hydroxyl, an amide, an amine, and combinations thereof (such as an amino acid or hydroxy acid) wherein each binder includes at least two such functionalities, and the two functionalities are the same or different. A requirement for the non-polymeric binder is that it have a plurality of functional groups that are capable of hydrogen bonding, or at least one group that can hydrogen bond and at least one group that can form coordinate covalent bonds. As used herein, the term "non-polymeric" refers to a monomer, dimer, trimer, tetramer, and oligomers, although some particular non-polymeric binders are monomeric and dimeric, preferably monomeric.

Particularly preferred non-polymeric organic binders are capable of forming five or six membered rings with a functional group on the surface of the particle. An example of such a binder is an amine or amino acid (for example, a primary amine or an amino acid such as glycine) which forms six-membered rings by forming hydrogen bonds:

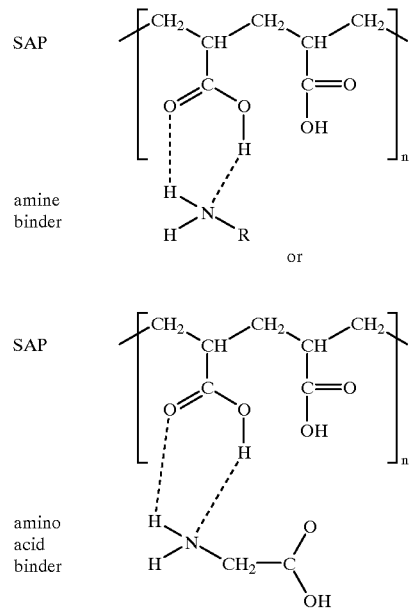

A six-membered ring also is formed by the hydroxyl groups of carboxylic acids, alcohols, and amino acids, for example:

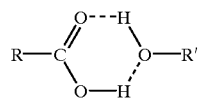

A five membered ring can be formed by the binder and the functionality on the surface of the particle, for example:

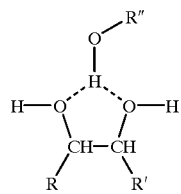

wherein the particle is a water-insoluble particle such as SAP and the binder is an alcohol, such as a polyol with hydroxyl groups on adjacent carbons, for example 2,3-butanediol. A binder that forms a five-membered ring can also be used with a water soluble particle, for example wherein the particle is EDTA and the binder is an alcohol, such as a polyol with hydroxyl groups on adjacent carbons, for example 2,3-butanediol.

Other alcohols that do not form a five-membered ring also can be used, for example alcohols that do not have hydroxyl groups on adjacent carbons. Examples of suitable alcohols include primary, secondary or tertiary alcohols.

Amino alcohol binders are alcohols that contain an amino group ($-NR_2$), and include binders such as ethanolamine (2-aminoethanol), and diglycolamine (2-(2-aminoethoxy)ethanol)). Non-polymeric polycarboxylic acids contain more than one carboxylic acid functional group, and include such binders as citric acid, propane tricarboxylic acid, maleic acid, butanetetracarboxylic acid, cyclopentanetetracarboxylic acid, benzene tetracarboxylic acid and tartaric acid. A polyol is an alcohol that contains a plurality of hydroxyl groups, and includes diols such as the glycols (dihydric alcohols), ethylene glycol, propylene glycol and trimethylene glycol; triols such as glycerin (1,2,3-propanetriol). Esters of hydroxyl-containing binders also may be used with mono- and di-esters of glycerin, such as monoglycerides and diglycerides, being especially preferred. In the case of the diglycerides, at least one of the esterifying acid moieties must also include a functional group that is capable of forming at least one hydrogen bond with the fibers, or at least one functional group capable of forming a hydrogen bond or a coordinate covalent bond with the particles. Examples of polyhydroxy or polycarboxylic acid compounds include tartaric acid or ascorbic acid (vitamin C):

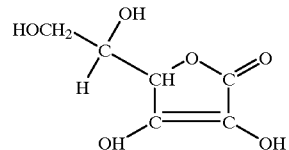

Vitamin C
(ascorbic acid)

Hydroxy acid binders are acids that contain a hydroxyl group, and include hydroxyacetic acid ($CH_2OHCOOH$) and lactic, tartaric, ascorbic, citric, and salicylic acid. Amino acid binders include any amino acid, such as glycine, alanine, valine, serine, threonine, cysteine, glutamic acid, lysine, or β alanine.

Sulfonic acid binders and sulfonates are compounds that contain a sulfonic acid group ($-SO_3H$) or a sulfonate ($-SO_3-$). Amino-sulfonic acids also can be used. one example of an amino-sulfonic acid binder suitable for the present invention is taurine, which is 2-aminoethanesulfonic acid. Non-polymeric polyamide binders are small molecules (for example, monomers or dimers) that have more than one amide group, such as oxamide, urea and biuret. Similarly, a non-polymeric polyamine binder is a non-polymeric molecule that has more than one amine group, such as ethylene diamine, EDTA or the amino acids asparagine and glutamine.

Although other non-polymeric organic binders are suitable in accordance with the discussion above, the non-polymeric organic binder is preferably selected from the fiber or particle can interact with hydrogen atoms on the binder that have positive dipoles, and partially positive hydrogen atoms on the fiber or particle can interact with electronegative atoms on the binder.

Several proposed hydrogen bonding interactions of two of the binders (glycine and 1,3-propanediol) with cellulose are shown below:

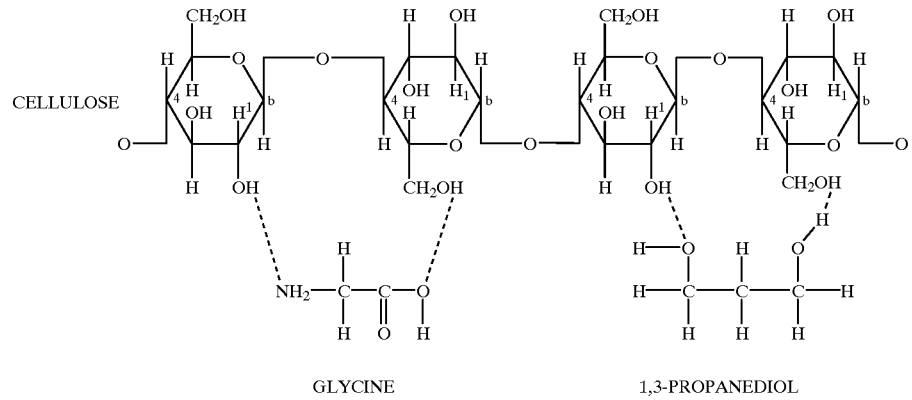

GLYCINE  1,3-PROPANEDIOL group consisting of glycerin, a glycerin monoester, a glycerin diester, glyoxal, ascorbic acid, urea, glycine, pentaerythritol, a monosaccharide, a disaccharide, citric acid, taurine, tartaric acid, dipropyleneglycol, urea derivatives, phosphate, phosphoric acid, a hydroxy acid, and combinations thereof. The non-polymeric binder also is most preferably selected from the group consisting of glycerin, a glycerin monoester, a glycerin diester, polyglycerin oligomers, urea and combinations thereof. The non-polymeric binders also preferably include functionalities selected from the group consisting of a carboxyl, a carboxylate, a carbonyl, a sulfonic acid, a sulfonate, a phosphate, a phosphoric acid, a hydroxyl, an amine, an amide, and combinations thereof (such as an amino acid or hydroxy acid). The non-polymeric binders must have at least two functionalities from such group, and the groups may be the same or different.

Each of the non-polymeric binders disclosed above is capable of forming hydrogen bonds because it has a functional group that contains electronegative atoms, particularly oxygens or nitrogens, or has electronegative groups, particularly groups containing oxygens or nitrogens, and that also include a hydrogen. The amino alcohol, amino acid, carboxylic acid, alcohol and hydroxy acid all have a hydroxyl group in which a hydrogen is bound to an electronegative oxygen, creating a dipole that leaves the hydrogen partially positively charged. The amino alcohol, amino acid, amide and amine all have an NR group in which a hydrogen may be bound to an electronegative nitrogen that also leaves the hydrogen partially positively charged. The partially positively charged hydrogen in both cases then can interact with an electronegative element, such as oxygen or nitrogen, on the particle or fiber to help adhere the binder to the particle and fiber. The polycarboxylic acid, hydroxy acid, amino acid and amide also have a carboxyl group with an electronegative oxygen that can interact with hydrogen atoms in the particles and fibers, or in intermediate molecules between the binder and particles or fibers. Similarly, electronegative atoms (such as oxygen or nitrogen) on the The hydrogen bonding interactions are shown as dotted lines. One such interaction is shown between the nitrogen of glycine and a hydrogen of an —OH on cellulose. A hydrogen bond with glycine is also shown between an oxygen of the —OH on glycine and the hydroxy hydrogen of an alcohol sidechain on cellulose. Hydrogen bonding interactions of the 1,3-propanediol are shown in dotted lines between an oxygen on an —OH group of the binder and a hydrogen of an —OH group on the cellulose molecule. Another hydrogen bond is also shown between a hydrogen on an —OH group of the glycol binder and an oxygen in an alcohol sidechain of the cellulose.

It also is possible for water or other hydrogen bonding molecules to be interposed between the fiber and binder, such that the fiber and binder are both hydrogen bonded to the water molecule.

Alternatively, an atom on the binder may have an unbound pair of electrons, such as a lone pair of electrons from an oxygen or nitrogen atom, that can be donated to an empty orbital of an acceptor atom in the particle to form a coordinate covalent bond. The free pair of electrons on the oxygen or nitrogen can be donated to the empty p, d or f orbital of a particle (for example a boron-containing particle) to form a coordinate covalent bond that adheres the particle to the binder. The fibers themselves do not normally contain functional groups that can act as electron acceptors in the formation of coordinate covalent bonds with the binders, but hydrogen bonding interactions allow the binder to adhere to the fiber. Cellulosic and synthetic fibers, for example, contain hydroxyl, carboxyl and ester groups that will hydrogen bond with the hydroxyl, carboxylic acid, amide, amine or other groups of the binder. Non-cellulosic or non-synthetic fibers that have these functionalities also can be used, for example silk, which has an amide linkage. Hence the binder will adhere the particle with a coordinate covalent bond and the fiber with a hydrogen bond.

In some preferred embodiments, the binder is bound to both the fibers and the particle by hydrogen bonds. A polyol binder, for example, can be used to bind polyacrylate hydrogel particles to cellulosic fibers. The hydroxyl groups on the polyol binder participate in hydrogen-bonding interactions with the hydroxyl groups on the cellulose fibers and the carboxyl groups on the polyacrylate hydrogel. Hence, the binder will adhere to both the particle and fiber with cellulose with hydrogen bonds, or water-soluble EDTA particles. Some of the possible hydrogen bonding interactions are shown as dashed lines. It is possible that other molecules (such as water molecules) also may participate in some of these bonds, for example, as an intermediary between the binder and particle or fiber.

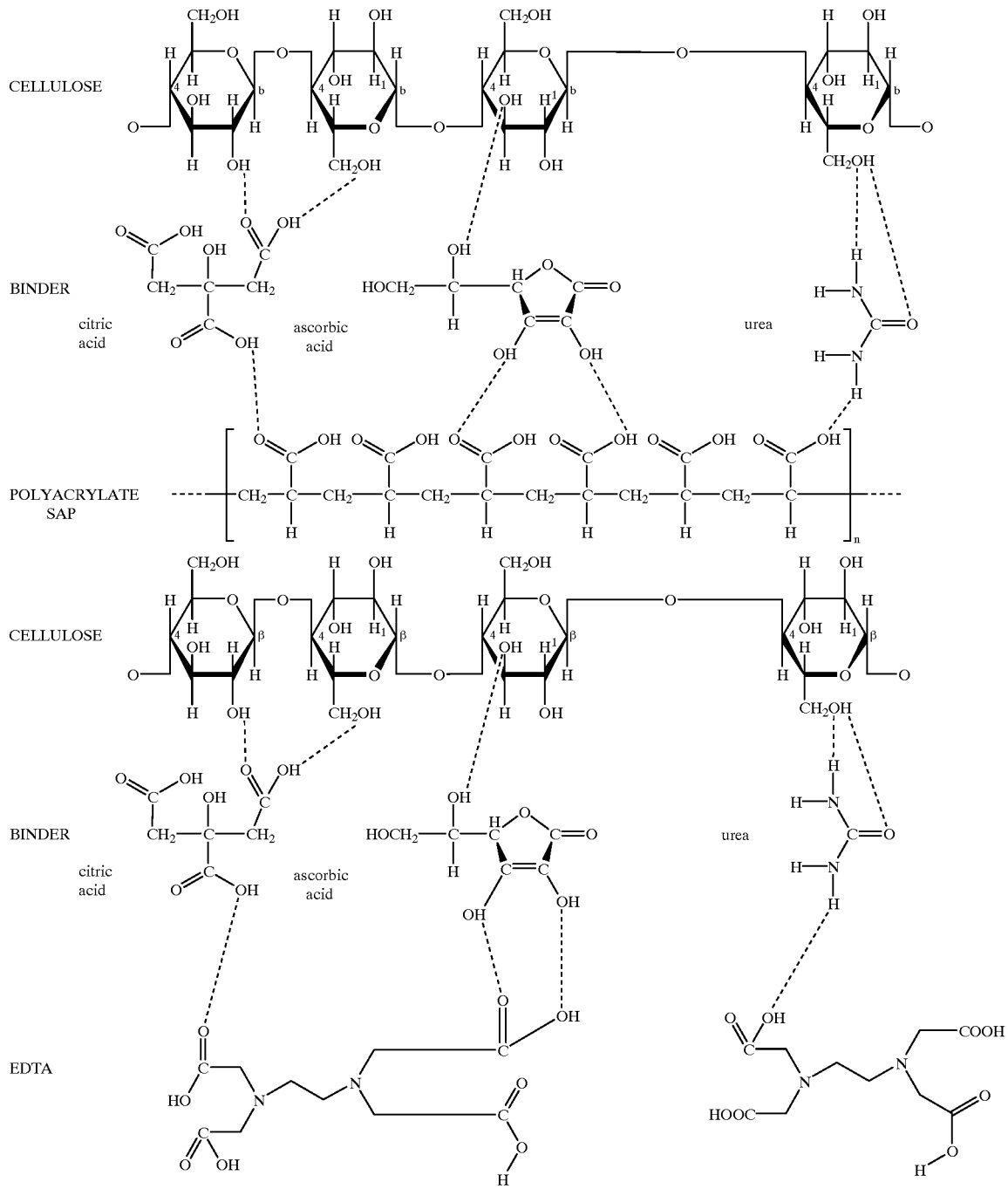

hydrogen bonds. These hydrogen bonds provide excellent binding efficiency and diminish separation of bound particles from the fibers.

A structural drawing is shown below in which citric acid, vitamin C and urea adhere water-insoluble SAP particles to Particularly efficient hydrogen bonding binders include those with carboxyl groups, such as ascorbic acid, or amide groups, such as urea. Hydroxyl groups are also very efficient binders. Amine and ether functionalities are less efficient binders.

Binders have functional groups that may be selected independently or in combination from the group consisting of a carboxyl, a carboxylate, a carbonyl, a hydroxyl, a sulfonic acid, a sulfonate, a phosphoric acid, a phosphate, an amide, an amine, and combinations thereof. These functional groups might be provided by the following exemplary chemical compounds: a carboxyl group could be provided by carboxylic acids, such as ascorbic acid; a carboxylate, which is an ionized carboxylic acid, could be provided by a material such as ascorbate; a carbonyl group can be provided by an aldehyde, such as ketone; a hydroxyl, such as an alcohol or a polyol, such as glycerol, or a mono- or diglyceride, which are esters of glycerol; an amide, such as a peptide; and an amine, which may be provided by an alkyl amine, such as ethylenimine wherein the binder has at least two of these functional groups, and each of the functional groups can be the same (for example, a polyol, polyaldehyde, polycarboxylic acid, polyamine or polyamide) or different (for example, an amino alcohol, hydroxyamide, carboxyamide, or amino acid). Functional groups also may be selected independently or in combination from the group consisting of carboxyl, an alcohol, an amide and an amine. An aldehyde may optionally be a member of each of these groups, particularly if it is oxidized to a carboxylic acid.

Combinations of the polymeric and non-polymeric binders, as well as with other binders, also may be used, providing that they are non-reactive. That is, providing that the binders do not react in a manner which prevents the binders from possessing the functional groups required to be present for binding in accordance with the present invention.

VIII. Process Advantages

The binders of the present invention also provide numerous process advantages. Binding of particles to the fibers can occur, for example, without external application of heat. Hence, if desired, particle binding may occur at ambient temperature. The present invention therefore is distinct from prior-art crosslinking processes in which elevated temperatures are required to covalently crosslink cellulose groups to one another. Moreover, the binders of the present invention have the advantage of being activatable by addition of a fluid, such as a liquid solvent (sometimes referred to herein as a activation liquid, one example of which is water). Hence, a liquid binder (which would include a solution of a solid or liquid binder, or a binder that has a melting point or softening point below room temperature) can be applied to a cellulose mat in the absence of the particles to be bound and the binder allowed to dry, for example until the fiber product reaches an equilibrium moisture content with the moisture in the ambient air. The binders then may be activated to bind the particles in place. Some of the binders (especially the liquid binders) diffuse throughout the fibers to reach an equilibrium distribution of the binder. Alternatively, the binder can be applied as a solid, for example as particles or a powder. At a later stage of processing, water or another activating fluid or liquid may be added to those portions of the mat where particulate binding is desired. The particles then may be added to the mat and adhered to those portions of the mat that have been moistened. Alternatively, the particles may be added to the mat prior to or simultaneously with activation of the binder.

The binders may be liquids at room temperature (such as glycerin), or liquid solutions of binders that are solids at room temperature (for example, an aqueous solution of glycine), or liquid hot melts of solid binders. Solid binders can be applied to the fibers as a supersaturated solution or the solid binder may be heated above its melting point and applied to the fibers. Upon solidifying the binder is deactivated. Solid binders may be added to fibers in particulate form, for example, by sprinkling binder particles on the fibers, provided they are fixed by the subsequent application of heat or liquid.

The binding reaction of the present invention can occur across a broad range of pH without requiring a catalyst. A suitable pH range without a catalyst is 1–14, but preferred ranges are 5–8 or 6–8 because such neutral pH ranges will produce fibrous products (such as cellulose products) that are less prone to damage by acid hydrolysis. A non-acidic pH (7 or greater) will provide an environment that inhibits formation of ester bonds, and promotes formation of the hydrogen bonds or coordinate covalent bonds that adhere the particles of the present invention to the fibers with the binder.

When water-insoluble particles are used, the moisture content of the fibers during the binding reaction is 0.5–50%, suitably 5–40%, or preferably 5–20% water by weight of the fibers, binder and particle. A moisture content greater than 20%, preferably 30%, or in the range 20–50%, or 30–50%, can be used even though such high moisture contents interfere with intermediate anhydride formation and inhibits formation of covalent bonds in the production of high-bulk crosslinked fibers. When water-soluble particles are used, the moisture content of the fibers during the binding reaction is 0.5–30%, suitably 5–20 25%, preferably 12–20%. Particles may be added to the fibers with the particles distributed throughout a fibrous product without being confined to a surface of the product. The particles can be distributed throughout the depth of a fiber product such as a mat or web.

The binder suitably is present in the treated product in an amount of at least 1 percent, and no more than 80 percent, by weight of the fibrous material ("percent by weight"). In especially preferred embodiments, the binder is present in an amount of 1–80, or more preferably, 1 to 40 or 1 to 25 percent by weight of the fibrous material. Below about 1 percent, when placed on the fiber, an insufficient amount of binder is present to achieve adequate binding. Using excessive amounts of binder can introduce unnecessary expense into the binding process. High percentages of binder can also cause processing problems because the binder material transfers to equipment surfaces. Therefore, it is often preferred to use no more binder than is required to bind the particles and fibers.

Thermoplastic binders also may be used to help bind fibers to each other and particles to fibers. The binder that has the hydrogen bonding or coordinate covalent bonding functionalities itself may be thermoplastic. The polymeric binders and some non-polymeric binders of the present invention have the advantage of being thermoplastic solids. Hence, fibers treated in accordance with the present invention can be thermobonded by elevating the fiber temperature above the softening temperature of the binder to soften the thermoplastic binder and thermoplastically bind the fibers to each other and the fibers to the particles. Alternatively, an auxiliary or second binder can be applied to the fibers as a solid at room temperature, and the temperature of the second binder elevated above its softening point to thermobond the fibers and particles. The auxiliary binder may be applied to the fibers either before or after the primary binder is applied, but before thermobonding.

The binders of the present invention may be used with fibers that have substantial intrafiber covalent crosslinks (such as HBA available from Weyerhaeuser) or fibers which are substantially free of intrafiber covalent crosslinking. Examples of individualized intrafiber crosslinked fibers are seen in European Patent Applications 440 472 A1 and 427 317 A2, which produce products that those publications describe as being substantially free of interfiber bonds. The fibers of the present invention do not need to be processed as in those European applications to eliminate interfiber bonds. Binders of the present invention can therefore be used with natural fibers that have substantial interfiber bonding, which are defined as fibers that have not been processed as in European Applications 440 472 A1 and 427 317 A2 to substantially eliminate interfiber bonds. Cellulose fibers that have not been so processed are substantially free of intrafiber bonds.

The fibrous product of the present method (with or without intrafiber crosslinking) may further be densified by external application of pressure. The densified product is compact and easily transported. And, when the particles are superabsorbent particles, the resulting fibrous product has superior properties as compared to nondensified products. The inventors have found that the binders of the present invention produce a product that can be easily densified. Easy densification is associated with the hydrogen bonds and coordinate covalent bonds formed between the binder and the particles and fibers. The fibers are particularly easily densified when at least 5% by weight of the fibers, particles and binder, more preferably 10%, are SAP particles adhered to the fibers.

In accordance with this invention, the binders may be applied to fibers before, subsequent, or simultaneously with addition of the particles. Simultaneous addition can be accomplished by two separate streams of particles and binder that are simultaneously directed at a fibrous substrate, or alternatively merged immediately or some time prior to impacting against the substrate. Without limiting the invention, it appears that the addition of small amounts of moisture to the particles may help bind superabsorbent particles and perhaps other types of particles to the fibers. For example, exposing the particles to air at 65 percent humidity as they are delivered to binder containing fibers has been found to enhance the particle bonding.

Binding may be performed under conditions that favor formation of hydrogen bonds or coordinate covalent bonds, and discourage formation of covalent bonds. Conditions that favor covalent bonds are those disclosed in U.S. Pat. No. 4,412,036 and U.S. Pat. No. 4,467,012 wherein particle and binder would be laminated between tissue layers under high temperature and pressure to form laminated adherent tissue layers. That patent teaches that minimal adhesion occurs at 200 pli (pounds per linear inch, as in a calendar press) if no external heat is supplied, but adhesion improves as the reaction temperature increases. Improved adhesion of the tissue layers occurs because of enhanced covalent bonding as the temperature increases.

Conditions that favor covalent bond formation are also shown in European Patent Applications 440 472 A1; 427 317 A2; 427 316 A2; and 429 112 A2. These European publications use polycarboxylic acid crosslinkers, and require elevated temperatures (for example above 145° C.) and acidic conditions (pH less than 7) to promote formation of intrafiber covalent ester bonds and inhibit reversion of the ester bonds. The present invention, in contrast, can form hydrogen or coordinate covalent bonds below 145° C., below 100° C., and even at room temperature. The binders of the present invention also can bind particles to fibers under neutral or alkaline conditions, i.e., at a pH above 7, but preferably at a pH of 5–8 or 7–8. Fibers that have high bulk from intrafiber covalent crosslinks are prepared by individualizing the fibers (for example, in a fiberizer) and curing them at an elevated temperature (above 150° C.). Initial application of the binder on such high-bulk fibers preferably occurs after the curing step, particularly if the binder is capable of functioning as a crosslinking material. The specific types of binders disclosed herein that also can crosslink are polyols, polyaldehydes, polycarboxylic acids, and polyamines (polymeric or nonpolymeric binders with more than one amine group). If such binders are present during curing, the binder will be consumed during the curing step to form covalently crosslinked bonds. When this occurs, the binder is no longer available for hydrogen bonding or coordinate covalent bonding, and particle binding to fibers is ineffective.

The intrafiber covalent bond forming processes described in the above European publications require formation of an anhydride that then reacts with a hydroxy group on cellulose to form a covalent ester bond. The presence of more than about 20% water by weight in the fibers is believed to interfere with the formation of the anhydride and inhibits covalent bond formation. Hence, in processes that use polycarboxylic acids, polyols and polyamines (which includes both polymeric and nonpolymeric amines having more than one amine group) as binders in the present invention, the fibers should contain at least 20% water (or 20–50% water) by weight if the particles and binder are present in the fibers when curing occurs. The water inhibits covalent bond formation, and prevents all of the binder from being used to form covalent intrafiber crosslinks. Hence, some of the binder remains available to form the non-covalent bonds with the particles and produce ease of densification in fiber products made by the process of the present invention.

The present invention, in contrast, produces a product under conditions that favor formation of hydrogen or coordinate covalent bonds. Hence, the particles can be bound to the fibers in the absence of the external application of heat or pressure. Particles also may be bound and the resulting fiber product densified, for example at less than 200 pli (about 8000 psi) with SAP, or less than 100 pli (about 4000 psi) with SAP, in the absence of external application of heat to produce a product in which a substantial portion of the particles are bound by non-covalent bonds (hydrogen or coordinate covalent bonds). A substantial portion of particles bound by non-covalent bonds means at least half of the bonds binding particles to fibers are other than covalent bonds, for example, hydrogen or coordinate covalent bonds.

In yet other examples, particles may be bound in the absence of external application of pressure, but at elevated temperatures.

In particularly preferred embodiments, the particles are substantially entirely bound to the fibers non-covalently.

IX. Binding Examples for Polymeric Binders and Water Insoluble Particles

Several examples are provided below to illustrate using the polymeric binders within the present invention to attach superabsorbent particles to southern bleached kraft pulp.

EXAMPLE 1

A 321 gram amount of NB-416 southern bleached kraft fluff obtained from Weyerhaeuser Company may be air-entrained in a blender-like mixing device and 100 grams of poly(caprolactone) diol (average molecular weight 2000, supplied by Aldrich Chemical Company of Milwaukee, Wis.) dissolved in 100 ml of deionized water may be sprayed onto the fluff as a binder. Then 435 grams of starch graft polyacrylate hydrogel fines (IM 1000F; supplied by Hoechst-Celanese of Portsmouth, Va.) may be added and mixed. The product may then be removed from the blender, and spread out in a fume hood to dry overnight. The resulting product may then be airlaid on a small airlay line, from M & J Machines (of Horsens, Denmark) and thermobonded at 140° C. for one minute to produce a web containing 40% superabsorbent particles (SAP) attached to the individualized fibers. This binder has a low melting point, hence raising the temperature to 140° C. melted the binder and allows it to flow over the fibers and particles to enhance hydrogen bonding interactions, thereby further binding the fibers and particles. This is an example of activating a solid binder by heating it, without liquid addition. A polypropylene glycol/polyethylene glycol copolymer binder would also behave in this manner.

EXAMPLE 2

A 321 gram amount of southern kraft fluff was air-entrained in a blender-like mixing device and 154 grams of a 65% solution of polyacrylic acid (average molecular weight=2,000; supplied by Aldrich Chemical Company of Milwaukee, Wis.) diluted with 100 ml of deionized water was sprayed onto the fluff. Then 435 grams of polyacrylate hydrogel (FAVOR 800 supplied by Stockhausen of Greensboro, N.C.) was added into the mixing device and mixed with the fluff and polyacrylic acid binder. The product was removed and spread out to dry and then fed to a hammermill with a three-eighths inch round hole screen and shunted to a small airlay line to produce a web containing 40% SAP attached to the individualized fibers.

EXAMPLE 3

A 321 gram amount of southern bleached kraft fluff is air-entrained in a blender-like mixing device and 100 grams of polyglycine (molecular weight=5,000–15,000; supplied as a dry powder by Sigma Chemical Company of St. Louis, Mo.) diluted with 100 ml of deionized water is sprayed onto the fluff. Then 435 grams of starch graft polyacrylate hydrogel fines (IM 1000F; supplied by Hoechst-Celanese of Portsmouth, Virginia) is added and mixed. The product is removed and spread out in a fume hood to dry overnight. The resulting product is fed into a Fitz hammermill with a three-eighths inch round hole screen and shunted to a small M & J airlay line to produce a web containing 40% SAP attached to the fibers.

EXAMPLE 4

A 321 gram amount of southern bleached kraft fluff is air-entrained in a blender-like mixing device and 200 grams of a 50% solution of polyethyleneimine (molecular weight= 50,000–100,000; supplied by ICN Biomedicals, Inc. of Costa Mesa, Calif.), or polyvinyl pyridine is sprayed on the fluff. Then 435 grams of starch graft polyacrylate hydrogel fines (IM 1000F; supplied by Hoechst-Celanese of Portsmouth, Va.) is added and mixed. The product is removed and spread out in a fume hood to dry overnight. The resulting product is fed into a Fitz hammermill with a three-eighths inch round hole screen and shunted to a small M & J airlay line to produce a web containing 40% SAP attached to the fibers.

The classes of polymeric binders that encompass those described in Examples 1–4 are especially preferred over other multiple hydrogen bonding functionality polymers for a number of reasons. One important reason is that their functionalities produce very strong, effective hydrogen bonding. Other important reasons include their relative lack of activity (as compared with polyaldehydes or polyisocyanates) and their low toxicity (again, as compared with polyaldehydes or polyisocyanates).

EXAMPLE 5

As previously described, repetition of a hydrogen bonding group on each repeating unit of a polymer has been found to produce a binder that provides superior binding of particles to fibers, as compared to polymeric binders in which the hydrogen bonding functionality is not present on all the repeating units. This example shows the difference in binding efficiency between a 20% carboxylated polymer and a 100% carboxylated polymer. A bound sample was prepared as in Example 1 using a 20% carboxylated ethylene acrylic acid copolymer and a 100% carboxylated PAA. A sample of each was subjected to the same mechanical agitation (to simulate machine processing required to make a web), screened through a descending series of sieves to remove unattached SAP, and subjected to an absorbent capacity test (less attached SAP would result in a lower absorbent capacity). The result of the test was measured by weighing the unabsorbed liquid (0.9% saline) from a standardized result. A lower number indicates more liquid absorbed, which corresponds to a higher absorbent capacity.

A sample of the 20% carboxylated polymer (15% of the total mix) gave a beaker test result of 19.5 grams. A similar sample of polypropylene glycol would give a result of about 20.0 grams. However, the hydrogen bonding functionality of PPG is not as efficient as the carboxyl functionality of PAA. A similar sample of polyacrylic acid (100% carboxyl functionality of PAA) gave a result of 11.3 grams. A comparison of the 20% and 100% carboxylated polymers shows a substantial increase in SAP binding efficiency, as measured by an increase in absorbency of the product.

X. Non-Polymeric Binding Examples

Several examples are provided below to illustrate the use of several non-polymeric organic binders of the present invention to attach superabsorbent particles to southern bleached kraft pulp. Several examples of binder activation and activation also are provided.

EXAMPLE 6

A 3171 gram amount of southern bleached kraft fluff was air-entrained in a blender-like mixing device and 1000 grams of glycerin (96%, USP; supplied by Dow Chemical Co. of Midland, Mich.) diluted with 300 ml of deionized water was sprayed onto the fluff. Then 4348 grams of starch graft polyacrylate hydrogel fines (IM 1000F; supplied by Hoechst-Celanese of Portsmouth, Va.) were added to the mixing device and mixed with the fluff and binder. The material was then shunted into a flash tube dryer at 142° F., blown into a cyclone and fed into a Danweb airlay machine to form a web containing bound 40% IM 1000F that is substantially immobile in the web because the particles are bound to the fibers instead of mechanically entrapped by the matrix. Glycerin is advantageous because it tends to penetrate the fibers and soften them in addition to binding the particles to the fibers. However, over time less glycerin is available at the surface of the fibers for use in binding particles in the event the glycerin/fiber material is stored for long periods prior to use in adhering particles (e.g. if activation is delayed for several weeks or more). This can be compensated for in part by using higher percentages of glycerin on the fibers. Also, monoglyceride and diglyceride binders do not penetrate as readily into the fibers and therefore can be stored longer before activation to adhere particles.

EXAMPLE 7

A 900 gram amount of southern bleached kraft fluff pulp sheet was sprayed with a 50% solution of glycine (supplied as a dry powder by Aldrich of Milwaukee, Wis.) so that the moisture content was 17–21% as the sheet was fed into a Fitz hammermill fitted with a three eighths inch hole screen. Starch graft polyacrylate hydrogel fines (IM 1000F; supplied by Hoechst-Celanese of Portsmouth, Va.) were simultaneously added to the mill by a screw feed device, mixed with the fluff, shunted to an M & J airlay forming machine and airlaid to form a web. The web that resulted contained 20% SAP attached to the fibers substantially uniformly throughout the web without being confined to a surface of the web.

EXAMPLE 8

A 900 gram amount of southern bleached kraft fluff pulp sheet was sprayed with a 50% solution of pentaerythritol (supplied by Aldrich of Milwaukee, Wis.) so that the moisture content was 17–21% as the sheet was fed into a Fitz hammermill fitted with a three-eighths-inch hole screen. Starch graft polyacrylate hydrogel fines (IM 1000F; supplied by Hoechst-Celanese of Portsmouth, Va.) were simultaneously added to the mill by a screw feed device, mixed with the fluff, shunted to an M & J airlay forming machine and airlaid to form a web. The web that resulted contained 20% SAP attached to the fibers.

EXAMPLE 9

A 900-gram amount of southern bleached kraft fluff pulp sheet was fed into a Fitz hammermill fitted with a three-eighths-inch hole screen. The sheet was defiberized, shunted to an M & J airlay line, and airlaid into a web. As the web emerged, target zones of the web were misted with a 50% solution of lactose to raise the moisture content to 17–21%. Five gram aliquots of starch graft polyacrylate hydrogel fines (IM 1000F; supplied by Hoechst-Celanese of Portsmouth, Va.) were subsequently sifted onto the target zones. The web that resulted contained target zones with 5 grams of SAP attached to the fibers of each target zone. Portions of the web that were not targeted for lactose application did not adhere the particles well. This is an example of applying the binder to a target zone so that SAP primarily adheres to the target areas where the binder was applied. Target-zone application of SAP can be advantageous because it reduces the cost of the product to provide SAP only in areas of a product where the SAP is needed, for example, the crotch area of a diaper. Placement of SAP in the area where a liquid insult is expected also decreases the necessity for wicking liquid to a SAP impregnated region. This is an advantage because the requirement for wicking can increase liquid leakage in an absorbent product such as a diaper.

EXAMPLE 10

A 321 gram amount of southern bleached kraft fluff was air-entrained in a blender-like mixing device and 100 grams of glycerin (96%, USP; supplied by Dow of Midland, Mich.) diluted with 30 ml of deionized water were sprayed onto the fluff. 71 grams of Abscents (an odor absorbing zeolite supplied by UOP of Tarrytown, N.Y.) was then added and mixed in the mixing device with the fibers and glycerin for 15 seconds until a homogenous mixture was achieved. The material was then spread out in a fume hood overnight to dry, airlaid into a web and tested for particulate retention by an ash test. The pad so produced contained 7% particulate. The original addition amount should have produced 15%, hence 50% particle retention was observed. This compares favorably to particulate retention with latex binders under similar conditions in which only about 3% of particles are retained.

XI. Binding Examples for Water-Soluble Particles

Several examples are provided below to illustrate using binders of the present invention to attach water-soluble particles to southern bleached kraft pulp.

EXAMPLE 11

A 321 gram amount of NB-416 southern bleached kraft fluff obtained from Weyerhaeuser Company (Tacoma, Wash.) was air-entrained in a blender-like mixing device and 50 grams of glycerin (supplied by Dow Chemicals of Midland, Mich.) were sprayed onto the fluff. Then 288 grams of disodium ethylenediamine tetraacetic acid (EDTA) (supplied by Mallinkrodt Chemical Works of St. Louis, Mo.) were added and mixed in the device. The blender was stopped, the product was vacuumed out, and spread out in a fume hood to dry overnight. The resulting product was examined by scanning electron microscope and revealed disodium EDTA particles attached to fibers.

EXAMPLE 12

A 321 gram amount of HBA pulp (a crosslinked high bulk fiber available from Weyerhaeuser Company, Tacoma Wash.) was air-entrained in a blender-like mixing device and 50 grams of glycerin (supplied by Dow Chemical of Midland, Mich.) were sprayed onto the fluff. Then 288 grams of sodium bicarbonate (supplied by J. T. Baker Chemical Co. of Phillipsburg, N.J.) were added and mixed in the device. The blender was stopped, the product was vacuumed out, and spread out in a fume hood to dry overnight. The resulting product was examined by scanning electron microscope (SEM) and revealed fibers with attached sodium bicarbonate particles.

EXAMPLE 13

An NB 416 pulp sheet (southern bleached kraft available from Weyerhaeuser Company of Tacoma, Wash.) was treated with glycerin on a roll coater so that the product contained 10% glycerin by weight. That pulp sheet was fed into a hammermill and ground while simultaneously adding a polyacrylate hydrogel (IM 3900, supplied by Hoechst Celanese of Portsmouth, Va.) and ethylenediamine tetraacetic acid (EDTA) to the mill at rates such that the product contained 54% treated fiber, 42% IM 3900, and 4% EDTA. That mixture was shunted to an airlay device from M & J Machines (of Horsens, Denmark) and airlaid into a continuous web. The resulting product was examined by scanning electron microscope and revealed fibers with attached polyacrylate hydrogel and EDTA particles.

EXAMPLE 14

A procedure similar to the one described in Example 13 was performed using KittyHawk pulp (a thermobondable blend of southern bleached kraft and polyethylene fibers available from Weyerhaeuser Company of Tacoma, Wash.). The resulting product was thermobonded by passing the web through a through-air oven at 140° C. for 0.5 minutes. The resulting product was examined by scanning electron microscope, and revealed fibers with attached polyacrylate hydrogel and EDTA particles.

EXAMPLE 15

Figure 14:
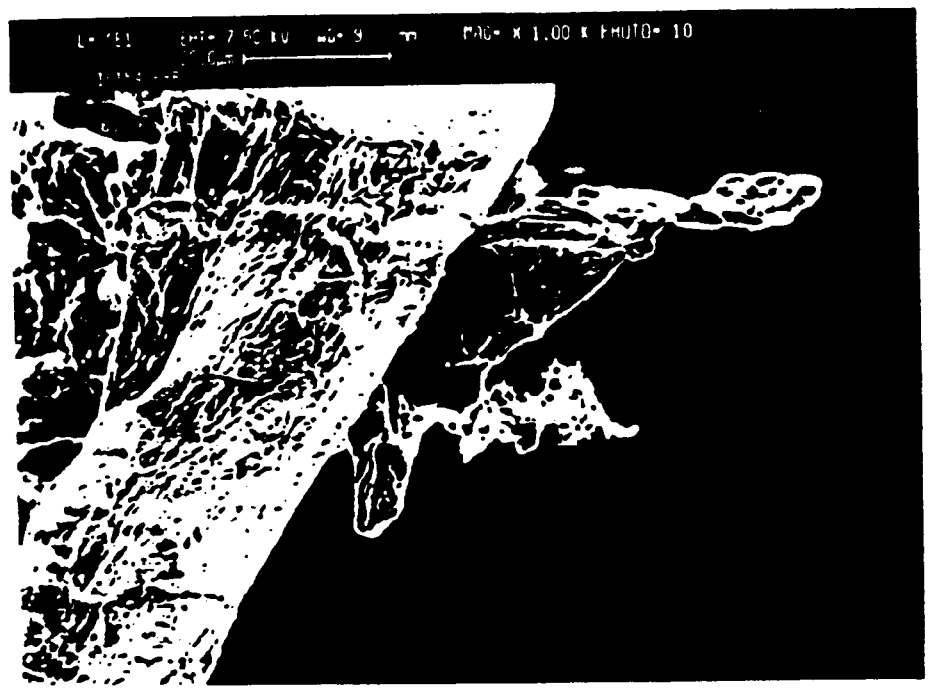
FIG. 14 is a photomicrograph of oxalic acid particles bound to a fiber with a glycerin binder.

In this example, oxalic acid is bound to the fibers by the binders of the present invention. A pulp sheet with 10% binder was prepared as in Example 13. The pulp sheet was conditioned at 90% relative humidity for 4 hours, then the sheet was fiberized in a Waring blender. Particles of oxalic acid were then added to the blender and blending continued. The product was dried and an SEM obtained, which is shown in FIG. 14. The feathery particle of oxalic acid is shown near the center of the photograph bound to the cellulose fiber by the glycerin.

EXAMPLE 16

Figure 15:
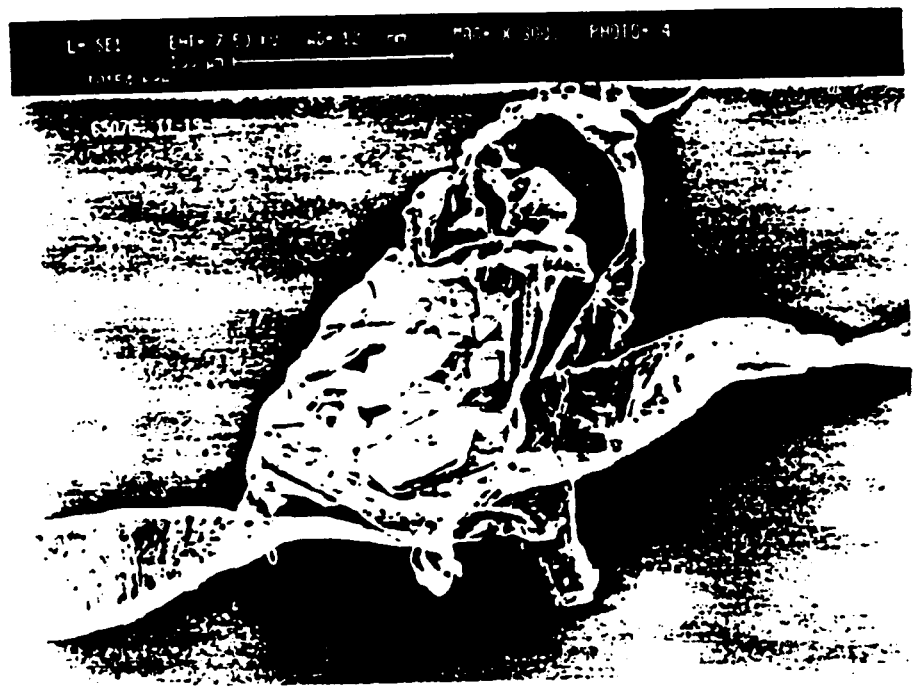
FIG. 15 is a photomicrograph of aluminum sulfate (alum) bound to a fiber with a glycerin binder.

Fibers were prepared as in Example 15, except aluminum sulfate (alum) was substituted for oxalic acid. The SEM of alum bound to the fibers is shown in FIG. 15.

EXAMPLE 17

A mixture of binders also may be used to bind particles to the fibers. Fibers may be supplied as in Example 11, but the 50 grams of glycerin would be substituted with a mixture of urea and glycerin. A 40/60 mixture (by weight) of urea and glycerin is mixed by dissolving urea in the glycerin, and heating the solution to 70–80° C. The heated binder mixture is then applied to bind the particles to the fibers as in Example 11. The urea/glycerin mixture provides several advantages over the use of glycerin alone. Urea lowers the cost of the binder, while glycerin softens the fibers. The mixture also provides manufacturing advantages.

In other embodiments urea alone as well as the other binders of the type specified in the foregoing detailed description of the invention and combinations thereof may be used as the binder.

XII. Product Characteristics

The following examples illustrate how SAP retention, pad integrity, wettability, bulk and liquid retention are affected by the glycerin binder of the present invention.

EXAMPLE 18

Superabsorbent particles were bound to cellulose fibers with a glycerin binder, as described in Example 6 above. For purposes of comparison, superabsorbent particles were bound to a separate sample of cellulose fibers using a polyvinyl acetate (PVAc) binder that was about 3% carboxylated, that is only about 3% of the PVA monomers were carboxylated. Binding was performed as in Example 6, but PVAc was substituted for glycerin. A 100-gram sample of the glycerin and PVAc treated fluff with attached SAP was fed into a fan that was connected by a hose to a small cyclone mounted on top of a material containment box. This was done in an effort to simulate forces of mechanical agitation the fluff would encounter during the airlay process. After collection in the material containment device, fiber with attached SAP was removed and weighed. A five gram sample of the fiber with attached SAP was then placed in a column of sieves with decreasing mesh sizes and subjected to a shaking and thumping action for ten minutes in order to further dislodge any poorly attached SAP.

Unattached or poorly attached SAP sifted through screens having a range of 5–60 mesh, while the fiber with well attached SAP remained on the 5 mesh screen.

A 2.00 gram sample of the fibers that remained near the top of the sieve column was then placed in a 75 ml sample of 0.9% saline for exactly one minute. After that minute, the liquid that was not absorbed was poured off into a separate, tared beaker and weighed. The relative amounts of liquid absorbed is indicative of the amounts of SAP bound to the fiber. Fiber retaining higher amounts of SAP tend to absorb more liquid and give a smaller amount of liquid not absorbed.

These results are shown in Table III:

TABLE III

Glycerin Binder
Comparing SAP Retention with Glycerin and PVAc Binders

| Binder | Beaker result |
|---|---|
| 40-504 (PVAc) | 22.8 g |
| 3666H (PVAc) | 22.0 g |
| Glycerin | 5.5 g |

Table III illustrates that the glycerin binder provides a product that has an absorbency increase of 400% compared to the PVAc binder. A substantial portion of this improvement is believed to be due to better adhesion between the fibers and SAP, such that the particles are not dislodged from the fibers.

EXAMPLE 19

Pad integrity was compared in fibrous products that used no binder and a glycerin binder at 7% and 11% by weight. Each of these binders was used to bind SAP to fibers as in Example 6, and properties of the pad were measured and are shown in Table IV:

TABLE IV

| | Tensile Results | | |
|---|---|---|---|
| Sample | Basis Weight | Density | Tensile Index |
| Pad integrity (low density): | | | |
| NB-416 (control) | 464 gsm | 0.12 g/cc | 0.257 Nm/g |
| NB-416/7% Glycerin | 437.6 gsm | 0.126 g/cc | 0.288 Nm/g |
| NB-416/11% Glycerin | 402.5 gsm | 0.135 g/cc | 0.538 Nm/g |
| Pad Integrity (high density): | | | |
| NB-416 (control | 482.1 gsm | 0.218 g/cc | 0.475 Nm/g |
| NB-416/7% Glycerin | 460.7 gsm | 0.219 g/cc | 0.882 Nm/g |
| NB-416/11% Glycerin | 421.6 gsm | 0.248 g/cc | 1.536 Nm/g |

The glycerin binder in this example produced a product that had a higher tensile index than an untreated product. The increased tensile strength was especially enhanced in the densified (high density) product, and particularly when at least 11% of the binder was used.

EXAMPLE 20

The effect of binders on the wettability and bulk of fibers was tested using the following fibers: NB-316 (a standard southern bleached kraft pulp with no binder); GNB as used herein is an NB pulp (a standard southern bleached kraft pulp) with 25% glycerin (entrained and sprayed); HBA pulp (a high bulk intra-fiber crosslinked fiber available from the Weyerhaeuser Company that contains intrafiber covalent crosslinks); and GHBA as used herein is HBA fibers treated with a glycerin binder in amounts of 12.5% and 25% by weight. Results are given in Tables V and VI.

FAQ time was determined by airlaying a specific quantity (4.00 grams) of the fluff to be tested into a clear plastic tube that was fitted with a screen at one end. The fluff and tube were then placed into a well in the test device and a metal plunger was lowered onto the fluff and the pad's bulk calculated. Water then flowed from underneath the pad, passed through the screen and wicked up through the pad. Absorbency time was measured from when the liquid makes contact with the bottom screen until the water completes an electrical circuit by contacting the foot of the plunger resting on top of the pad. Lower absorbency times indicate better absorbency. Since the absorption of the liquid by the pad was accompanied with some collapse of the pad's structure, the bulk of the wet pad was then recalculated. The amount of liquid absorbed was then measured and a gram-per-gram capacity for the material was calculated.

Table V gives FAQ time as a measure of wettability. A lower FAQ time indicates a product that is more absorbent and wicks faster. Table VI gives wet bulk of fibers and the adjusted bulk of the fibers. The adjusted bulk is a calculated number obtained by dividing the bulk by the actual percent of pulp in the sample.

TABLE V

| Wettability | |
|---|---|
| Fiber | FAQ time |
| NB-316 | 3.0 sec |
| GNB 25% | 3.2 sec |
| HBA | 13.5 sec |
| GHBA 12.5% | 4.5 sec |
| GHBA 25% | 0.4 sec |

TABLE VI

| | Bulk | |
|---|---|---|
| Fiber | Wet Bulk | Adjusted Bulk |
| NB-316 | 12.7 cc/g | 12.7 cc/g |
| GNB 25% | 10.9 cc/g | 14.5 cc/g |
| HBA | 19.4 cc/g | 19.4 cc/g |
| GHBA 12.5% | 16.1 cc/g | 18.4 cc/g |
| GHBA 25% | 14.9 cc/g | 19.9 cc/g |

The low FAQ times (Table V) in the glycerin-treated fibers (GNB, GHBA) show that wettability is as good as the untreated fiber (NB-316). The GHBA 25% had significantly better wettability than untreated HBA pulp. Bulk of glycerin treated fibers (Table VI) was not significantly decreased or changed at all levels of glycerin binder on a fiber to fiber comparison basis.

EXAMPLE 21

Liquid retention of bound fibers was determined and compared to fibers in which no binder was added. NB-316 is a pulp sheet available from Weyerhaeuser company in which no binder is used. HBA pulp is described in Example 20. HBA/Gly SAP was an HBA pulp fiber that was bound with glycerin (12% binder, 48% fiber) and which contained 40% SAP particles. NB-316/Gly SAP is NB-316 fibers to which glycerin and SAP fibers were added.

The procedure for determining liquid retention was to weigh triplicate small portions (near 0.2 grams) of sdmples to the nearest 0.0001 gram and then heat-seal the small portions inside an envelope of a heat-sealable, nonwoven tea bag. The samples were then immersed in an excess of 0.9% saline for thirty minutes, then drained by suspending them from a clip for fifteen minutes. The samples were weighed to determine the amount of liquid absorbed. The grams of liquid absorbed per gram of sample were calculated and the samples were spun in a centrifuge for one minute. The samples were then reweighed and a percent-liquid-retention was calculated.

Results are shown in the following Table VII:

TABLE VII

| Liquid Retention (after centrifuge) | |
|---|---|
| Fiber/Binder | % Retention |
| NB-316/none | less than 1% |
| HBA/none | less than 1% |
| HBA/Gly SAP | 23% |
| NB-316/Gly SAP | 31.5% |

The results in Table VII illustrate that fibers that have SAP bound to them retain liquid well, while fibers without SAP retain liquid poorly. The glycerin binders provided excellent adherence of SAP to the fibers.

XIII. Auxiliary Binder

As previously described, an auxiliary binder or additional binder or binders can be used in addition to the non-polymeric or polymeric binders or combinations thereof in accordance with the present invention. However, the additional binder(s) is selected to not react with the binder or binder combination of the present invention in a manner which prevents this latter binder from having the required functionality. Thus, the preferred auxiliary binders are non-reactive in this way. In addition, polymeric and non-polymeric binders of the invention may be combined with one another and with other binders as long as they do not react to block the desired functionality.

EXAMPLE 22

A 321 gram amount of a southern bleached kraft fiber (NB-416, supplied by Weyerhaeuser) was air entrained in a blenderlike mixing device and sprayed with 212.8 grams of a polyvinylacetate latex (PN-3666H, supplied by H B Fuller of Minneapolis, Minn.). While still mixing, 438 grams of a water swellable polyacrylate hydrogel (Favorsab 800, supplied by Stockhausen of Greensboro, N.C.) was added and the resulting mixture was then sprayed with 100 grams of a 50% solution of glycerin (supplied by Dow of Midland, Mich.). The blender was then stopped and the mixture was vacuumed from the blender and placed in a fume hood to air dry overnight. The dried product was then airlaid into a 6" diameter pad in a laboratory padformer, pressed to a density of approximately 0.077 g/cc, and thermobonded at 140° C. for thirty seconds. The resulting pads had 40% bound SAP and improved tensile strength as compared to untreated fluff with SAP and as also compared to binder treated fluff with SAP without the auxiliary binder.

Tensile strength was highest with polyvinylacetate alone, followed by a combination of polyvinylacetate and glycerin, then glycerin alone. Lowest tensile strength was seen with no binder at all.

EXAMPLE 23

Binders of the present invention may be used to bind particles to pulp fibers that contain synthetic thermobonding fibers. In this example, Kittyhawk pulp (available from Weyerhaeuser Company) is a mixture of NB316 southern bleached kraft and 22% polyethylene thermoplastic binder fibers. The Kittyhawk pulp is used to produce a pulp web, with SAP bound to the fibers as described in Example 3. The web with adhered SAP is then passed through a thermobonder to soften the polyethylene fibers and fuse the fibers of the web to each other to increase web strength.

XIV. Spectroscopic Evaluations

Spectroscopic measurements were made of the fiber products made according to the present invention. The results of the NMR and IR studies are presented below.

A. NMR Analysis

EXAMPLE 24

Solid sample $^{13}$C NMR spectra were obtained on cellulose fibers treated with ascorbic acid to bind SAP to the fibers. An NMR spectra also was obtained on L-ascorbic acid. In both cases, separate spectra were acquired using recovery delays of 1 sec and 5 sec between acquisitions.

The peaks in the treated-fiber spectrum were assigned readily to the components: SAP polyacrylate carboxyl (185 ppm) and backbone (50–30 ppm) carbons; cellulose (106, 90, 84, 76, 73 and 66 ppm); and ascorbic acid ring carbons C-1, C-2 and C-3 (175, 119 and 156/153 ppm, respectively); the other ascorbic acid carbons are in the cellulose region, two of them being resolved at 69 and 61 ppm. The ascorbic acid carbon chemical shifts in this ternary mixture were essentially identical (±0.2 ppm) to their values in pure ascorbic acid. This indicated that the ascorbic acid in the treated fibers had undergone no gross structural changes, such as total neutralization, oxidation or ring opening.

The signal-accumulation rates observed at the two different recovery delay times showed that the proton spins in pure ascorbic acid relaxed after excitation much more slowly than they did in the ternary mixture. As shown in the following table, slow relaxation yields higher signal strength at the long recovery delay relative to the short one. The fast proton spin-lattice relaxation in the coated fibers indicated that the ascorbic acid in this system is held more tightly in place (i.e., is less mobile) than in the bulk acid. The ascorbic acid apparently is held tightly by one or both of the other two components, cellulose and SAP, and not by other ascorbic acid molecules.

If the bonding were purely ionic, involving ascorbate ion and an acrylic acid unit in the SAP, then the NMR of the treated fibers would show the ascorbic acid in the salt form. NMR reference spectra were found of the acid and its salt in aqueous solution, and C-3 is seen to shift dramatically on ionization of its OH group: 156 ppm in the acid to 176 ppm in the salt. Thus, since the NMR spectrum of the ternary mixture contains the peaks at around 156 ppm, the ascorbic acid in this system is not ionized.

Looking at acidities, ascorbic and polyacrylic acids have nearly identical $pK_a$ values (4.2 vs 5, respectively). They are both typical strong organic acids with weak conjugate bases. Thus, there is no compelling reason for one of these acids to be neutralized (ionized) by the conjugate base of the other acid. Rather, there should be a strong tendency for an ascorbic acid and an acrylate ion to share a hydrogen ion between them, resulting in a long hydrogen bond between partially ionic ascorbic and acrylic acid units. This sharing of hydrogen ions would certainly be reflected in the IR spectrum, yet satisfies the NMR data by not invoking full ionization of ascorbic acid.

The spectroscopic data are fully consistent with a hydrogen bonding mechanism between ascorbic acid and an acrylate unit in the superabsorber.

| Acrylic Acid NMR Amplitude Ratios at Different Recovery Delay Times. | | |
|---|---|---|
| | Signal Ratio, 5 sec/1 sec | |
| Peak Freq., ppm | Treated Fibers | Pure Acid |
| 176 | 1.99 | 5.21 |
| 156 | 1.92 | — |
| 153 | 1.80 | 5.35 |
| 119 | 2.10 | 4.26 |

B. Infrared Analysis

EXAMPLE 25

Fibers With Superabsorber And Ascorbic Acid

Infrared transmission spectra of the untreated NB316 pulp, the treated NB316 pulp, ascorbic acid, and the IM 100F superabsorber were prepared. Then, a subtraction spectrum representing the treated pulp minus the untreated control was obtained.

Examination of that subtraction spectrum indicated several infrared bands that obviously were associated with the ascorbic acid. They were evident at 1755, 1690 (shifted slightly from 1660–1670), 868, 821, and 756 wave numbers (cm$^{-1}$). However, several other bands that were prominent in the ascorbic acid spectrum were absent in that subtraction spectrum. They included the following: 3525, 3410, 3318, 1319, 1119, and 1026 cm$^{-1}$.

The higher frequency bands (3300–3600 cm$^{-1}$) in ascorbic acid are indicative of bonded OH groups. The infrared bands at 1319, 1119, and 1026 cm$^{-1}$ may also be associated with OH vibrations. consequently, the IR suggested that the subtraction spectrum reflected primarily a loss of the OH groups that were attached directly to the ring. A likely possibility is that the OH groups were replaced by sodium. The only other major band in the subtraction spectrum was located at 1589 cm$^{-1}$. This was probably due to the superabsorber C=O which had shifted to a slightly higher frequency (from 1562 cm$^{-1}$).

The infrared spectra, point to substantial disruption in the structure of the ring OH groups, comparing pure ascorbic acid with the treated fibers, with the ascorbic acid in the mixture resembling ascorbate salts in having some of the OH stretching bands missing.

XV. Activation

The binders of the present invention have the advantage of being activatable from an inactive state on the fibers by addition of liquid, heating, or by kinetic energy such as may be supplied by mechanical agitation, pressure, or ultrasonics. Hence, a liquid binder can be applied to cellulose fibers, loose or in another form, such as a cellulose mat, in the absence of the particles to be bound. The binder is then dried or allowed to dry, for example until the binder and fiber reach an equilibrium moisture content with ambient air. Alternatively, the binder can be applied as a solid, for example, particles sprinkled onto a fiber mat. At a later stage of processing, a liquid such as water is added to the fibers resulting in an activation of the binder. The particulates may then be added, and the binder secures the particulates to the fibers. This subsequent processing of the fibers to attach the particles can occur, for example, at a separate location from the location where the binder was applied to the fibers. Therefore, manufacturers of products can add particulates of interest (e.g., superabsorbent particles or fibers; antimicrobial particles, etc.) at the place of manufacture of the end products that incorporate the treated fibers. Also, more than one type of particulate material (including water soluble and water insoluble particles) may be added, if desired. Particles without the required functionality would not be bound in the same manner.

It also has been found that some of the binders of the present invention can be activated by mechanical agitation (the application of kinetic energy). For example, glycerin binder may be applied to fibrous cellulose. The glycerin binder may be allowed to dry, and the fibers then mechanically agitated in the presence of superabsorbent particles and/or other particles to activate the glycerin binder and bind the particles to the fibers. Mechanical agitation may take place, for example, in a defiberizer where a sheet or mat of glycerin treated cellulose fibers are defiberized while being intimately mixed with SAP that is bound to the fibers by the mechanical agitation.

XVI. Binder Activation Examples

Binder activation in the present invention allows binder to be added to fibers either before or after particles are added to the fibers. The binder is subsequently activated by addition of liquid, heat, or by kinetic energy such as resulting from agitation, and particles are bound to the fibers. The particles may be added to the fibers either before binder activation, after binder activation, or simultaneous with activation. If SAP and/or other particles are to be added to cellulose fibers, for example, the binder may be applied to a pulp sheet which is subsequently fiberized. A liquid such as water may be added to the pulp before or after fiberization, and SAP may be added before or after water addition, or simultaneously with the water. If SAP is added after water addition, the SAP should be applied to the fibers prior to complete evaporation of the added water from the fibers. Water also can be added in other ways, such as by very humid air, a fog or mist, or as steam.

Activation can be of all the fibers, or only portions of the fibers, such as target zones or portions of the mat where particulate binding is desired. The particles may then be added to the mat and adhered to the target zones of the mat which have been activated. In some embodiments, the binder is applied as a solid and heated during a later processing stage to activate the binder by softening it such that it binds the particles to the fibers. The particles may be added in a pattern corresponding to a desired distribution (for example a non-homogeneous distribution) of particles in the fibrous material. Most commonly, however, activation is accomplished by using a binder solvent to moisten a targeted area of the product into which an inactive (dry or dried) binder has already been introduced.

In yet other embodiments, the binder is applied to the fibers and then activated by applying kinetic energy to the fibers. Neat polypropylene glycol (MW 2000) binder, for example, may be sprayed on fibers and allowed to dry. Desired particles are then added to the fibers as the fibers are mechanically agitated in a blender or defiberizer to kinetically activate the binder and bind the particles to the fibers. For kinetic activation, the binder may be added as a liquid or a solid to the fibers. In the case of liquid addition, the liquid is allowed to dry, and then activated by mechanically agitating the fibers and binder. In the case of solid binder addition, the binder is applied as a solid, and then moistened (for example, to a total fiber moisture content of about 7%) and then mechanically agitated.

Activation of the binder may be performed prior to adding the particles, subsequent to adding the particles, or simultaneously with addition of the particles. Once the binder is activated, it adheres a substantial portion of the particles to the fibers, wherein "a substantial portion" refers to about half of the particles added, at least where the particles are not added in excess. Of the particles that are adhered, at least half of them (and more typically substantially all of them, e.g., over 80%) are adhered to the fibers.

In embodiments in which the binder is applied to the fibers as a solid, the activating step can comprise applying a liquid to the fibers after the binder has been applied to the fibers, shortly before the binder is applied to the fibers, or simultaneously with application of the binder to the fibers.

The activating step may be performed after the curing step is complete, if a curing step is to be performed.

The following example will illustrate several specific applications of the activation process, and are not intended to limit the invention to the disclosed methods.

EXAMPLE 26

The method of Example 1 above could be modified such that the SAP is not added until after the web is heated to 140° C. A solid polyethylene glycol/poly-propylene glycol copolymer could be substituted for the binder of Example 1, and it would melt well below 140° C., and in its liquid form bind the SAP to the fibers. The SAP could be applied randomly across the heated product, or applied specifically to a targeted zone of the product where enhanced absorbency is specifically desired.

EXAMPLE 27

A southern kraft pulp sheet would be immersed or sprayed with 154 grams of a 65% solution of polyacrylic acid diluted with 100 ml of deionized water. The sheet is then allowed to dry overnight, heated in an oven at 80° C. for thirty minutes and conditioned in a 50% relative humidity chamber overnight. The sheet is then misted with water to raise its moisture content to 17–20% as it is fed into a Fitz hammermill filled with a three-eighths inch hole screen. Polyacrylate hydrogel particles of FAVOR 800 supplied by Stockhausen would simultaneously be added to the mill by a screw feed device, mixed with the fluff, shunted to an M & J airlay forming machine and airlaid to form a web containing bound SAP throughout the web, i.e., without being confined to a surface of the web. Mixing SAP throughout the fluff helps produce a product in which SAP is homogeneously or randomly distributed, which diminishes problems of gel blocking.

EXAMPLE 28

900 grams of KittyHawk pulp sheet (from the Weyerhaeuser Co., containing 22% synthetic fiber) is immersed in a 10% by weight solution of polyglycine for thirty minutes. The 5 inch wide sheet was then uncoiled on a lab bench to dry overnight, heated in an oven at 80° C. for thirty minutes and conditioned in a 50% relative humidity chamber overnight. The sheet is fed into a Fitz hammermill fitted with a three-eighths inch hold screen, defiberized, shunted to an M & J airlay line, and airlaid into a web. As the web emerges, circular target zones of the web are misted with water from a spray bottle to raise the moisture content to 17–21% in the target zone. Five gram aliquots of starch graft polyacrylate hydrogel fines (IM 1000F; supplied by Hoechst-Celanese of Portsmouth, Va.) are subsequently sifted onto the target zones to yield a web with SAP bound in target zones. The SAP does not form a confluent layer, but is instead present in particulate form on and below the surface of the web.

EXAMPLE 29

A 900 gram amount of a southern bleached kraft pulp sheet was immersed in a 2% by mass solution of ascorbic acid (supplied as a dry powder by Aldrich Chemical Co. of Milwaukee, Wis.) for thirty minutes. The 5 inch wide sheet was then uncoiled on a lab bench to dry overnight, heated in an oven at 80° C. for thirty minutes and conditioned in a 50% relative humidity chamber overnight. The sheet was then gravimetrically determined to be about 7% by weight ascorbic acid. The sheet was misted with water to raise its moisture content to 17–20% as it was fed into a Fitz hammermill fitted with a three-eighths inch hole screen. Misting with water activated the binder prior to addition of superabsorbent particles (SAP). Starch graft polyacrylate hydrogel fines (IM 1000F supplied by Hoechst-Celanese of Portsmouth, Va.) were added as SAP to the hammermill by a screw feed device, mixed with the fluff, shunted to an M & J airlay forming machine (from Horsens, Denmark) and airlaid to form a web. The web that resulted contained 20% SAP attached to the fibers by the binder.

EXAMPLE 30

A 900 gram amount of KittyHawk pulp sheet (from the Weyerhaeuser Co., containing 22% synthetic fibers) was immersed in a 10% by weight solution of urea (supplied by Aldrich of Milwaukee, Wis.) for thirty minutes. The 5-inch-wide sheet was then uncoiled on a lab bench to dry overnight, heated in an oven at 80° C. for thirty minutes and conditioned in a 50% relative humidity chamber overnight. The sheet was then gravimetrically determined to be about 30% by weight urea. The sheet was fed into a Fitz hammermill fitted with a three-eighths-inch hole screen, defiberized, shunted to an M & J airlay line, and airlaid into a web. As the web emerged, the binder in the dried web was activated by misting target zones of the web with deionized water in a circular pattern from a spray bottle to raise the moisture content of the web or the target zones to 17–21%. Five gram aliquots of polyacrylate hydrogel (FAVOR 800 supplied by Stockhausen of Greensboro, N.C.) were subsequently sifted onto each activated target zone. The web that resulted contained target zones with 5 grams of SAP attached to the fibers in each target zone. Alternative spray patterns could be provided by selecting spray heads or different control devices that mist different patterns.

XVII. Thermoplastic Binders

An auxiliary binder also may be used to help bind fibers to each other above the melting point of the auxiliary binder. The auxiliary binder may be a solid thermoplastic material that is applied to the fibers and softened by elevating the temperature during the binding step to above the softening temperature of the auxiliary binder. The auxiliary binder is thereby temporarily softened, rendered more fluid (which for purposes of convenience may be referred to as auxiliary binder melting) and subsequently resolidified as the temperature cools, which thermoplastically binds the fibers to each other, and the particles to the fibers. The auxiliary binder may also contain a hydrogen bonding functionality that hydrogen bonds the particles to the fiber. Examples of auxiliary binders that are thermoplastic and also contain hydrogen bonding groups include ethylene vinyl alcohol, polyvinyl acetate, acrylates, polycarbonates, polyesters and polyamides. Further information about the use of such auxiliary binders can be found in U.S. Pat. No. 5,057,166.

The auxiliary or second binder can be added to the fibers, either before or after a first binder, to help bind the fibers to each other and provide additional binding between the fibers and particles. A suitable second binder would be a thermoplastic or thermosetting binder. In the case of thermoplastic polymers, the polymers may be a material which remains permanently thermoplastic. Alternatively, such polymers may be a material which is partially or fully crosslinkable, with or without an external catalyst, into a thermosetting type polymer. As a few specific examples, suitable thermoplastic binders can be made of the following materials: ethylene vinyl alcohol, polyvinyl acetate, acrylic, polyvinyl acetate acrylate, acrylates, polyvinyl dichloride, ethylene vinyl acetate, ethylene vinyl chloride, polyvinyl chloride, styrene, styrene acrylate, styrene/butadiene, styrene/acrylonitrile, butadiene/acrylonitrile, acrylonitrile/butadiene/styrene, ethylene acrylic acid, polyethylene, urethanes, polycarbonate, oxide, polypropylene, polyesters, and polyimides.

In addition, a few specific examples of thermoset binders include those made of the following materials: epoxy, phenolic, bismaleimide, polyimide, melamine/formaldehyde, polyester, urethanes, urea, and urea/formaldehyde.

More than one of these materials may be used to treat the fibers. For example, a first coating or sheath of a thermoset material may be used followed by a second coating of a thermoplastic material. The superabsorbent particles or other particles are then typically adhered to the outer binder material. During subsequent use of the fibers to make products, the thermoplastic material may be heated to its softening or tack temperature without raising the thermoset material to its curing temperature. The remaining thermoset material permits subsequent heating of the fibers to cure the thermoset material during further processing. Alternatively, the thermoset material may be cured at the same time the thermoplastic material is heated by heating the fibers to the curing temperature of the thermoset with the thermoplastic material also being heated to its tack temperature.

Certain types of binders enhance the fire resistance of the treated fibers, and thereby products made from these fibers. For example, polyvinyl chloride, polyvinyl dichloride, ethylene vinyl chloride and phenolic are fire retardant.

Surfactants may also be included in the liquid binder as desired. Other materials may also be mixed with the liquid binder to impart desired characteristics to the treated fibers. For example, particulate material, such as pigments, may also be included in the binder for application to the fibers.

EXAMPLE 31

As previously described, an auxiliary binder can be used in addition to the polymeric binders of the present invention.

A 3210 gram amount of southern bleached kraft binder (NB-416, supplied by Weyerhaeuser Company) is air entrained in a blenderlike mixing device and sprayed with 2128 grams of a polyvinyl acetate latex (PN-3666H, supplied by H. B. Fuller of Minneapolis, Minn.). While still mixing, 4073 grams of a water swellable polyacrylate hydrogel (IM 1000-60, supplied by Hoechst-Celanese of Portsmouth, Va.) is added and the resulting mixture is then sprayed with 1160 grams of a 50% solution of polypropylene glycol (supplied by Union Carbide of Danbury, Connecticut). The blender is not stopped and the mixture is shunted into a flash tube dryer. The dried product is then airlaid as a 16 inch wide web on a Danweb airlay machine, pressed to a density of approximately 0.15 g/cc, and thermobonded at 140° C. for thirty seconds. The resulting web would have 40% bound SAP and improved tensile strength (as compared to untreated fluff with SAP).

Alternatively, 189 grams of EDTA can be substituted for the 4073 grams of polyacrylate hydrogel.

XVIII. Application of Binder

The binders of the present invention can be added to the fibers in any convenient manner. One such procedure is to spray the binder or binders on a web of the fibers that is conveyed past a sprayer on a conveyor belt. Alternatively, loose fibers may be allowed to fall past a sprayer, or loose fibers may be moved on a conveyor belt past a sprayer. The loose fibers may also be slurried with or immersed in binder. It is also preferable to roll coat the binders on the web, particularly if the binder is viscous. For solid binders, blending of the fiber and binder may be accomplished or the binder may simply be sprinkled onto or otherwise comingled with the fibers, followed by a fixation step such as addition of heat or liquid. The fibers may also be sprayed or immersed in the binder, or binder particles may be applied thereto. These fibers can, while still wet in the case of a liquid binder or following activation of a liquid or solid, be combined with the particles.

The fibers also can be allowed to dry for later activation with an activation fluid, such as an activation liquid, and combined with the particles at that time. An example of when it may be desirable to apply the binder to the fiber and thereafter activate the binder in the presence of particles is when the particles are added at a remote site. For instance, the binder may be activated from an inactive state at a second location that is remote from a first location where the binder is applied to the fibers. The second location may be, for example, a location where a manufacturer combines fibers and particles into articles, such as absorbent articles. Particles may be added from conventional volumetric feeders in a hammermill or from injectors on a paper making line.

One method for uniformly coating the fibers with a binder and adding the particles is shown in U.S. Pat. No. 5,064,689. However, the invention is not limited to any specific mechanism for combining the fiber, binder and particles.

XIX. Production of High Bulk Fibers

Production of high bulk fibers with intrafiber crosslinks is known in the art. Processes for making such fibers are described in EP 440 472 A1; EP 427 317 A2; EP 427 316 A2; and EP 429 112 A2, as well as U.S. patent application Ser. No. 07/607,268 filed Oct. 31, 1990, and its published European counterpart. These high bulk fibers may be used in the present invention, with particles bound to them by the binders disclosed herein. Since methods of making high bulk fibers are known, only a brief description of one such process is given below.

A. Overall System

The apparatus 110 (FIG. 3) of the present invention comprises a conveying device 112 for transporting a mat 114 of cellulose fibers or other fibers through a fiber treatment zone 116; an applicator 118 for applying a treatment substance such as a crosslinking substance from a source 119 thereof to the mat 114 at the fiber treatment zone 116; a fiberizer 120 for completely separating the individual cellulose fibers comprising the mat 114 to form a fiber output comprised of substantially unbroken cellulose fibers substantially without nits or knots; and a dryer 122 coupled to the fiberizer for flashevaporating residual moisture from the fiber output and for curing the crosslinking substance, thereby forming dried and cured cellulose fibers. The mat 114 of cellulose fibers is preferably in an extended sheet form stored in the form of a roll 124 until use. It is normally not necessary that the cellulose fibers comprising the mat 114 be completely dry. Since cellulose is a hydrophilic substance, molecules thereof will typically have a certain level of residual moisture, even after drying. The level of residual moisture is generally 10% wt/wt or less, which is not detectable as "wetness." FIG. 3 also shows that more than one supply, such as multiple rolls 124, of the mat 114 of cellulosic fibers can be simultaneously processed using the present invention.

At the fiber treatment zone 116, sprayers or other applicators 118 apply chemicals such as crosslinking agents to the mat. Typically chemicals are applied uniformly to both sides of the mat. The wetted mat passes between a pair of rollers 128 which assist in distributing the chemicals uniformly through the mat. Other applicators may also, of course, be used.

The crosslinking substance is a liquid solution of any of a variety of crosslinking solutes known in the art. If required, the crosslinking substance can include a catalyst to accelerate the bonding reactions between molecules of the crosslinking substance and cellulose molecules. However, many if not most crosslinking substances do not require a catalyst.

Preferred types of crosslinking substances are selected from a group consisting of urea derivatives such as methylolated urea, methylolated cyclic ureas, methylolated lower alkyl substituted cyclic ureas, methylolated dihydroxy cyclic ureas, and mixtures thereof. A specifically preferred crosslinking substance would be dimethyloldihydroxyethylene urea (DMDHEU). In addition, crosslinking substances can be polycarboxylic acids, such as citric acid. Crosslinking materials are known in the art, such as described in the previously mentioned Chung patent, U.S. Pat. No. 4,935,022 to Lash, et al., U.S. Pat. No. 4,889,595 to Herron, et al., U.S. Pat. No. 3,819,470 to Shaw, et al., U.S. Pat. No. 3,658,613 to Steijer, al., U.S. Pat. No. 4,822,453 to Dean, et al., and U.S. Pat. No. 4,853,086 to Graef, et al.

Suitable catalysts include acidic salts which can be useful when urea-based crosslinking substances are used. Such salts include ammonium chloride, ammonium sulfate, aluminum chloride, magnesium chloride, or mixtures of these or other similar compounds. Alkali metal salts of phosphorus-containing acids may also be used.

In FIG. 3, the crosslinking substance applied to the mat 114 is obtained from a supply 119 thereof, such as a tank or analogous vessel.

Crosslinked cellulose fibers are individual fibers each comprised of multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents." Suitable crosslinking agents are generally of the bifunctional type which create covalently bonded "bridges" between said neighboring hydroxyl groups.

B. Conveying Device

Referring further to FIG. 3, each mat 114 of cellulosic fibers is conveyed by a conveying device 112, which carries the mats through the fiber treatment zone 116. FIG. 3 also shows a further portion of one type of conveying device comprised of a first pair of rollers 126 and a second pair of rollers 128 for each mat 114. The first and second pair of rollers 126, 128 are particularly effective for urging the corresponding mat at a substantially constant and controlled rate of speed.

C. Fiber Treatment Zone

Each mat 114 is urged by the first and second pair of rollers 126, 128 through the fiber treatment zone 116 where the mat 114 is impregnated with a liquid crosslinking substance. The crosslinking substance is preferably applied to one or both surfaces of the mat using any of a variety of methods known in the art useful for such a purpose, such as spraying, rolling, dipping, or analogous method. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

D. Fiberizer

The next subsystem following the fiber treatment zone is a fiberizer 120 which serves to comminute one or more mats 130 impregnated with the crosslinking substance into individual substantially unbroken cellulose fibers comprising a fiber output.

Referring further to FIG. 3, a first conveyer fan 260 of conventional design can be utilized for propelling the fibers from the outlet 162 of the attrition device 132 through a conduit 262.

An optional component of the fiberizer 120 is a first cyclone 264 or similar apparatus known in the art, utilized in a conventional manner to concentrate the fibers passing out of the outlet 162 of the attrition device 132. The first cyclone 264 receives the fibers through the conduit 262 coupled thereto.

Excess air can be recovered at the top 266 of the first cyclone 264 and recycled as required through a conduit 268 to a location upstream of the first conveyer fan 260 (if used). Such additional air can be beneficial for easing the transfer of the fibers through the first conveyer fan 260.

A disk refiner 268 is another optional component of the fiberizer 120 which can be employed to effect additional separation of fibers (removal of knots) if required. The disk refiner 268 is of a type known in the art and comprises a disk refiner inlet 270 and a disk refiner outlet 272. A representative disk refiner 268 is type DM36 manufactured by Sprout-Bauer, Incorporated of Muncie, Pennsylvania. If the disk refiner 268 is used, the inlet 270 thereof is coupled via a conduit 274 to an outlet 276 of the first cyclone 264.

A second conveyor fan 278 may optionally be utilized to urge propagation of the fibers through a conduit 180 downstream of the disk refiner 268. Excess air can be recovered from the top 266 of the first cyclone 264 and routed via a conduit 281 to a tee 282 just upstream of the second conveyor fan 278.

Another optional component of the fiberizer 120 is a fluff generator 290 which receives the fibers from the optional second conveyor fan 278 through a conduit 284. The fluff generator is described in detail below and in copending U.S. patent application Ser. No. 07/607,157.

E. Drver

Referring further to FIG. 3, a preferred embodiment of the present apparatus 110 includes a dryer 122 which is utilized to perform two sequential functions: remove residual moisture from the fibers and cure the crosslinking agent. Preferably, the dryer 122 comprises a drying zone 373 for receiving fibers, e.g. from fluff generator outlet 304 and for removing residual moisture from the fibers via a "flash drying" method and a second drying zone 360, 362 for curing the crosslinking agent. In FIG. 3, the curing starts in zone 360 and continues through zone 362.

The FIG. 1 embodiment shows that zone 373 is coupled to the fluff generator outlet by a conduit 372 and to a source 374 of heated air, typically produced by combustion of a supply of natural gas 376 and fresh air 378. The temperature of heated air is regulated to maintain the temperature of the drying zone 373 within a range of about 200° C. to about 315° C. As the fiber output passes into the drying zone 373, the wet fibers comprising the fiber output are substantially instantaneously exposed to the high temperature in this zone. Such rapid exposure to high temperature imparts a "flash drying" effect to the fibers, thereby causing rapid and thorough drying and separation of the fibers. The passage time through the drying zone 373 is preferably less than one second.

The FIG. 3 embodiment shows that the first zone 360 is comprised of a first tower 364 comprised of a body portion 366, an inlet 368, and a first tower outlet 370. The dryer zone 373 is coupled via a conduit 372 to the outlet of the fluff generator 290.

In FIG. 3, the first tower 364 is shown preferably coupled via a conduit 380 to a down tube 382, which is coupled via a conduit 384 to a third conveyor fan 386 located at an inlet 388 of a second tower 390. The third conveyor fan 386 transports the fibers through the dryer which thereby pass into the second tower 390. As the fibers are lofted through the second tower 390, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as to not scorch the fibers during curing. It should be noted that single stage dryers may also be used.

The dried and cured fibers exiting the dryer outlet of tower 390 have an extremely low level of nits and virtually no knots. Further, they are not discolored from scorching and the like, and have a median fiber length substantially unchanged from the median length of the fibers comprising the mat 14.

FIG. 3 also shows a second cyclone 400 of conventional design coupled via a conduit 402 to the outlet of tower 390, serving to concentrate the fibers passing therethrough in preparation for collection. The resulting concentrated fibers can be collected using any of a number of collection devices 408 known in the art, such as fiber bagging devices.

EXAMPLE 32

In this example, non-woven fibrous mats were impregnated with a crosslinking agent, fiberized, dried, and cured using the apparatus as diagrammed schematically in FIG. 3.

Two 52-inch-wide mats of southern pine kraft wood pulp fibers (type NB316 from Weyerhaeuser Company) and having a basis weight of 680 g/m$^2$ were fed to the apparatus. The mats were impregnated using dimethyloldihydroxyethylene urea at a concentration of about 5%, applied over both sides of each mat using a combination of spray nozzles and impregnation rollers. The loading level of crosslinking agent was about 4.5% w/w.

The treated fiber mats were fed at the rate of 8 meters/min to the attrition device 32. The specific attrition device used in this example was equipped with six mat inlets and a rotor having 16 rows of hammers as described above around the circumference of the rotor. The rotor had a diameter of 30 inches and was rotated at an angular velocity of 1200 rpm by an electric motor. Other rpm rates have also been tested and have proven satisfactory, including extremely high rpm rates.

Random samples of fibers were obtained from the output attrition device and observed for nits. These samples were 2.6 grams and were consistently observed to have fewer than three nits on the average with most samples having no nits. The attrition device was flushed with water once every sixteen hours for cleaning purposes.

A disk refiner was employed downstream of the attrition device. This specific disk refiner was a DM36 refiner as previously mentioned. A fluff generator as described in FIGS. 7–9 was also employed in this downstream of the disk refiner. The temperature at the dryer input in this example was within the range of 200° C. to 315° C. The temperature at the second tower outlet was within the range of 140° C. to 180° C. Crosslinked fiber at the output of the dryer was produced at a rate of about 5000 pounds per hour. The particle binders and particles of the present invention can be added before, after, or simultaneously with curing. The term "curing in the presence of the binder" means that the binder is added before or simultaneously with curing. Curing in the presence of the binder is not usually a problem because the binder cannot always participate in the intrafiber crosslinking reaction, and the binder is not affected by the curing step. In certain situations, however, the binder can also form covalent intrafiber crosslinks. Polycarboxylic acids (such as citric acid), polyols (such as dipropylene glycol) and polyamines (such as ethylene diamine) can function as crosslinking agents, and are consumed during the curing step in the formation of covalent crosslinks. Hence in the limited case in which the crosslinking agent is also a binder material, steps should be taken to prevent the binder from being consumed as a crosslinker in the curing step.

Formation of the intrafiber covalent ester bond requires an anhydride intermediate. Formation of the anhydride intermediate can be inhibited by the presence of water. The present inventors have found that about 20% water (more preferably at least 30% water) by weight in the fibers will sufficiently retard curing so that adequate binder functional groups will remain available in the fibers to bind the particles to the fibers. Hence when curing the crosslinking material in the presence of a binder that is also a crosslinking material, the fibers should contain at least about 20% water by weight of the fibers when curing begins. When curing the crosslinking material in the presence of a binder that is not also a crosslinking material, steps to prevent covalent bond formation are not usually necessary. When the crosslinking material is not cured in the presence of the binder, that is when the binder is applied after curing, no steps need be taken to inhibit covalent bond formation.

XX. composite Absorbent Product

In accordance with the present invention, absorbent structures or articles may be made from the fibers, with binder and adhered particulates. These articles may be composite structures (e.g., made of plural materials). For example, the articles may have a core of plural types of fibers, or fiber layers, with or without covering materials. These products are capable of absorbing significant quantities of water and other fluids, such as urine and other body fluids. Such products include, but are not limited to, disposable diapers, sanitary napkins, incontinent pads, towels and the like.

Figure 4:
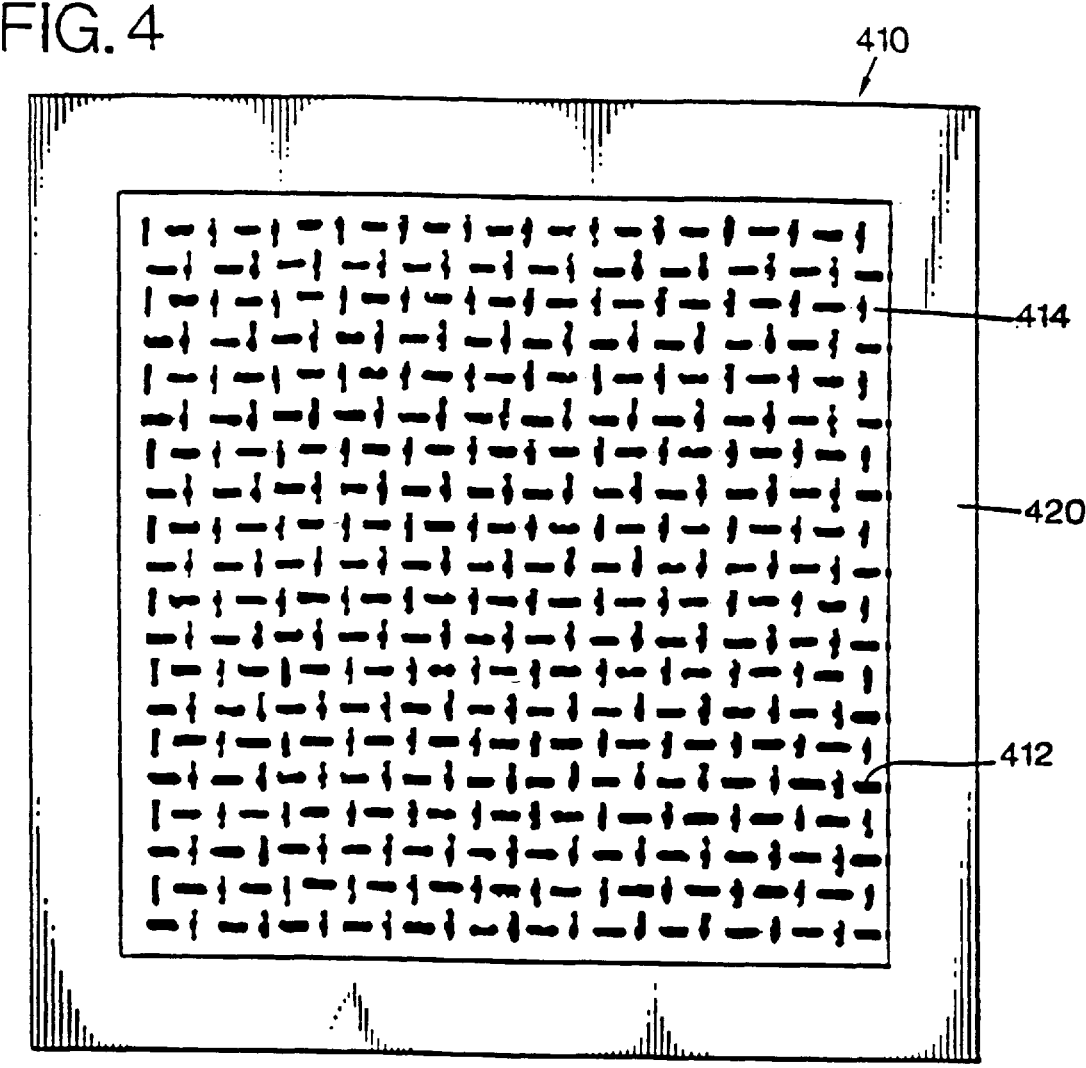
FIG. 4 is a top plan view of a structure into which fibers of the present invention are incorporated with attached particles, the fibers being in the form of an illustrated absorbent pad.
Figure 5:
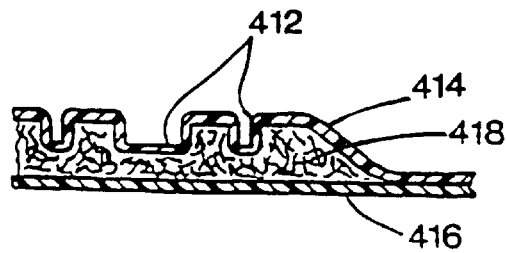
FIG. 5 represents a partial sectional view of the pad of FIG. 4.

FIGS. 4–5 illustrate an absorbent pad structure which may be formed from fibers of the present invention, whether or not they are blended with other fibers. FIGS. 4 and 5 represent an absorbent pad 410 having a heat embossed screen pattern 412. Pads having no pattern may also be used. A pad having a cover sheet 414 and a backing sheet 416 may be formed, for example, by placing a square fiber piece cut from the sheet onto a corresponding precut backing sheet. A corresponding precut cover sheet is placed over the top of the fiber 418 on the backing sheet. This assembly may then be adhesively bonded around a continuous margin 420.

With reference to FIGS. 6–7, an absorbent structure in the form of a bandage is shown. A bandage 430 for application to a wound to absorb blood and other bodily fluids is shown. An absorbent pad 440 is securely mounted to an exterior or pad mounting surface 434 of a backing strip 436. Fibers 441 are contained in pad 440, and particles are attached to the fibers 441 in accordance with the present invention. Any suitable mounting or securing means may be used to affix pad 440 to the surface 434 of the strip 436. However, it is preferable for surface 434 to be coated with an adhesive so that the pad 440 may be adhesively mounted in place. An exemplary adhesive is ethylene vinyl acetate adhesive. It is also desirable for the overall surface 438 of backing strip 436 to be coated with a conventional adhesive. Surface 438 is the surface which is affixed to the area of the skin surrounding the wound. Conventional "peel-back" tabs may be used to protect the adhesive coating and pad 440 until the bandage is to be applied. This type of backing strip is well known in the art.

The backing strip 436 may be of any known flexible material suitable for application to the skin. It is preferable for the strip 416 to be of a material which is impermeable to the passage of liquid so that fluid from a wound is contained by the bandage. However, the strip 436 may be apertured or otherwise breathable to permit air to reach the wound to promote the healing process. A specific example of a suitable backing strip 436 is a polyethylene film.

As in the other structures described, a variety of combinations of antimicrobials and other particles may be used in the fibers 441 of such a bandage. Again, however, the particles are adhered securely in place when the particles have a hydrogen bonding or a coordinate covalent bonding functionality, the fibers to which these particles are bound have a hydrogen bonding functionality, and wherein the binder is selected from the group consisting of a polypropylene glycol, a polypropylene glycol/polyethylene glycol copolymer, a polycarboxylic acid, such as polyacrylic acid, a poly(lactone) diol, such as poly(caprolactone) diol, a polyamide, a polyamine, a polysulfonic acid, a polysulfonate, polycarboxylate and combinations thereof.

The polymeric binder has a hydrogen bonding or a coordinate covalent bond forming functionality. Nonpolymeric binders would include organic binders such as glycerin, monoglycerides, diglycerides, ascorbic acid, urea, glycine, pentaerythritol, a monosaccharide or a disaccharide, citric acid, tartaric acid, taurine, dipropylene glycol, and urea derivatives such as DMDHEU. Suitable saccharides include glucose, sucrose, lactose, ribose, fructose, mannose, arabinose, and erythrose. Two different particles, such as different antimicrobials in particulate form, may be adhered to the same fiber. In the alternative, each different type of antimicrobial particle or other particle may be adhered separately to different fibers. Also, blends of fibers may be included in absorbent structures such as pad 366. For example, these blends may include fibers with adhered antimicrobial (one or more antimicrobials) particles and adhered superabsorbent particles; fibers with one or more antimicrobial particles without superabsorbent particles blended with fibers having adhered superabsorbent particles. with or without antimicrobial particles, and combinations of such fibers with untreated fibers and/or binder coated fibers without superabsorbent particles or antimicrobial particles. In addition, other particles, such as anticoagulants or hemostatics may be attached to the fibers.

The absorbent pad of bandage 430 may also include a cover sheet that is typically made of any suitable material which will readily permit the passage of liquid through the cover sheet to the fibers 441, such as nonwoven fiber webs of fibers such as, for example, rayon, nylon, polyester, propylene and blends thereof. One specifically preferred cover sheet material is a 70 percent rayon/30 percent polyester blend having a basis weight of 18 g/m$^2$ from Scott Paper Company.

Figure 8:
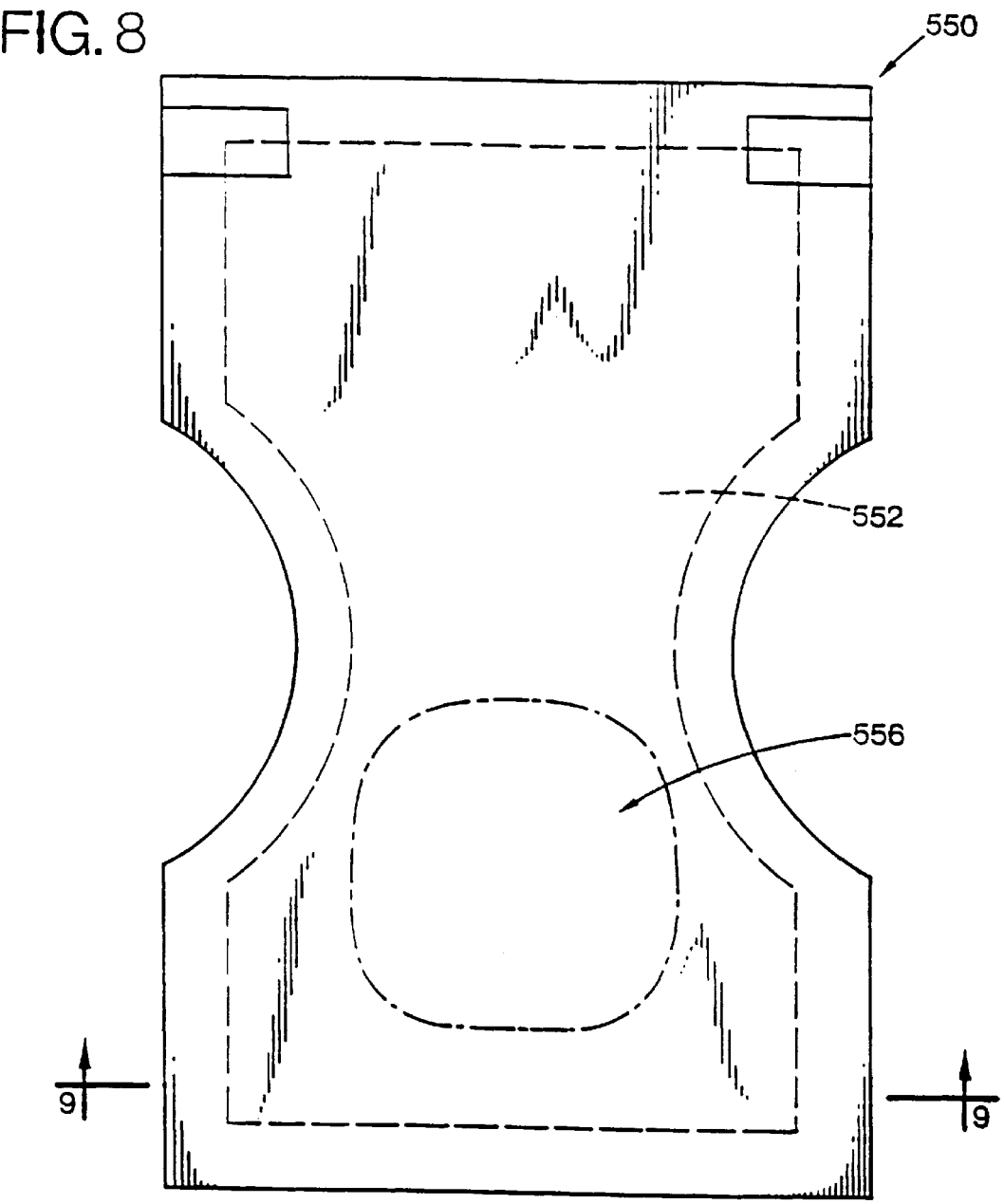
FIG. 8 is a plan view of a disposable diaper including a core of fibers of the present invention.
Figure 9:
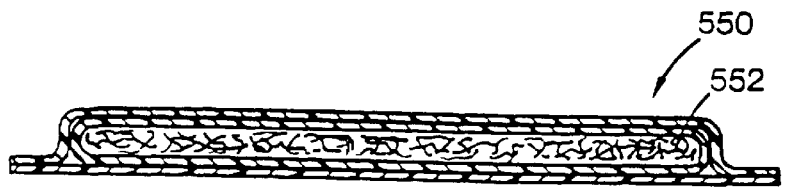
FIG. 9 is a vertical sectional view along line 9—9 of the diaper of FIG. 8.

FIGS. 8 and 9 illustrate a conventional disposable diaper 550 with a core 552 which is comprised of fibers of the present invention with adhered superabsorbent particulate materials. These particulate materials may be confined to a target zone (for example the front or crotch portion of a diaper indicated at 556) or of a heavier concentration in the target zone. This can be accomplished by airlaying fibers of the present invention in such a zone. Also, the core may be activated by melting the binder or moistening the target zone with water. The superabsorbent particles may be sprinkled on or otherwise applied to this wetted zone. As the zone dries, the particles are adhered in place.

XXI. Densification

The products such as described above, as well as webs of the fibers of the present invention, can also be densified by external application of pressure to the web. The web could be densified by passing it through a set of calendar rolls set at 60 and 90 pli (pounds per linear inch, as in a calendar press) respectively to yield sheets with increased densities. Densification may alternatively be provided by compaction rolls or presses. The inventors have found that densification is facilitated in SAP-containing products treated with binders of the present invention, when the densification occurs with the binder in an active state. Products that are treated with these binders require less heat and pressure than untreated fibers to densify to a given density. Densification is preferably performed to produce a product that has a density of about 0.05 to 0.7 g/cc, more preferably 0.1 to 0.3 g/cc.

An example of densification using some of the binders of the present invention is given below:

EXAMPLE 33

The products of the present invention can be formed into 550 gram/square meter sheets, six inches in diameter, in a laboratory padformer. Those pads are then passed through a set of calendar rolls set at 60 and 90 pli, respectively to yield sheets with densities of 0.3 and 0.5 g/cc.

EXAMPLE 34

A 50 gram amount of polypropylene glycol is diluted with 50 grams deionized water. The resulting solution is sprayed on 321 grams of an intrafiber crosslinked cellulose fluff (HBA pulp from Weyerhaeuser Company of Tacoma, Wash.) that was air entrained in a blender like mixing device. While the HBA fiber is still damp, 438 grams of IM 1000F (supplied by Hoechst-Celanese, of Portsmouth, Va.) is added to the mixture. The resultant mixture is then vacuumed from the blender and spread on a counter to dry overnight. Then 550 gram/square meter handsheets, six inches in diameter, are made in a laboratory padformer. Those pads are then pressed at 2000 and 3000 psi (or 60 and 90 pli in a calendar roll), respectively, to yield sheets with densities of 0.3 and 0.5 g/cc. Alternatively, pads of untreated HBA pulp blended with 45% IM 1000F would require heating to 100° C. and pressures between 8,000 and 11,000 psi to produce pads of similar densities.

EXAMPLE 35

HBA pulp with 40% IM1000F and HBA pulp with 12% glycerin and 40% IM1000F were formed into six-inch pads in the padformer then pressed at about 6500 psi for 15 seconds. HBA pulp without glycerin binder reached a density of 0.4 g/cc and HBA pulp with glycerin bound particles reached a density of 0.57 g/cc. This example illustrates that fibers treated with the method of the present invention achieve a greater density than untreated fibers at the same compression pressure.

XXII. Water Addition

In some embodiments of the invention, a crosslinking material is added to the fibers and cured to form intrafiber covalent bonds that produce high bulk fibers. If the crosslinking material and binder are the same (for example, a polycarboxylic acid), or are both different but capable of intrafiber crosslinking, and the binder is added before curing occurs, substantially all of the crosslinking material/binder will be used in the covalent crosslinking reaction, such that none will be available for subsequent binding of the particles to the fibers with hydrogen bonds and coordinate covalent bonds. In this particular instance (where the crosslinking material and binder are both capable of crosslinking, and are added before curing) water may be added to the fibers before curing to retard initiation of the curing step and ensure that a portion of the binder's functionality is not consumed in the crosslinking reaction. At least 20% water by weight in the fibers sufficiently retards intrafiber covalent bond formation to allow residual polycarboxylic acid on the fibers to bind the particles to the fibers. The following example illustrates this process.

EXAMPLE 36

A 100 gram pulp sheet was sprayed with 44.5% intrafiber crosslinking material, and the pulp sheet was then delaminated and fed in small bits into a padformer while adding superabsorbent particles to delaminated pulp sheet at the same time. The material was run a second time through the padformer to fluff it up, and the material was then subsequently cured for 20 minutes in an oven at 150° C.

In a first run, the crosslinking material was a modified ethylene urea and citric acid, while the particulate material was IM1000F. To the 100 g pulp sheet was added 63.4 grams of the ethylene urea, 16.76 grams citric acid, and 70 grams of IM1000F, for a final crosslinker content of 35.2% ethylene urea and 9.3% citric acid, by weight. No water was added in this run.

In a second run, the 100 gram pulp sheet was crosslinked with 30.83 grams of a polyaldehyde (glyoxal), 5.03 grams of a glycol, 0.2 grams alum, 0.2 grams citric acid, and 15 grams distilled water. Curing was performed after 70 grams of IM1000F SAP was added to the pad.

Attachment of the particles to the pad was poor in both of these runs. Each of these runs was then repeated, except 50 grams of distilled water was added before curing. Hence there was 50 g of water in the first run and 65 g of water in the second run. Particle attachment to the fibers was greatly improved.

Electron microscopic examination of the fibers from these runs showed that particle bonding did not occur in the absence of the 50 g water addition. In the presence of 50 grams distilled water, however, electromicroscopic data showed actual bonding of the particles to the fibers.

XXIII. Particulate Binding

Figure 10:
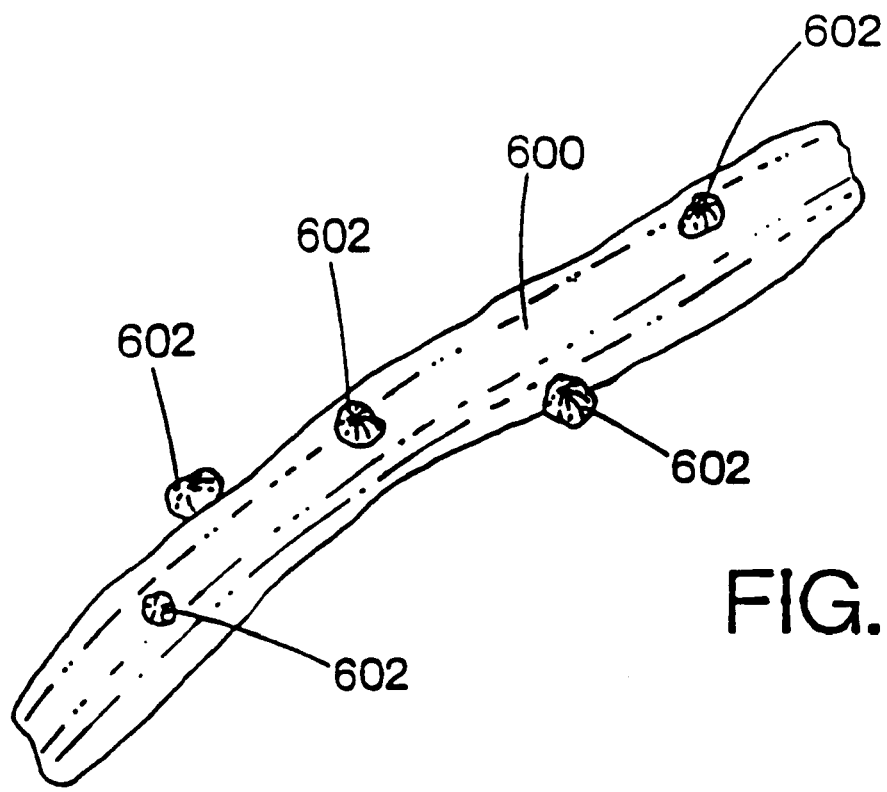
FIG. 10 is a view of an enlarged fiber with particles bonded to the fiber with the binders of the present invention.

FIG. 10 shows an isolated, enlarged cellulose fiber 600 with SAP particles 602 bound to it by a binder of the present invention. This drawing illustrates an example of the SAP retaining its discrete particulate form following binding to the fibers. Some particle to particle fusion may occur in accordance with this invention, but maintenance of a discrete particulate form excludes formation of a completely confluent film in which the particles lose their particulate identity. Such a confluent film produces gel blocking that interferes with efficient liquid absorption into the fibers.

The shown fiber 600 is elongated, and has an aspect ratio (ratio of length to width) of about 10:1 to 5:1, preferably about 10:1.

Figure 11:
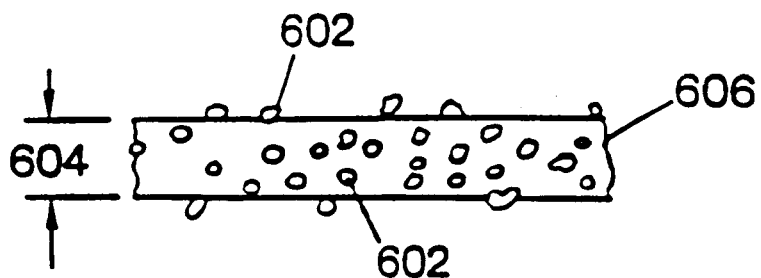
FIG. 11 is a schematic view of a cellulose mat with particles bound to all its surfaces and throughout its depth.

FIG. 11 shows the particles 602 distributed substantially uniformly throughout the depth 604 of a pad 606. The particles are also shown adhering to all the surfaces of the pad. Particles may be distributed in any desired pattern throughout the pad in accordance with this invention, and need not necessarily adhere to all surfaces or be distributed throughout the volume of the mat, or distributed uniformly.

As can be seen from FIGS. 10–11 (and FIGS. 12–15 discussed below), the particles are not encapsulated by the binders. The particles and fibers of the present invention are not encapsulated with the binder. Moreover, the binder does not agglomerate the fibers together, and in many embodiments does not bind fibers to each other. Discrete individual particles retain their identity on the surface of the fibers, instead of being subsumed in a thermoplastic encasement around the fiber and particle.

XXIV. Electron Photomicrographs

Figure 12:
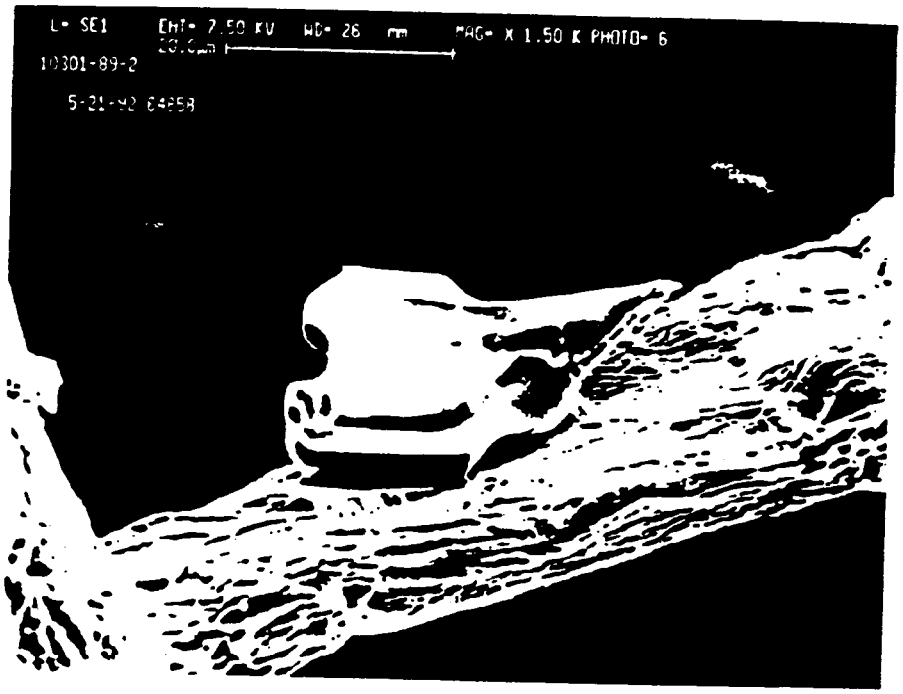
FIG. 12 is a photomicrograph of particles adhered to fibers with an ascorbic acid binder.
Figure 16:
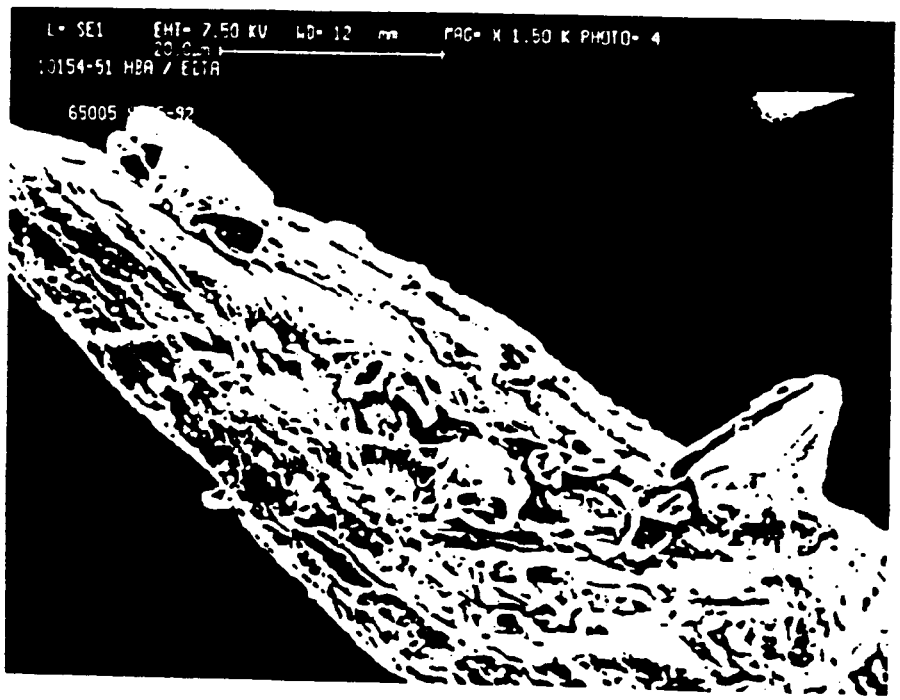
FIG. 16 is a photomicrograph of EDTA (ethylenediaminetetraacetic acid) particles bound to a crosslinked fiber with a glycerin binder.

An electron photomicrograph of superabsorbent particles (SAP) bound to cellulose fibers with an ascorbic acid binder is shown in FIG. 12. The SAP is at the left margin of the photograph, and is bound to the fiber which occupies the central portion of the photomicrograph. The particle is seen to be bound to the fiber, and the fiber has undergone some shear damage that resulted in a fracture of the fiber. It is significant that the fiber has experienced shear damage while the particle has remained bound to the fiber, because this indicates that the particle-fiber bond formed by the ascorbic acid is very strong and resilient, resisting mechanical disruption.

Figure 13A:
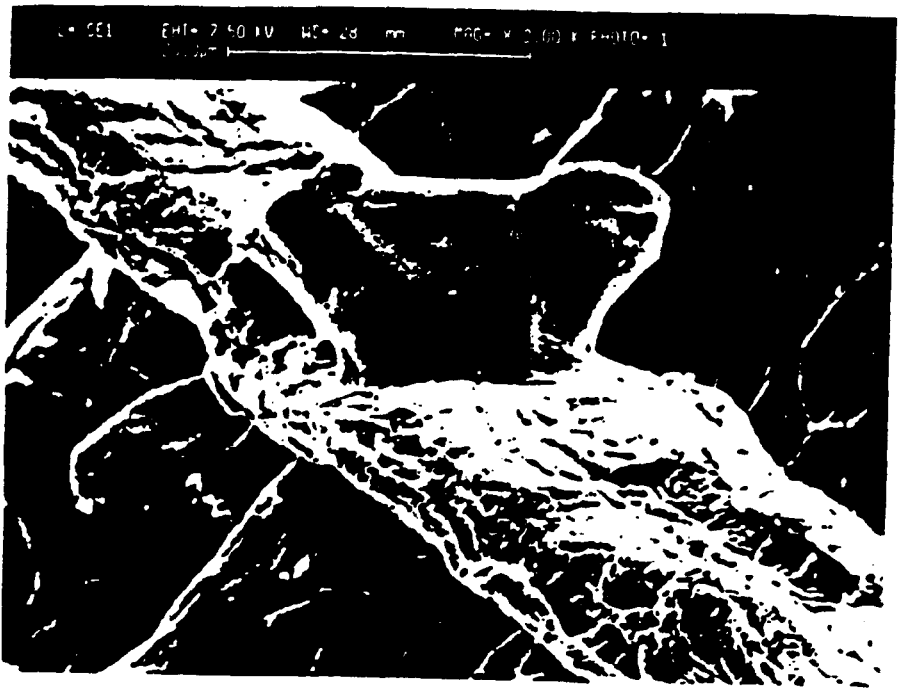
FIGS. 13A, 13B, 13C, and 13D are photomicrographs of particles bound to fibers with lactose.
Figure 13B:
Figure 13C:
Figure 13D:

FIGS. 13A, 13B, 13C and 13D show several electron photomicrographs that illustrate individual particles bound to fibers with a lactose binder. FIG. 13C, for example, shows that SAP retains its individual particulate form when adhered to the fiber with a lactose binder. The particles do not form a fused confluent mass without particulate identity.

EXAMPLE 37

An electron photomicrograph of oxalic acid particles bound to cellulose fibers with a glycerin binder is shown in FIG. 14. The bound oxalic acid is near the center of the photograph, and is seen bound to the fiber without mechanical encapsulation of the fiber and particle by an encapsulating binder.

FIG. 15 is an SEM illustrating a particle of aluminum sulfate (alum) bound to a cellulose fiber with a glycerin binder. The alum particle is seen at the center of the photograph, and the particle retains its individual particulate form when adhered to the fiber. The particles do not form a confluent mass lacking particulate identity. Moreover, the particles are not encapsulated by a material that mechanically holds the particle in contact with the fiber.

XXV. Fiber Mixtures

The fibers of the present invention, such as fiber 600, can be mixed with other types of fibers, such as that disclosed in U.S. Pat. No. 5,057,166. The latex coated fibers of that patent can be mixed with the fibers of the present invention to produce an absorbent product that has characteristics of both types of fibers.

XXVI. Additional Binder characteristics

U.S. Pat. No. 3,903,889 discloses a process for adhering absorbent particles to pulp fibers using syrup, honey, and other polysaccharides such as dextrins. An essential requirement of these adhesive agents is that they must possess the property of being permanently pliable, and not rigidifying into a brittle film. The binders of the present invention, in contrast, are capable of functioning as a binder after solidifying into a rigid crystalline material. Even the binders of the present invention that do not rigidify into a solid (such as glycerin and PPG) are very hygroscopic, and can be present on fibers having a total water content of no more than 15%, or even 12%. This is in contrast to the adhesives such as honey and corn syrup disclosed in U.S. Pat. No. 3,903,889 that are not hygroscopic. Polysaccharides (such as corn syrup, honey and dextrins) are excluded as binders from some embodiments of the invention because they remain tacky upon drying. Tacky binders make processing the binder-coated fibers difficult. The polysaccharide polymers are also excluded from non-polymeric embodiments of the binder of the present invention. Moreover, the non-polymeric saccharides such as monosaccharides and disaccharides, lack the high viscosity and tacky adhesive physical properties of polysaccharides such as corn syrup and honey. The non-polymeric saccharides of the present invention may be solids, which avoid the viscosity and handling problems associated with polymers.

As used in this application, a particle that is soluble in water will completely dissolve at least 10 grams of the particle in 300 ml. water at 25° C. A particle that is sparingly soluble in the binder will completely dissolve no more than about 5 grams of the particle in 300 ml. of the binder at 25° C.

Some of the binders of the present invention are also water soluble. A binder that is water will completely dissolve at least 10 grams of the binder in 300 ml. water at 25° C.

XXV. Fiber Densification Without Particles

In accordance with another aspect of this invention, the present inventors have observed that when densifying agents such as those described below are applied to fibers for example those described above which have hydrogen bonding functionality, the fibers density to a greater degree than fibers that have not been treated with a densifying agent. Densifying agents that can be used to improve the densifiability of the fibers generally include, but are not limited to organic and inorganic materials that have a density greater than the dry density of the fibers. Such densifying agents can be applied to the fibers in the same manner that the binders described above are applied to fibers. In addition to the methods for densifying fibers described above, the advantages of this aspect of the present invention also apply to densification of the fibers in a bale former.

Organic densifying agents that are useful include the organic polymeric and non-polymeric binders described above. When such binders are employed as densifying agents, it is not necessary that the molecules contain functionality to bind particles. Hence, organic molecules containing only one hydrogen bonding functionality may be useful as a densifying agent. Although the densifying agents are not required to bond to the fibers, in preferred embodiments they do bond to the fibers. In addition to the binder functionalities expressly described above, binders that are useful as densifying agents may also include sulfonamide or phosphoramide functionalities. At this time, preferred non-polymeric organic densifying agents include sorbitol, glycerin, propylene glycol, and mixtures thereof. In accordance with this aspect of the present invention, the organic densifying agents can be applied to the fibers in an amount ranging from about 0.1% to about 30% by weight based in the combined weight of the fibers and densifying agent.

In addition to improving the densification properties of the fibers, it has also observed that the preferred densifying agents sorbitol and glycerin improve the softness of the fibers and articles containing the fibers before and after densification. The organic acid, lactic acid, while not improving the densifiability of fibers when applied thereto has been observed to soften fibers treated therewith. Softness relates to stiffness of the fibers or articles containing the fibers, the drape or hand of articles including the fibers. Another aspect of softness relates to abrasiveness or lack thereof of a fiber or article containing the fiber. Compressibility is another aspect of softness. Various tests exist to evaluate some of these aspects of softness, including Gurley stiffness, Taber stiffness, measurements of coefficients of friction, handlometers, and the like. It should be understood that none of the tests listed above completely quantifies or evaluates softness or fibers or articles containing fibers; therefore subjective testing is also done to assess the softness of a material.

In addition to the polymeric and non-polymeric organic densifying agents described above, the present inventors have also observed that some inorganic materials also improve the densifiability of fibers to which the agents are applied. As with the organic densifying agents, the inorganic densifying agents generally include, but are not limited to those characterized by a density greater than the density of the dry fibers. In addition, the inorganic densifying agents when added to the fibers will increase the mass of the fibers without appreciably affecting the volume of the fibers. The inorganic densifying agents may increase the mass without appreciably affecting the volume of the fibers by occupying the preexisting spaces within the fibers, such as the lumen, pores, and the like. Preferably, any increase in volume of the fibers caused by the addition of the densifying agent will be less than the increase in mass of the fibers, such that the density of the fibers in increased.

Examples of inorganic densifying agents which may have a density greater than the fibers and that will increase the mass of the fibers without appreciably affecting the volume of the fibers include inorganic acid salts in which the cation is monovalent, such as alkali metal, ammonium, or substituted ammonium (such as mono-, di-, tri-, or tetra-alkyl substituted ammonium, with the alkyl groups having from one to six carbon atoms, for example, triethyl or trimethyl ammonium, tetramethyl or tetraethyl ammonium). Suitable densifying agents include alkali metal, ammonium, or substituted ammonium salts of pyrophosphates, hexametaphosphates, tripolyphosphates, hypophosphates, polyphosphoric acid, ethylenediaminetetraacetic acid, hydroxyethylidenediphosphonate; and aminotri-(methylenephosphonate). Specific densifying agents include sodium hypophosphate tetrapotassium pyrophosphate, and tetrasodium pyrophosphate. Tetrasodium pyrophosphate and tetrapotassium pyrophosphate are particularly useful. Other specific densifying agents include sodium hexametaphosphate, sodium salt of ethylenediaminetetraacetic acid, sodium polyphosphate, sodium salt of diethylenetriaminepentaacetic acid, sodium salt of hydroxyethylethylenediaminetriacetic acid, and sodium salt of dihydroxyethylglycine. Still other densifying agents include alkali metal, ammonium, or substituted ammonium salts of oxalates, phosphates, and tungstates. Sodium oxalate, dibasic sodium phosphate and sodium tungstate are particularly useful. Mixtures of the foregoing densifying agents are also useful. In accordance with this aspect of the present invention the inorganic densifying agents can be applied in an amount from about 1.0% to about 50% by weight based on the fibers and densifying agent.

Without intending to lirnit the scope of the present invention, one possible explanation for the effect the densifying agents have on the densifiability and softness of the fibers can be explained by considering the hydrogen bonding that occurs between cellulose molecules within a cellulose fiber and within a specific cellulose molecule. The densifying agents when applied to the fibers may disrupt or promote the disruption of existing hydrogen bonding between cellulose molecules or within a given cellulose molecule. In other words, the densifying agent may occupy sites on the cellulose molecule that would otherwise form hydrogen bonds within the molecule or with other cellulose molecules.

With respect to the inorganic densifying agents, such as TKPP, another possible explanation for the effect the inorganic densifying agent has on the densifiability and softness of the fibers or articles containing the fibers relates to TKPP's hygroscopic property wherein it attracts moisture from the surrounding environment into the fibers which have been treated with TKPP. This moisture may disrupt or participate in the disruption of hydrogen bonding between cellulose molecules or within a cellulose molecule as explained above. In addition to increasing the densifiability of fibers, the present inventors have also observed that TKPP softens the fibers when applied thereto. Other inorganic densifying agents that are hygroscopic and may also soften the fibers include many alkali metal, ammonium, or substituted ammonium salts of pyrophosphates, hexametaphosphates, tripolyphosphates, hypophosphates, polyphosphoric acid, ethylenediaminetetraacetic acid, hydroxyethylidenediphosphonate; and aminotri-(methylenephosphonate). Specific hygroscopic densifying agents include sodium hypophosphate, tetrapotassium pyrophosphate, and disodium phosphate. Tetrapotassium pyrophosphate is particularly useful. Other specific densifying agents that are hygroscopic include sodium hexametaphosphate and potassium salt of ethylenediaminetetraacetic acid. Mixtures of hygroscopic and non-hygroscopic densifying agents are also useful.

The advantages of this aspect of the present invention extend to products in composition that include fibers treated with a densifying agent as described above where no particulate material, such as super absorbent is present or where a particulate material, such as super absorbent is present but not bound to the fibers.

The following examples illustrate how the application of a densifying agent to pulp fibers yields a product that is easier to densify than the same untreated pulp fibers.

EXAMPLE 38

A sample of NB 416 pulp sheet (available from Weyerhaeuser Company, Tacoma, Wash.) was sprayed with different levels of glycerin, while passing through a slitter/rewind apparatus, to produce several rolls of material that comprise different levels of pulp and glycerin. The pulp sheets were then fed into a commercial sized hammermill connected to a pocket former and an adult incontinent product manufacturing line. During the final stage of manufacture, the products made from these pulps treated with various levels of glycerin were passed through a set of debulking rolls set to a constant pressure for the entire range of materials. The finished products were then opened up and the densities of the core material was tested. Results are as follows:

| Sample | Basis Weight (g/m$^2$) | Density (g/cm$^3$) |
| --- | --- | --- |
| 0% Glycerin | 673 | 0.173 |
| 5% Glycerin | 730 | 0.192 |
| 6% Glycerin | 701 | 0.162 |
| 7% Glycerin | 767 | 0.199 |
| 8% Glycerin | 673 | 0.228 |
| 9% Glycerin | 721 | 0.237 |
| 9% Glycerin (aged) | 653 | 0.282 |

The percentages given above are weight percent glycerin based on the dry weight of pulp fibers. The 9% aged glycerin sample had glycerin applied to the pulp sheet approximately three months prior to feeding to the commercial sized hammermill. These results demonstrate that increasing levels of glycerin on pulp fibers yield products with increasing densities for a given set of densifying conditions. Based on the results for the aged sample, it is believed that the additional time allowed for additional hydrogen bond disruption within the cellulose fibers.

EXAMPLE 39

This example illustrates how adding other densifying agents, along with glycerin produces a product that is easier to densify than untreated pulp fibers.

A sample of NB 416 pulp sheet (available from Weyerhaeuser Company, Tacoma, Wash.) was sprayed with a solution of 33% lactose and 66% glycerin so that the resulting product was comprised of 91% O.D. (i.e. oven dried) pulp and 9% additive. A second sample of pulp sheet was sprayed with a solution of 50% glucose and 50% glycerin to obtain a product with similar add-on levels.

These products were then, in turn, processed in a manner similar to that described in Example 38. Measurement of the core densities of the products made from these materials yielded the following results:

| Sample | Basis Weight (g/m$^2$) | Density (g/cm$^3$) |
| --- | --- | --- |
| 0% Glycerin | 673 | 0.173 |
| 3% Lactose/6% Glycerin | 689 | 0.263 |
| 4.5% Glucose/4.5% Glycerin | 751 | 0.228 |

These results demonstrate that densifying agents in addition to glycerin on pulp fibers yield products with increased densities for a given set of densification conditions.

EXAMPLE 40

This example illustrates how adding other densifying agents, by themselves, also produces a product that is easier to densify than an untreated pulp.

Samples of NB 416 pulp sheet (available from Weyerhaeuser Company, Tacoma, Wash.) were treated, by passing through a roll coating device, with solutions of 70% sorbitol; 64% sorbitol and 6.4% lactic acid; and 51.2% sorbitol, 12.8% tetrapotassium pyrophosphate, and 6.4% lactic acid respectively to produce sheets with 8%–9% add-on levels of densifying agent per sample. The sheets were then air dried over night and the treated pulp sheets were then fed into a Fitz hammermill fitted with a 1 in$^2$ square holed screen, shunted to an air lay machine (an M & J air lay machine from the M & J Company, Horsens, Denmark) and air laid into a web. Similar samples were made from an untreated pulp sheet and one treated with 9% glycerin alone. All three of the sample webs and the two control webs were then passed through a set of debulking rolls set to a pressure of 25 psi and the densities of the resulting materials was determined with the following results:

| Sample | Basis Weight (g/m$^2$) | Density (g/cm$^3$) |
| --- | --- | --- |
| 0% Glycerin | 176 | 0.1270 |
| 9% Glycerin | 168 | 0.2242 |
| 9% Sorbitol | 167 | 0.1904 |
| 8% Sorbitol/1% Lactic acid | 178 | 0.1396 |
| 6% Sorbitol/2% Potassium Pyrophosphate/1% Lactic acid | 172 | 0.1719 |

These results clearly demonstrate that other densifying agents on pulp also yield products with increased densities for a given set of processing conditions.

EXAMPLE 41

This example illustrates how the method of adding glycerin to some crosslinked pulps yields a product that is easier to densify than a corresponding untreated crosslinked pulp.

300 gram samples of HBA and HBAFF (crosslinked pulps produced by Weyerhaeuser Company, Tacoma, Wash.) were each air entrained in a blenderlike mixing device and 33 grams of glycerin dissolved in 50 milliters of deionized water was sprayed onto the pulp. In each case, the mixer was stopped, the product was v acuum ed out and allowed to dry overnight. Ten gram samples of the treated pulps and ten gram sampless of the orresponding untreated pulps were air laid into 6 inch diameter pads in a laboratory pad former then pressed at 700 psi for one minute. The thickness of the resulting pads was determined and densites were calculated with the following results:

| Sample | Basis Weight (g/m$^2$) | Density (g/cm$^3$) |
| --- | --- | --- |
| HBAFF | 542 | 0.206 |
| HBAFF/10% Glycerin | 520 | 0.285 |
| HBA | 529 | 0.128 |
| HBA/10% Glycerin | 521 | 0.0942 |

These results show that in the case of HBAFF, addition of the glycerin gives a product that is more easily densified for a given set of densifyng conditions.

The following example demonstrates how the application of certain densifying agents in accordance with the present invention on pulp yield pro du cts with improved softness for a given set of processing conditions.

EXAMPLE 42

This example illustrates how certain densifying agents affect the stiffless which is one aspect of the softness of an air laid web of fibers treated with a densifying agent.

A sample of NB 416 pulp sheet (available from Weyerhaeuser Company, Tacoma, Wash.) was treated, by passing through a roll coating device to coat the pulp sheet to 5.8% weight (of a mixture of equal amounts of sorbitol and lactic acid) based on the mass of the fibers and added densifying agents. Another sample of NB 416 was sprayed with a solution of 50% TKPP to a level of 5% TKPP based on the mass of the fibers and TKPP. The sheets were then air dried over night and the treated pulp sheets and an untreated control were then fed into a Fitz hammermill fitted with a 1 in$^2$ square holed screen, while simultaneously adding IM 3900 (a superabsorbent available from Hoechst Celanese, of Portsmouth, Va.)at a rate to produce a material that was 60% treated fiber and 40% IM 3900. This mixture was shunted to an air lay machine (an M & J air lay machine from the M & J Company, Horsens, Denmark) and air laid into webs. Samples of each of the webs were placed in a flat press and pressed to obtain an equivalent density. Press conditions were adjusted so that all the samples were densified to approximately equal densities. The Gurley Stiffness test was then performed on each of the pressed samples with the following results:

| Sample | Density (g/cm$^3$) | Gurley Stiffness |
| --- | --- | --- |
| NB 416 | 0.141 | 131.7 |
| 5.8% Sorbitol/Lactic acid | 0.145 | 96.2 |
| 5% TKPP | 0.138 | 125.1 |

The results demonstrate how densified air laid webs of pulp fibers treated with certain densifying agents are less stiff than corresponding densified air laid webs of untreated pulp fibers. This stiffness date when evaluated in combination with other qualities of the web such as compressibility, pressure required to achieve the given density, and drape, give some indication that the treated fibers are softer than untreated fibers.

EXAMPLE 43

This example illustrates how a densifying agent added to pulp fibers produces material with increased mass without an appreciable increase in volume.

A sample of NB 416 pulp sheet (available from Weyerhaeuser Company, Tacoma, Wash.) was treated, by passing through a roll coating device to coat the pulp sheet to 9% glycerin based on the mass of the fibers and glycerin. Another sample of NB 416 was sprayed with a solution of 50% TKPP to a level of 5% TKPP based on the mass of the fibers and TKPP. The sheets were then air dried over night and the treated pulp sheets and an untreated control were then fed into a Fitz hammermill fitted with a 1 in$^2$ square holed screen, while simultaneously adding IM 3900 (a superabsorbent available from Hoechst Celanese, of Portsmouth, Va.)at a rate to produce a material that was 60% treated fiber and 40% IM 3900. This mixture was shunted to an air lay machine (an M & J air lay machine from the M & J Company, Horsens, Denmark) and air laid into webs. Each of the webs had a basis weight of approximately 375 grams/meter$^2$. The undensified webs were then calipered and densities were calculated.

| Sample | Caliper (mm) | Density (g/cm$^3$) |
| --- | --- | --- |
| 0% Glycerin | 4.1 | 0.091 |
| 9% Glycerin | 3.6 | 0.104 |
| 5% TKPP | 2.8 | 0.134 |

The results demonstrate shows how air laid webs made from fibers treated with certain densifying agents exhibit a decreased caliper for the same mass of fibers.

Having illustrated and described the principles of the invention in many preferred embodiments, it should be apparent to those skilled in the art that the invention can be modified in arrangement and detail without departing from such principles. We claim all modifications coming within the spirit and scope of the following claims.

The embodiments of the invention in which an exclusive property or privilege is claimed are defined as follows:

1. In a fibrous product which comprises a wet laid mat of fibers having hydrogen bonding functional sites that can be air laid into a web, compressed, and then released under a first set of conditions to provide a web of air laid fibers densified to a first density, the improvement consisting essentially of:

a wet laid mat of wood pulp fibers having a basis weight of at least 350 grams per square meter to be air laid into a web; and a densifying agent applied to the wet laid mat of wood pulp fibers in an amount effective to increase the density of the air laid web of wood pulp fibers to a value greater than the first density after compressing and then releasing the air laid web of wood pulp fibers having a densifying agent applied thereto under the first set of conditions, wherein the densifying agent consists essentially of a non-polymeric organic material that includes a hydroxyl functionality and the densifying agent and wood pulp fibers form hydrogen bonds in the absence of covalent bonds between the densifying agent and the wood pulp fibers.

2. The fibrous product of claim 1, wherein the wood pulp fibers comprise cellulose molecules, the densifying agent capable of disrupting or promoting the disruption of hydrogen bonds between cellulose molecules or within a cellulose molecule.

3. The fibrous product of claim 1, wherein the non-polymeric organic material is selected from the group consisting of glycerin, sorbitol, propylene glycol, and combinations thereof.

4. The fibrous product of claim 3, wherein the non-polymeric organic material is glycerin.

5. The fibrous product of claim 1, wherein the densifying agent is applied in an amount ranging from about 0.1% to 30.0% by weight based on the weight of the fibers and densifying agent.

6. The fibrous product of claim 1, wherein the fibers include intra-fiber crosslinks.

7. An absorbent article comprising an air laid web formed from the fibrous product of claims 1, 3, or 6.

8. The absorbent article of claim 7 selected from the group consisting of diapers, incontinent devices, bed pads, wipes, feminine hygiene products, and bandages.

9. The fibrous product of claim 1, wherein the densifying agent is a diol.

10. The fibrous product of claim 9, wherein the diol is dipropylene glycol.

11. The fibrous product of claim 10, wherein the diol is propylene glycol.

12. The fibrous product of claim 10, wherein the diol is ethylene glycol.

13. The fibrous product of claim 10, wherein the diol is trimethylene glycol.

14. The fibrous product of claim 10, wherein the diol is 2,3 butane-diol.

15. In a fibrous product which comprises a wet laid mat of wood pulp fibers having hydrogen bonding functional sites that can be air laid into a web, compressed, and then released under a first set of conditions to provide a web of air laid wood pulp fibers densified to a first density, the improvement consisting essentially of:

wet laid wood pulp fibers in a bale form to be air laid into a web; and a densifying agent applied to the wet laid wood pulp fibers in an amount effective to increase the density of the air laid web of wood pulp fibers to a value greater than the first density after compressing and then releasing the air laid web of wood pulp fibers having a densifying agent applied thereto under the first set of conditions, wherein the densifying agent consists essentially of a non-polymeric organic binder that includes a hydroxyl functionality and the densifying agent and the wood pulp fibers form hydrogen bonds in the absence of covalent bonds between the densifying agent and the wood pulp fibers.

16. The fibrous product of claim 15, wherein the densifying agent is applied in an amount ranging from about 0.1% to 30% by weight based on the weight of the fibers and densifying agent.

17. The fibrous product of claim 15, wherein the densifying agent is a diol.

18. The fibrous product of claim 17, wherein the diol is selected from the group consisting of propylene glycol, dipropylene glycol, ethylene glycol, trimethylene glycol and 2,3 butane diol.

19. The fibrous product of claim 18, wherein the densifying agent is propylene glycol or trimethylene glycol.

* * * * *

UNITED STATES PATENT AND TRADEMARK OFFICE
CERTIFICATE OF CORRECTION

PATENT NO.     : 6,340,411 B1
DATED          : January 22, 2002
INVENTOR(S)    : M.R. Hansen et al.

It is certified that error appears in the above-identified patent and that said Letters Patent is hereby corrected as shown below:

<u>Column 65,</u>
Line 18, "claim 10," should read -- claim 9, --
Line 20, "claim 10," should read -- claim 9, --
Line 22, "claim 10," should read -- claim 9, --
Line 24, "claim 10," should read -- claim 9, --

Signed and Sealed this

Second Day of July, 2002

Attest:

Attesting Officer

JAMES E. ROGAN
*Director of the United States Patent and Trademark Office*